(12) United States Patent
Collins et al.

(10) Patent No.: US 7,138,400 B2
(45) Date of Patent: Nov. 21, 2006

(54) SULFAMIDES AS GAMMA-SECRETASE INHIBITORS

(75) Inventors: Ian James Collins, Ware (GB); Joanne Claire Hannam, Bishops Stortford (GB); Timothy Harrison, Great Dunmow (GB); Stephen John Lewis, London (GB); Andrew Madin, Sawbridgeworth (GB); Timothy Jason Sparey, London (GB); Brian John Williams, Great Dunmow (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 351 days.

(21) Appl. No.: 10/415,751

(22) PCT Filed: Oct. 29, 2001

(86) PCT No.: PCT/GB01/04817

§ 371 (c)(1),
(2), (4) Date: May 1, 2003

(87) PCT Pub. No.: WO02/36555

PCT Pub. Date: May 10, 2002

(65) Prior Publication Data

US 2004/0049038 A1   Mar. 11, 2004

(51) Int. Cl.
C07D 211/18 (2006.01)
C07D 285/10 (2006.01)
A61K 31/435 (2006.01)
A61K 31/433 (2006.01)

(52) U.S. Cl. .................. 514/262; 514/278; 546/15; 548/134

(58) Field of Classification Search ............. 546/15; 514/278
See application file for complete search history.

(56) References Cited

U.S. PATENT DOCUMENTS

| 3,406,184 A | 10/1968 | Raasch |
| 3,715,362 A | 2/1973 | Dominianni |
| 5,703,129 A | 12/1997 | Felsenstein et al. |
| 2005/0119293 A1* | 6/2005 | Collins et al. ............. 514/278 |
| 2005/0182109 A1* | 8/2005 | Collins et al. ............. 514/362 |
| 2005/0182111 A1* | 8/2005 | Pineiro et al. ............. 514/372 |
| 2005/0215602 A1* | 9/2005 | Campbell et al. .......... 514/362 |

FOREIGN PATENT DOCUMENTS

WO   WO 98/38156   9/1998

OTHER PUBLICATIONS

Aeberli, P., et al, "Neuropharmacological Investigation of N-Benzylsulfamides," J. Med. Chem., vol. 10(4), pp. 636-642 (Jul. 1967), at p. 637, Table I (compounds 7 and 11).*
Castro, J.L., et al., "Synthesis and Biological Activity of 3-[2-(Dimethylamino) ethyl]-5-[(1,1-dioxo-5-methyl-1,2,5-thiadiazolidin-2-yl)-methyl]-1H-indole and Analogues," J. Med. Chem., vol. 37(19), pp. 3023-3032 (1994) at p. 3027, Table 1, cmpds 8a-8i.*
J. E. Franz, et al.: Journal of Organic Chemistry, vol. 29, No. 10, Oct. 1964, pp. 2922-2927.
S. Itsuno, et al.: Journal of the Chemical Society, Perkin Transactions 1, No. 10, Jul. 15, 1999 pp. 2011-2016.
M. Narisada, et al.: Journal of Medicinal Chemistry, vol. 31, No. 9, Sep. 1988, pp. 1847-1854.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, Oct. 5, 1964.
L. H. Zalkow, et al.: Journal of Organic Chemistry, vol. 28, No. 12, Dec. 1963, pp. 3303-3309.
G.M. Rishton, et al.: "Fenchylamine sulphonamide inhibitors of amyloid beta peptide production by the gamma-secretase proteolytic pathway: potential small-molecule therapeutic agents for the treatment of Alzheimer's disease" Journal of Medicinal Chemistry, vol. 43, No. 12, May 23, 2000 pp. 2297-2299.
J. E. Franz, et al.: Journal of Organic Chemistry, vol. 29, No. 10, Oct. 1964, pp. 2922-2927.
R. Huisgen, et al.: Chemische Berichte, vol. 98, No. 12, Dec. 1965, pp. 3992-4013.
S. Itsuno, et al.: Journal of the Chemical Society, Perkin Transactions 1, No. 10, Jul. 15, 1999 pp. 2011-2016.
M. Narisada, et al.: Journal of Medicinal Chemistry, vol. 31, No. 9, Sep. 1988, pp. 1847-1854.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, Oct. 5, 1964.
L. H. Zalkow, et al.: Journal of Organic Chemistry, vol. 28, No. 12, Dec. 1963, pp. 3303-3309.

* cited by examiner

*Primary Examiner*—Kamal A. Saeed
*Assistant Examiner*—Nyeemah Grazier
(74) *Attorney, Agent, or Firm*—John C. Todaro; Melvin Winokur

(57) ABSTRACT

Novel sulfamides of formula (I) are disclosed. The compounds exert an inhibitory action on the processing of APP by gamma-secretase, and are therefore useful in the treatment or prevention of Alzheimer's disease.

6 Claims, No Drawings

SULFAMIDES AS GAMMA-SECRETASE INHIBITORS

CROSS REFERENCE TO RELATED APPLICATIONS

This application is a U.S. National Phase application under 35 U.S.C. § 371 of PCT Application No. PCT/GB01/04817, filed Oct. 29, 2001, which claims priority under 35 U.S.C. § 119 from GB Application No. 0026827.6, filed Nov. 2, 2000 and GB Application No. 0122685.1, filed Sep. 20, 2001.

The present invention relates to a novel class of compounds their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2): 1–7; ID *research alert* 1997 2(1):1–8; Current Opinion in CPNS Investigational Drugs 1999 1(3):327–332; and Chemistry in Britain, Jan. 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

The present invention provides a novel class of nonpeptidic compounds which are useful in the treatment or prevention of AD by modulating the processing of APP by the putative γ-secretase, thus arresting the production of Aβ and preventing the formation of insoluble plaques.

According to the invention, there is provided a compound of formula I:

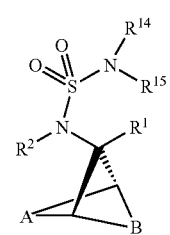

wherein:

A and B are independently selected from —$(CXY)_p$—; —$(CXY)_qCY=CY(CXY)_r$—; —$(CXY)_xNR^{13}(CXY)_y$—;

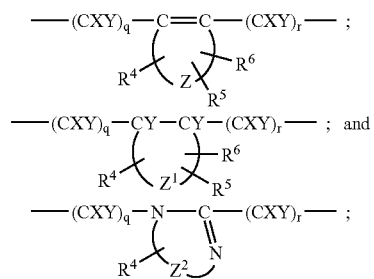

X represents halogen, $R^9$, —$OR^9$, —$SR^9$, —$S(O)_tR^{10}$ where t is 1 or 2, —$OSO_2R^9$, —$N(R^9)_2$, —$COR^9$, —$CO_2R^9$, —$OCOR^{10}$, —$OCO_2R^{10}$, —$CON(R^9)_2$, —$SO_2N(R^9)_2$, —$OSO_2N(R^9)_2$, —$NR^9COR^{10}$, —$NR^9CO_2R^{10}$ or —$NR^9SO_2R^{10}$—;

Y represents H or $C_{1-6}$alkyl;

or X and Y together represent =O, =S, =N—$OR^{11}$ or =$CHR^{11}$;

provided neither A nor B comprises more than one —CXY— moiety which is other than —$CH_2$—;

Z completes an aromatic ring system of 5 to 10 atoms, of which 0 to 3 are selected from nitrogen, oxygen and sulfur and the remainder are carbon, or Z completes a non-aromatic ring system of 5 to 10 atoms, of which 0 to 3 are independently selected from oxygen, nitrogen and sulphur and the remainder are carbon;

$Z^1$ completes a non-aromatic ring system of 5 to 10 atoms, of which 0 to 3 are independently selected from oxygen, nitrogen and sulphur and the remainder are carbon;

$Z^2$ completes a 5- or 6-membered heteroaryl ring;

p is an integer from 1–6;

q and r are independently 0, 1 or 2;

x and y are independently 0, 1 or 2; provided that at least one of A and B comprises a chain of 2 or more atoms, such that the ring completed by A and B contains at least 5 atoms;

$R^1$ represents H, $C_{1-4}$alkyl, or $C_{2-4}$alkenyl, or $R^1$ and $R^{15}$ together may complete a 5-, 6- or 7-membered cyclic sulfamide;

$R^2$ represents H, $C_{1-6}$alkyl, $C_{6-10}$aryl, $C_{6-10}$aryl$C_{1-6}$alkyl, $C_{3-6}$cycloalkyl or $C_{2-6}$acyl which is optionally substituted with a carboxylic acid group or with an amino group;

$R^4$, $R^5$ and $R^6$ independently represent $R^9$, halogen, CN, $NO_2$, —$OR^9$, —$SR^9$, —$S(O)_tR^{10}$ where t is 1 or 2, —$N(R^9)_2$, —$COR^9$, —$CO_2R^9$, —$OCOR^{10}$, —CH=N—$OR^{11}$, —$CON(R^9)_2$, —$SO_2N(R^9)_2$, —$NR^9COR^{10}$, —$NR^9CO_2R^{10}$, —$NR^9SO_2R^{10}$, —CH=CHCH$_2$N(R$^{16}$)$_2$, —$CH_2OR^{10}$, —$CH_2N(R^{16})_2$, —$NHCOCH_2OR^{10}$ or —$NHCOCH_2N(R^{16})_2$;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or —$C_{1-6}$alkylAr;

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, —$COR^{12}$ or —$SO_2R^{12}$—;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, heterocyclyl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$; or two $R^{11}$ groups together with a nitrogen atom to which they are mutually attached may complete a heterocyclic ring system of 3–10 atoms, 0–2 of which (in addition to said nitrogen atom) are selected from O, N and S, said ring system bearing 0–2 substituents selected from halogen, CN, $NO_2$, oxo, $R^{12}$, OH, $OR^{12}$, $NH_2$, $NHR^{12}$, CHO, $CO_2H$, $COR^{12}$ and $CO_2R^{12}$;

$R^{12}$ represents $C_{1-6}$alkyl which is optionally substituted with halogen, CN, OH, $C_{1-4}$alkoxy or $C_{1-4}$alkoxycarbonyl; perfluoro$C_{1-6}$alkyl, $C_{3-7}$cycloalkyl, $C_{2-6}$alkenyl, $C_{2-6}$alkynyl, Ar, —$C_{1-6}$alkylAr, ArO$C_{1-6}$alkyl or C-heterocyclyl which is optionally substituted with halogen, CN, $C_{1-6}$alkyl, OH, perfluoro$C_{1-6}$alkyl, $C_{2-6}$acyl, $C_{1-4}$alkoxy or $C_{1-4}$alkoxycarbonyl;

$R^{13}$ represents $R^9$, —$COR^{10}$, —$CO_2R^{10}$, —$SO_2R^{10}$, —$CON(R^9)_2$ or —$SO_2N(R^9)_2$;

$R^{14}$ represents H, $C_{1-10}$alkyl, perfluoro$C_{1-6}$alkyl, $C_{3-10}$cycloalkyl, $C_{3-6}$cycloalkyl$C_{1-16}$alkyl, $C_{2-10}$alkenyl, $C_{2-10}$alkynyl, $C_{6-10}$aryl, heteroaryl, $C_{6-10}$aryl$C_{1-6}$alkyl, or heteroaryl$C_{1-6}$alkyl, wherein the alkyl, cycloalkyl, alkenyl and alkynyl groups optionally bear one substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$, and the aryl and heteroaryl groups optionally bear up to 3 substituents selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkylNR$^7$COR$^8$, —$NR^7CO_2R^8$ and —$NR^7SO_2R^8$;

$R^{15}$ represents H or $C_{1-6}$alkyl; or $R^{15}$ and $R^1$ together complete a 5-, 6- or 7-membered cyclic sulfamide;

each $R^{16}$ independently represents H or $R^{10}$, or two $R^{16}$ groups together with the nitrogen to which they are mutually attached complete a mono- or bicyclic heterocyclic ring system of 5–10 ring atoms selected from C, N, O and S, said ring system optionally having an additional aryl or heteroaryl ring fused thereto, said heterocyclic system and optional fused ring bearing 0–3 substituents independently selected from halogen, oxo, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

or a pharmaceutically acceptable salt thereof.

In a subset of the compounds according to formula I, $R^1$ represents H, $C_{1-4}$alkyl, or $C_{2-4}$alkenyl, or $R^1$ and $R^{15}$ together may complete a 5-membered cyclic sulfamide;

$R^4$, $R^5$ and $R^6$ independently represent $R^9$, halogen, CN, $NO_2$, —$OR^9$, —$SR^9$, —$S(O)_tR^{10}$ where t is 1 or 2, —$N(R^9)_2$, —$COR^9$, —$CO_2R^9$, —$OCOR^{10}$, —$CON(R^9)_2$, —$SO_2N(R^9)_2$, —$NR^9COR^{10}$, —$NR^9CO_2R^{10}$, —$NR^9SO_2R^{10}$, —CH=CHCH$_2$N(R$^{16}$)$_2$, —$CH_2OR^{10}$, —$CH_2N(R^{16})_2$, —$NHCOCH_2OR^{10}$ or —$NHCOCH_2N(R^{16})_2$;

$R^{10}$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl, or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_{12}R^2$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$;

$R^{12}$ represents $C_{1-6}$alkyl, perfluoro$C_{1-6}$alkyl, $C_{3-7}$cycloalkyl, $C_{2-6}$alkenyl, $C_{2-6}$alkynyl, Ar, —$C_{1-6}$alkylAr or ArO$C_{1-6}$alkyl;

$R^{15}$ represents H or $C_{1-6}$alkyl; or $R^{15}$ and $R^1$ together complete a 5-membered cyclic sulfamide; and each $R^{16}$ independently represents H or $R^{10}$, or two $R^{16}$ groups together with the nitrogen to which they are mutually attached complete a mono- or bicyclic heterocyclic ring system of 5–10 ring atoms selected from C, N, O and S, said ring system optionally having an additional aryl or heteroaryl ring fused thereto, said heterocyclic system and/or additional fused ring bearing 0–3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl"$C_{1-6}$alkyl, "$C_{2-6}$alkynyl" and "$C_{1-6}$alkoxy" are to be construed in an analogous manner.

The expression "perfluoro$C_{1-6}$alkyl" as used herein refers to alkyl groups as defined above comprising at least one —$CF_2$— or —$CF_3$ group.

The expression "$C_{3-10}$cycloalkyl" as used herein refers to nonaromatic monocyclic or fused bicyclic hydrocarbon ring systems comprising from 3 to 10 ring atoms. Bicyclic systems comprising a nonaromatic hydrocarbon ring of 3–6 members which is fused to a benzene ring are also included. Examples include cyclopropyl, cyclobutyl, cyclopentyl, cyclohexyl, cyclohexenyl, decalinyl, tetralinyl and indanyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$ alkyl)carbonyl groups, such as acetyl, propanoyl and butanoyl, including cycloalkyl derivatives such as cyclopentanecarbonyl and cyclobutanecarbonyl.

$C_{6-10}$aryl groups include phenyl and naphthyl, preferably phenyl.

The expression "$C_{6-10}$aryl$C_{1-6}$alkyl, " as used herein includes benzyl, phenylethyl, phenylpropyl and naphthylmethyl.

The expression "heterocyclyl" as used herein means a cyclic or polycyclic system of up to 10 ring atoms selected from C, N, O and S, wherein at least one ring atom is other than carbon and said atom is part of a non-aromatic ring. Preferably not more than 3 ring atoms are other than carbon. Suitable heterocyclyl groups include azetidinyl, pyrrolidinyl, tetrahydrofuryl, piperidinyl, piperazinyl, morpholinyl, thiomorpholinyl, tetrahydropyranyl, tetrahydropyridinyl, imidazolinyl, dioxanyl, benzodioxanyl and 5-aza-2-oxabicyclo[2.2.1]heptyl. Unless indicated otherwise, attachment of heterocyclyl groups may be through a carbon or nitrogen atom forming part of the heterocyclic ring. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine and 1,3,5-triazine The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds in accordance with the invention exist as enantiomers by virtue of the asymmetry of the molecule as a whole. For example, the compounds of formula I in which A comprises a monosubstituted fused benzene ring lack a plane of symmetry, and hence exist as pairs of enantiomers, the interconversion of which is prevented by the rigidity of the bridged bicycloalkyl ring structure. It is to be understood that all such isomers and mixtures thereof in any proportion are encompassed within the scope of the present invention, and that structural formulae depicting asymmetric molecules of this type shall be representative of both of the possible enantiomers, unless otherwise indicated.

The compounds of formula I are sulfamido-substituted bridged bicycloalkyl derivatives, optionally comprising a further fused ring system. In some embodiments, the sulfamide group forms part of a spiro-linked ring of 5, 6 or 7 members.

In the definition of A and B in formula I, p is an integer from 1 to 6, preferably from 2 to 5, and most preferably is 3 or 4;

q and r are independently 0, 1 or 2 but are preferably both 1 or both 0;

and x and y are independently 0, 1 or 2, but are preferably not both 0;

with the proviso that at least one of A and B must comprise a chain of 2 or more atoms, such that the ring completed by A and B contains at least 5 atoms. Thus, for example, if A and B represent —$(CXY)_p$— and —$(CXY)_x$—$NR^{13}$—$(CXY)_y$— respectively, then p must be greater than 1 or at least one of x and y must be greater than 0.

X represents halogen, $R^9$, —$OR^9$, —$SR^9$, —$S(O)_tR^{10}$ where t is 1 or 2, —$OSO_2R^9$, —$N(R^9)_2$, —$COR^9$, —$CO_2R^9$, —$OCOR^{10}$, —$OCO_2R^{10}$, —$CON(R^9)_2$, —$SO_2N(R^9)_2$, —$OSO_2N(R^9)_2$, —$NR^9COR^{10}$, —$NR^9CO_2R^{10}$ or —$NR^9SO_2R^{10}$; wherein $R^9$ and $R^{10}$ are as defined above. Alternatively, X and Y together may represent =O, =S, =N—$OR^{11}$ or =$CHR^{11}$. Typically, X represents H, $C_{1-4}$alkyl, substituted $C_{1-4}$alkyl, —$OR^{9a}$, —$COR^{9a}$, —$CO_2R^{9a}$, —$OCOR^{10a}$, —$N(R^{9a})_2$, —$CON(R^{9a})_2$, —$OCO_2R^{10a}$, —$OSO_2R^{10a}$ or (in combination with Y) =O, =S, =N—$OR^{11}$ or =$CH_2$, where $R^{9a}$ is H or $R^{10a}$, and $R^{10a}$ is $C_{1-6}$alkyl, $C_{2-6}$alkenyl, Ar (especially phenyl) or benzyl. Preferred embodiments of X include H, methyl, hydroxymethyl, —$CO_2Et$, and (in combination with Y) =O, =S, =N—OMe, =N—OEt, =N—OPh, =N—$OCH_2Ph$ and =$CH_2$.

Y may represent H or $C_{1-6}$alkyl, or may combine with X as indicated above. Preferably, Y represents H or together with X represents =O, =S, =N—OMe, =N—OEt, =N—OPh, =N—$OCH_2Ph$ or =$CH_2$.

Neither A nor B may comprise more than one —CXY— moiety which is other than —$CH_2$—.

When A and/or B comprises a —$NR^{13}$— moiety, $R^{13}$ preferably represents H, optionally-substituted $C_{1-6}$alkyl, $C_{2-6}$alkenyl or $C_{6-10}$aryl$C_{1-6}$alkyl. Particular values for $R^{13}$ include H, methyl, ethyl, allyl, cyanomethyl, carbamoylmethyl, methoxycarbonylmethyl, benzyl, chlorobenzyl and methoxybenzyl. Preferably, A and B do not both comprise a —NR$^{13}$— moiety.

Suitable embodiments of A and B include:
—CXY—, —CH$_2$CXY—, —CH$_2$CXYCH$_2$—, —CH$_2$CH$_2$CXYCH$_2$—, —CH=CH—, —CH$_2$CH=CHCXY—, —CH$_2$NR$^{13}$CXY—, —CH$_2$CH$_2$NR$^{13}$CXY—, —CH$_2$CXYNR$^{13}$CH$_2$—, —CXYCH$_2$NR$^{13}$CH$_2$—, —NR$^{13}$CXY—,

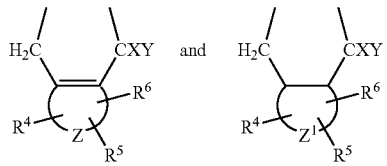

Preferred embodiments of A include —CH$_2$CH$_2$CH$_2$—, —CH$_2$CH$_2$—, —CH$_2$CH$_2$CH$_2$CH$_2$—, —CH$_2$CH=CHCH$_2$—, and

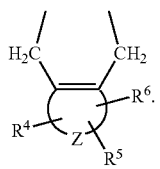

Typical embodiments of B include —CH$_2$—, —CH$_2$CH$_2$—, —CH$_2$CH$_2$CH$_2$—, —CH$_2$CH$_2$CH$_2$CH$_2$—, —CH=CH—, and —CH$_2$CH=CHCH$_2$—, and preferred embodiments of B include —CH$_2$CH$_2$— and —CH$_2$CH$_2$CH$_2$—.

Z completes an aromatic ring system containing 5–10 atoms, of which 0–3 are selected from nitrogen, oxygen and sulfur and the remainder are carbon (in particular, an aromatic ring system containing 6–10 atoms, of which 0–2 are nitrogen and the remainder are carbon), or Z completes a non-aromatic ring system containing 5–10 atoms, of which 0–3 are independently selected from oxygen, nitrogen and sulphur and the remainder are carbon. Examples of aromatic ring systems completed by Z include benzene, naphthalene, pyridine, quinoline, isoquinoline, pyrazine, pyrimidine, pyrrole, furan, thiophene, indole, benzofuran, benzothiophene, oxazole, isoxazole, thiazole, isothiazole and triazole. Examples of non-aromatic ring systems completed by Z include cyclohexane, cyclopentane, indane, tetralin, decalin, piperidide, piperazine, morpholine, tetrahydrofuran and tetrahydrothiophene. Preferably, Z completes a benzene ring or a pyridine ring.

Z$^1$ completes a non-aromatic ring system containing 5–10 atoms, of which 0–3 are independently selected from oxygen, nitrogen and sulphur and the remainder are carbon. Examples of ring systems completed by Z$^1$ include cyclohexane, cyclopentane, indane, tetralin, decalin, piperidine, piperazine, morpholine, tetrahydrofuran and tetrahydrothiophene.

Z$^2$ completes a heteroaromatic ring comprising 5 or 6 atoms, such as imidazole, triazole or pyrimidine.

A fused ring (as indicated by Z, Z$^1$ or Z$^2$) may form part of A or B, but A and B preferably do not both comprise such a ring. Typically, such fused rings (if present) form part of A.

Examples of structures completed by A and B include (but are not restricted to):

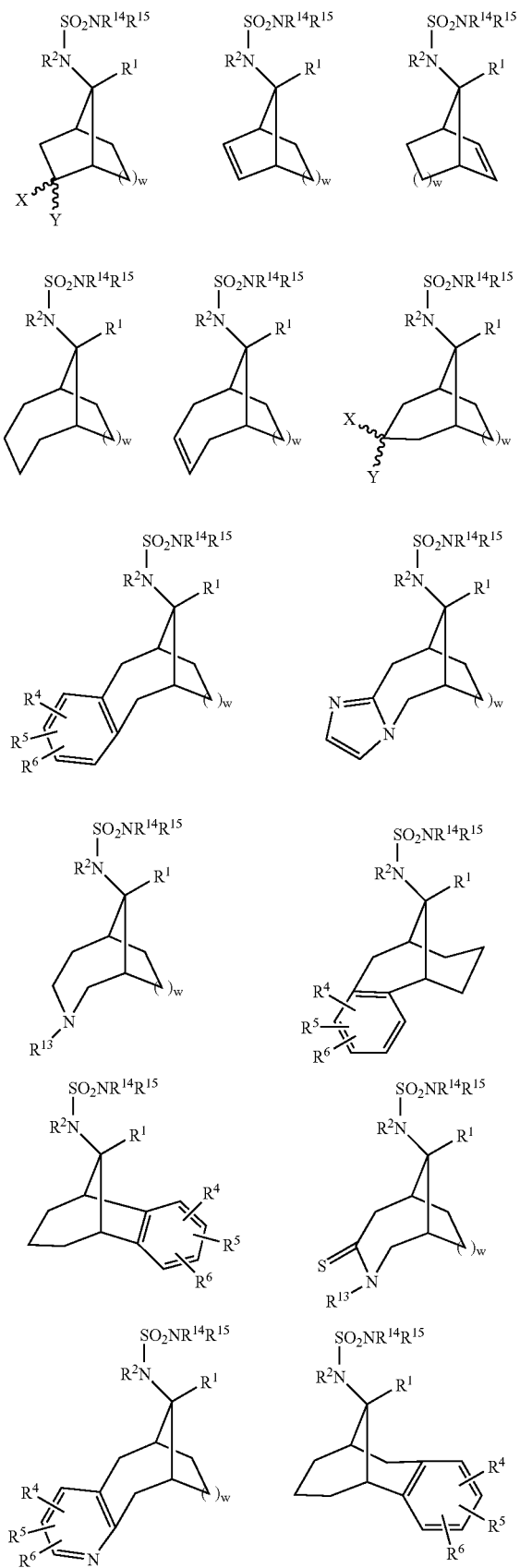

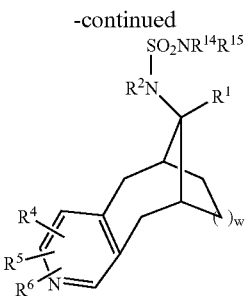

where w is 1 or 2, and X, Y, $R^1$, $R^2$, $R^4$, $R^5$, $R^6$, $R^{13}$, $R^{14}$ and $R^{15}$ have the same meanings as before.

Examples of preferred structures include:

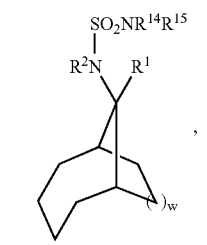

II

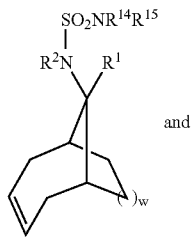

III and

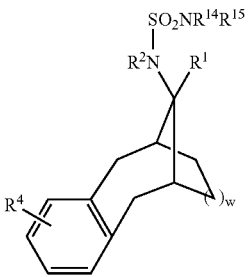

IV wherein w, $R^1$, $R^2$, $R^4$, $R^{14}$ and $R^{15}$ have the same meanings as before.

$R^1$ represents H, $C_{1-4}$alkyl (such as methyl, ethyl, isopropyl or t-butyl), $C_{2-4}$alkenyl (such as allyl), or $R^1$ and $R^{15}$ together complete a cyclic sulfamide containing 5, 6 or 7 ring atoms. Preferably, $R^1$ represents H, methyl or allyl, or together with $R^{15}$ completes a cyclic sulfamide containing 5 or 6 ring atoms. Most preferably, $R^1$ represents H, or together with $R^{15}$ completes a cyclic sulfamide containing 5 or 6 ring atoms.

$R^2$ represents H, $C_{1-6}$alkyl (such as methyl, ethyl, propyl or butyl), $C_{6-10}$aryl (such as phenyl or naphthyl), $C_{6-10}$aryl$C_{1-6}$alkyl (such as benzyl), $C_{3-6}$cycloalkyl (such as cyclopropyl, cyclopentyl or cyclohexyl), or $C_{2-6}$acyl which is optionally substituted with —$CO_2H$ (such as acetyl, malonoyl, succinoyl or glutaroyl), or with an amino group, in particular a primary amino group or an alkyl- or dialkylamino group in which the alkyl group(s) comprise(s) up to 4 carbons. Preferably, $R^2$ is H.

$R^{14}$ represents H, $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, $C_{6-10}$aryl$C_{1-6}$alkyl, or heteroaryl$C_{1-6}$alkyl, wherein the alkyl, cycloalkyl, alkenyl and alkynyl groups optionally bear one substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkyl$NR^7COR^8$, —$NR^7CO_2R^8$ and —$NR^7SO_2R^8$, and the aryl and heteroaryl groups optionally bear up to 3 substituents selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$C_{1-6}$alkyl$NR^7COR^8$, —$NR^7CO_2R^8$ and —$NR^7SO_2R^8$, where $R^7$ represents H or $R^8$; or two $R^7$ groups together with a nitrogen atom to which they are mutually attached may complete a pyrrolidine, piperidine, piperazine or morpholine ring, while $R^8$ represents $C_{1-10}$alkyl, perfluoro$C_{1-6}$alkyl, $C_{3-10}$cycloalkyl, $C_{3-6}$cycloalkyl$C_{1-6}$alkyl, $C_{2-10}$alkenyl, $C_{2-10}$alkynyl, Ar or —$C_{1-6}$alkylAr, where Ar represents phenyl or heteroaryl either of which optionally bears up to 3 substituents independently selected from halogen, $CF_3$, $NO_2$, CN, $C_{1-6}$alkyl and $C_{1-6}$alkoxy. Preferably, $R^7$ and $R^8$ are independently selected from H, $C_{1-6}$alkyl (especially methyl, ethyl, n-propyl or isopropyl), perfluoro$C_{1-6}$alkyl (especially trifluoromethyl or 2,2,2-trifluoroethyl), Ar (especially phenyl optionally bearing up to 3 substituents independently selected from halogen, $CF_3$, $NO_2$, CN, $C_{1-6}$alkyl and $C_{1-6}$alkoxy) and —$C_{1-6}$alkylAr (especially benzyl optionally bearing up to 3 substituents independently selected from halogen, $CF_3$, $NO_2$, CN, $C_{1-6}$alkyl and $C_{1-6}$alkoxy), with the proviso that $R^8$ cannot be H.

$R^{14}$ preferably represents optionally substituted $C_{1-10}$alkyl (such as methyl, ethyl, n-propyl, isopropyl, n-butyl, t-butyl, sec-butyl, cyanomethyl, 2-fluoroethyl and methoxyethyl), perfluoro$C_{1-6}$alkyl (such as trifluoromethyl and 2,2,2-trifluoroethyl), $C_{3-10}$cycloalkyl (such as cyclopropyl, cyclobutyl, cyclopentyl and cyclohexyl), $C_{3-6}$cycloalkyl$C_{1-6}$alkyl (such as cyclopropylmethyl, cyclobutylmethyl and cyclopentylmethyl), $C_{2-6}$alkenyl (such as allyl), $C_{2-6}$alkynyl (such as propargyl), $C_{6-10}$aryl (such as phenyl) or $C_{6-10}$aryl$C_{1-6}$alkyl (such as benzyl which optionally bears up to 2 halogen substituents).

$R^{15}$ represents H or $C_{1-6}$alkyl (such as methyl or ethyl), preferably H. Alternatively, $R^{15}$ and $R^1$ together complete a cyclic sulfamide of 5, 6 or 7 ring atoms, preferably 5 or 6 ring atoms, and most preferably 5 ring atoms.

$R^4$, $R^5$ and $R^6$ independently represent $R^9$, halogen, CN, $NO_2$, —$OR^9$, —$SR^9$, —$S(O)_tR^{10}$ where t is 1 or 2, —$N(R^9)_2$, —$COR^9$, —$CO_2R^9$, —$OCOR^{10}$, —CH=N—$OR^{11}$, —$CON(R^9)_2$, —$SO_2N(R^9)_2$, —$NR^9COR^{10}$, —$NR^9CO_2R^{10}$, —$NR^9SO_2R^{10}$, —CH=CHCH$_2$N($R^{16}$)$_2$, —$CH_2OR^{10}$, —$CH_2N(R^{16})_2$, —$NHCOCH_2OR^{10}$ or —$NHCOCH_2N(R^{16})_2$; where $R^9$, $R^{10}$, $R^{11}$ and $R^{16}$ are as defined previously. When the group A or B comprises a non-aromatic ring completed by Z or $Z^1$, $R^4$, $R^5$ and $R^6$ preferably all represent hydrogen. When A or B comprises an aromatic ring completed by Z, $R^4$, $R^5$ and $R^6$ are preferably independently selected from $R^9$, halogen, CN, $NO_2$, —$OR^9$, —$N(R^9)_2$, —$NR^9COR^{10}$, —$NR^9CO_2R^{10}$, —CH=N—$OR^{11}$, —CH=CHCH$_2$N($R^{16}$)$_2$, —$CH_2OR^9$, —$CH_2N(R^{16})_2$, —$NHCOCH_2OR^{10}$ and —$NHCOCH_2N$ $(R^{16})_2$, but preferably at least one of $R^5$ and $R^6$ represents H, and most preferably both of $R^5$ and $R^6$ represent H.

When A or B comprises a heteroaromatic ring completed by $Z^2$, $R^4$ preferably represents H.

$R^9$ represents H or $R^{10}$; or two $R^9$ groups together with a nitrogen atom to which they are mutually attached may complete a pyrrolidine, piperidine, piperazine or morpholine ring which is optionally substituted by $R^{12}$, —$COR^{12}$ or —$SO_2R^{12}$, while $R^{10}$ represents $C_{1-10}$alkyl, perfluoro$C_{1-6}$ alkyl, $C_{3-10}$cycloalkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, heteroaryl$C_{1-6}$alkyl, heterocyclyl$C_{1-6}$ alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$, where $R^{11}$ and $R^{12}$ are as defined previously. Preferably, $R^9$ and $R^{10}$ independently represent H, $C_{1-10}$alkyl, perfluoro$C_{1-6}$alkyl, $C_{3-6}$cycloalkyl$C_{1-6}$alkyl, $C_{2-10}$alkenyl, $C_{2-10}$alkynyl, $C_{6-10}$aryl, heteroaryl, heterocyclyl, $C_{6-10}$aryl$C_{1-6}$alkyl, $C_{6-10}$aryl$C_{2-6}$alkenyl, heteroaryl$C_{2-6}$alkenyl, heterocyclyl$C_{1-6}$alkyl or heteroaryl$C_{1-6}$alkyl, wherein the alkyl, cycloalkyl, alkenyl and alkynyl groups are unsubstituted or substituted by CN, —$OR^{11}$, —$N(R^{11})_2$, —$COR^{11}$, —$CO_2R^{11}$ or —$CON(R^{11})_2$, and wherein the aryl, heteroaryl and heterocyclyl groups bear not more than two substituents selected from halogen, $NO_2$, CN, $R^{12}$, —$OR^{11}$ and —$SO_2R^{12}$, with the proviso that $R^{10}$ cannot represent H.

$R^{11}$ represents H or $R^{12}$; or two $R^{11}$ groups together with a nitrogen atom to which they are mutually attached may complete a heterocyclic ring system of 3–10 atoms, 0–2 of which (in addition to said nitrogen atom) are selected from O, N and S, said ring system bearing 0–2 substituents selected from halogen, CN, $NO_2$, oxo, $R^{12}$, OH, $OR^{12}$, $NH_2$, $NHR^{12}$, CHO, $CO_2H$, $COR^{12}$ and $CO_2R^{12}$; while $R^{12}$ represents $C_{1-6}$alkyl which is optionally substituted with halogen, CN, OH, $C_{1-4}$alkoxy or $C_{1-4}$alkoxycarbonyl; $C_{3-7}$cycloalkyl, perfluoro$C_{1-6}$alkyl, $C_{2-6}$alkenyl, $C_{2-6}$alkynyl, ArO$C_{1-6}$alkyl, Ar, —$C_{1-6}$alkylAr, or C-heterocyclyl which is optionally substituted with halogen, CN, $C_{1-6}$alkyl, OH, perfluoro$C_{1-6}$alkyl, $C_{2-6}$acyl, $C_{1-4}$alkoxy or $C_{1-4}$alkoxycarbonyl; where Ar represents phenyl or heteroaryl either of which optionally bears up to 3 substituents independently selected from halogen, $CF_3$, $NO_2$, CN, $OCF_3$, $C_{1-6}$alkyl and $C_{1-6}$alkoxy. Preferably, $R^{11}$ and $R^{12}$ independently represent H, optionally substituted $C_{1-6}$alkyl, perfluoro$C_{1-6}$alkyl, $C_{2-6}$alkenyl, $C_{2-6}$alkynyl, phenyl (optionally bearing up to 2 substituents independently selected from halogen, $CF_3$, $NO_2$, CN, $C_{1-6}$alkyl and $C_{1-6}$alkoxy), heteroaryl (optionally substituted by halogen, $CF_3$ or $C_{1-6}$alkyl), heteroaryl$C_{1-6}$ alkyl (such as pryidylmethyl or thienylmethyl), benzyl (optionally bearing up to 2 substituents independently selected from halogen, $CF_3$, $NO_2$, CN, $C_{1-6}$alkyl and $C_{1-6}$alkoxy), or optionally-substituted C-heterocyclyl (such as piperidin-4-yl or 1-acetylpiperidin-4-yl), with the proviso that $R^{12}$ cannot represent H. Alternatively, two $R^{11}$ groups together with a nitrogen atom to which they are mutually attached complete a heterocyclic ring system. Examples of heterocyclic groups represented by $N(R^{11})_2$ include morpholin-4-yl, pyrrolidin-1-yl, 2-oxopyrrolidin-1-yl, 2-oxo-imidazolin-1-yl, piperidin-1-yl, 4,4-difluoropiperidin-1-yl, 4-trifluoromethylpiperidin-1-yl, 5-aza-2-oxa-[2.2.1]bicyclohept-5-yl, piperazin-1-yl, 4-methylpiperazin-1-yl, 3-oxo-4-phenylpiperazin-1-yl and 4-acetylpiperazin-1-yl.

Each $R^{16}$ independently represents H or $R^{10}$, or two $R^{16}$ groups together with the nitrogen to which they are mutually attached complete a mono- or bicyclic heterocyclic ring system of 5–10 ring atoms selected from C, N, O and S, said ring system optionally having an additional aryl or heteroaryl ring fused thereto, said heterocyclic system and optional fused ring bearing 0–3 substituents independently selected from halogen, oxo, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$. Examples of heterocyclic ring systems represented by —$N(R^{16})_2$ include pyrrolidine, piperidine, piperazine, morpholine, thiomorpholine, 2,5-diazabicyclo[2,2,1]heptane, 5,6-dihydro-8H-imidazo[1,2-α]pyrazine and spiro[isobenzofuran-1(3H),4'-piperidine]. Preferred substituents include halogen, OH, oxo and $R^{12}$ groups, such as alkyl, cycloalkyl, perfluoroalkyl, phenoxyalkyl, pylidyl and phenyl, wherein the pyridyl and phenyl groups optionally bear up to 2 substituents selected from halogen (especially chlorine or fluorine), $C_{1-6}$alkyl and $C_{1-6}$alkoxy.

$R^4$ very aptly represents halogen (especially chlorine, bromine or fluorine), nitro, CN, phenyl, substituted phenyl (such as 3,5-bis(trifluoromethyl)phenyl, o-anisyl, 2-fluorophenyl, 3-fluorophenyl and 4-fluorophenyl), heteroaryl, oximino or alkoximino represented by —CH═$NOR^{11}$, amino represented by —$N(R^9)_2$, amido represented by —$NR^9COR^{10}$, carbamate represented by —$NR^9CO_2R^{10}$, alkoxy represented by —$OR^{10}$, optionally substituted alkenyl, including —CH═$CHCH_2N(R^{16})_2$ $C_{6-10}$aryl$C_{2-6}$alkenyl and heteroaryl$C_{2-6}$alkenyl, substituted acetamido represented by —$NHCOCH_2(NR^{16})_2$ and —$NHCOCH_2OR^{10}$, or substituted methyl represented by —$CH_2OR^9$.

$R^4$ also very aptly represents H, OH, CHO, $CO_2H$, alkoxycarbonyl represented by $CO_2R^{10}$ (such as methoxycarbonyl and ethoxycarbonyl) or substituted $C_{1-6}$alkyl (in particular, $C_{1-6}$alkyl which is substituted by —$CO_2R^{11}$ or —$N(R^{11})_2$).

Heteroaryl groups represented by $R^4$ are typically 5- or 6-membered rings such as optionally-substituted (and optionally benzo-fused) pyridine, furan, thiophene, pyrrole, pyrazole, imidazole, triazole, oxazole, isoxazole, thiazole, isothiazole, oxadiazole and thiadiazole. A particular subclass of heteroaryl groups represented by $R^4$ are 5-membered heteroaryl rings which are optionally substituted with Ar. Ar in this context typically represents (but is not restricted to) phenyl, halophenyl, pyridyl or pyrazinyl. Examples of heteroaryl groups within this class include 5-phenyl-1,2,4-oxadiazol-3-yl, 5-(4-fluorophenyl)-1,2,4-oxadiazol-3-yl, 5-phenyl-1,3,4-oxadiazol-2-yl, 5-(4-fluorophenyl)-1,3,4-oxadiazol-2-yl, 5-pyridyl-1,2,4-oxadiazol-3-yl, 3-(4-fluorophenyl)-1,2,4-oxadiazol-5-yl, 5-(4-fluorophenyl)oxazol-2-yl, 3-(pyridin-2-yl)-1,2,4-oxadiazol-5-yl, 3-pyrazinyl-1,2, 4-oxadiazol-5-yl, and 5-(4-fluorophenyl)pyrazol-3-yl. Examples of other heteroaryl groups represented by $R^4$ include 3-thienyl, 2-thienyl, 2-benzofuryl, 4-pyridyl, 3-pyridyl and 6-methoxy-3-pyridyl.

Examples of oximino or alkoximino groups represented by $R^4$ include —CH═NOH, —CH═$NOC_2H_5$, —CH═$NOCH_2CH$═$CH_2$ and —CH═$NOCH_2Ar$. In this context, Ar typically represents (but is not restricted to) a phenyl group bearing 0–2 substituents selected from halogen and $CF_3$.

Typical examples of amino groups represented by $R^4$ include $NH_2$, (3-pyridylmethyl)amino, 4-phenoxybenzylamino, 4-benzyloxybenzylamino, 2-methoxybenzylamino, 3-methoxybenzylamino, 4-methoxybenzylamino, 3,3-dimethylbutylamino, (cyclohexylmethyl)amino, 3-methylbutylamino, (4-pyridylmethyl)amino, 2-benzyloxyethylamino, 2-phenylpropylamino, (2,3-dihydrobenzo[1,4]dioxin-6-ylmethyl)amino, 4-t-butylbenzylamino, 3-phenylbutylamino, 4-isopropoxybenzylamino, (benzofuran-2-ylmethyl)amino, 3-phenylpropylamino, 4-n-pentylbenzylamino, 4-methanesulphonylbenzylamino, 3-(4-t-butylphenoxy)benzylamino, 3-(4-methoxyphenoxy)benzylamino, 3-trifluoromethoxybenzylamino, 4-cyanobenzylamino, 3-fluorobenzylamino, 4-fluorobenzylamino, 3-chlorobenzylamino, 3-trifluoromethylbenzylamino, 3-(3,4-dichlorophenoxy)benzylamino, 4-(4-t-butylthiazol-2-yl)benzylamino, 4-(hex-1-ynyl)benzylamino, 3-benzyloxybenzylamino and 4-phenylpiperidin-1-yl.

Typical examples of amide groups represented by $R^4$ include benzamido, phenylacetamido, 3,5-difluorophenylacetamido, 4-fluorobenzamido, acetamido, propionamido, butyramido, pentanamido, hexanamido, isobutyramido, 3-methylbutyramido, 2-methylbutyramido, 2-methylpentanamido, 3-methylpentanamido, 4-methylpentanamido, 2,2-dimethylbutyramido, 2-ethylbutyramido, cyclopentylacetamido, 2,2-dimethylpent-4-enamido, cyclopropylacetamido, 4-methyloctanamido, 3,5,5-trimethylhexanamido, 2-methylhexanamido, 2,2-dimethylpentanamido, 5-methylhexanamido, 3-phenylpropionamido, isonicotinamido, pyridine-2-carboxamido, nicotinamido and 2-(2,4-dichlorophenoxy)propionamido.

Typical examples of carbamate groups represented by $R^4$ include phenoxycarbonylamino, 4-chlorophenoxycarbonylamino, methoxycarbonylamino, benzyloxycarbonylamino, isobutoxycarbonylamino, allyloxycarbonylamino, 4-methylphenoxycarbonylamino, 4-bromophenoxycarbonylamino, 4-fluorophenoxycarbonylamino, 4-methoxyphenoxycarbonylamino and 2,2-dimethylpropoxycarbonylamino.

When $R^4$ represents an alkoxy group —$OR^{10}$, $R^{10}$ preferably represents $C_{6-10}$aryl$C_{1-6}$alkyl (such as benzyl, chlorobenzyl, fluorobenzyl and methoxybenzyl), heteroaryl$C_{1-6}$alkyl (such as pyridylmethyl and pyridylethyl), $C_{1-6}$alkyl (such as methyl), or $C_{1-6}$alkyl which is substituted with —$OR^{11}$ or with —$N(R^{11})_2$, especially an ethyl group substituted in the 2-position with —OAr or with —$N(R^{11})_2$ where the $R^{11}$ groups optionally complete a heterocyclic ring. Examples of substituted ethoxy groups represented by $R^4$ include phenoxyethoxy, 4-chlorophenoxyethoxy, 4-fluorophenoxyethoxy, imidazol-1-ylethoxy, pyridin-2-ylethoxy and —$OCH_2CH_2$—$N(R^{11})_2$ in which —$N(R^{11})_2$ represents morpholin-4-yl, 4-acetylpiperazin-1-yl, 4-trifluoromethylpiperidin-1-yl, N-(thiophene-2-ylmethyl)amino, N-(pyridin-3-ylmethyl)amino, 2-oxopyrrolidin-1-yl, 2-oxoimidazolin-1-yl or 3-oxo-4-phenylpiperazin-1-yl.

Typical examples of $C_{6-10}$aryl$C_{2-6}$alkenyl groups represented by $R^4$ include 4-phenylbut-1-enyl, styryl, 4-methoxystyryl, 4-fluorostyryl, 4-chlorostyryl and 4-bromostyryl.

Typical examples of heteroaryl$C_{2-6}$alkenyl groups represented by $R^4$ include 3-(imidazol-1-yl)propenyl and 3-(1,2,4-triazol-1-yl)propenyl.

Typical examples of alkenyl and substituted alkenyl groups represented by $R^4$ include, vinyl, cyanovinyl, 3-hydroxypropenyl, methoxycarbonylethenyl, benzoylethenyl and 3-[4-methyl-1,2,4-triazol-5-ylthio]propenyl.

A special class of alkenyl groups represented by $R^4$ have the formula —CH=CHCH$_2$N(R$^{16}$)$_2$. In this context, typical embodiments of —N(R$^{16}$)$_2$ include N,N-dimethylamino, piperidin-1-yl, morpholin-4-yl, 4-methylpiperazin-1-yl, 4-phenylpiperazin-1-yl and N-(2-methoxyethyl)-N-methylamino. Further examples include 4-trifluoromethylpiperidin-1-yl, 4,4-difluoropiperidin-1-yl, 5-aza-2-oxabicyclo[2.2.1]hept-5-yl, 1,2,3,6-tetrahydropyridin-1-yl, N-furfurylamino, N-(indan-1-yl)amino, N-(pyridin-2-ylmethyl)amino, N,N-bis(2-methoxyethyl)amino, 3,3-difluoropyrrolidin-1-yl, 4-hydroxy-4-trifluoromethylpiperidin-1-yl, 3-oxopiperazin-1-yl, 3-oxo-4-cyclohexylpiperazin-1-yl, 3-oxo-4-phenylpiperazin-1-yl, 4-methylpiperidin-1-yl, N-(2,2,2-trifluoroethyl)amino, N-(thiophene-2-ylmethyl)amino, N-methyl-N-(tetrahydrofuran-3-ylmethyl)amino, 2-phenoxymethylmorpholin-4-yl, 3-(pyridin-3-yl)-pyrrolidin-1-yl, N-(4-phenylmorpholin-2-ylmethyl)amino, N-(tetrahydropyran-2-ylmethyl)amino, N-(tetrahydrofuran-3-yl)amino, 3-hydroxypiperidin-1-yl, N-methyl-N-(tetrahydropyran-4-yl)amino, N-(dioxan-2-ylmethyl)amino and N-(tetrahydropyran-4-yl)amino.

Typical examples of substituted acetamido groups represented by —NHCOCH$_2$(NR$^{16}$)$_2$ include 2-(diethylamino)acetamido, 2-(N-benzyl-N-methylamino)acetamido, 2-(pyrrolidin-1-yl)acetamido, 2-[4-(4-fluorophenyl)piperazin-1-yl]acetamido, 2-[5-(4-fluorophenyl)-2,5-diazabicyclo[2.2.1]hept-2-yl]acetamido, 2-(4-phenylpiperazin-1-yl)acetamido, 2-(piperidin-1-yl)acetamido, 2-(4-methylpiperazin-1-yl)acetamido, 2-(morpholin-4-yl)acetamido, 2-(4-phenylpiperidin-1-yl)acetamido, 2-[4-(2-methoxyphenyl)piperidin-1-yl]acetamido, 2-(2-phenoxymethylmorpholin-4-yl)acetamido, 2-[(4-phenylmorpholin-2-ylmethyl)amino]acetamido, 2-(3-phenyl-5,6-dihydro-8H-imidazo[1,2-α]pyrazin-7-yl)acetamido and 2-[4-(2-methoxyphenyl)piperazin-1-yl] acetamido.

Typical examples of substituted acetamido groups represented by —NHCOCH$_2$OR$^{10}$ include 2-methoxyacetamido, 2-phenoxyacetamido, and the corresponding 2-, 3- and 4-fluorophenoxy derivatives and 2-, 3- and 4-chlorophenoxy derivatives.

Typical examples of substituted methyl groups represented by —CH$_2$OR$^9$ include hydroxymethyl, phenoxymethyl, 2-, 3- and 4-chlorophenoxymethyl, 2-, 3- and 4-fluorophenoxymethyl, 2-, 3- and 4-methoxyphenoxymethyl, 4-trifluoromethylphenoxymethyl, 4-t-butylphenoxymethyl, 4-[1,2,4]triazol-1-ylphenoxymethyl, quinolin-5-yloxymethyl, 4-trifluoromethoxyphenoxymethyl and 4-(4-acetylpiperazin-1-yl)phenoxymethyl.

Typical examples of other substituted C$_{1-6}$alkyl groups represented by R$^4$ include 3-(morpholin-4-yl)propyl, 3-(4-trifluoromethylpiperidin-1-yl_propyl, morpholin-4-ylmethyl, 2-carboxyethyl and 2-methoxycarbonylethyl.

A subclass of the compounds of formula I is defined by formula I(A):

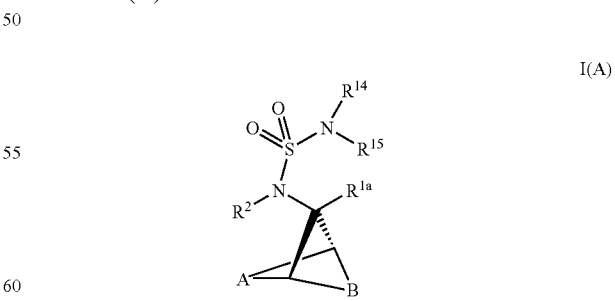

I(A)

wherein R$^{1a}$ represents H, C$_{1-4}$alkyl or C$_{2-4}$alkenyl; R$^{15a}$ represents H or C$_{1-6}$alkyl; and A, B, R$^1$, R$^2$ and R$^{14}$ have the same meanings as before.

A preferred subset of the compounds of formula I(A) is defined by formula I(B):

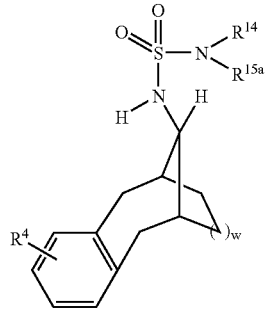

wherein w, $R^4$, $R^{14}$ and $R^{15a}$ have the same meanings as before.

Examples of acyclic sulfamates in accordance with formula I(A) include:

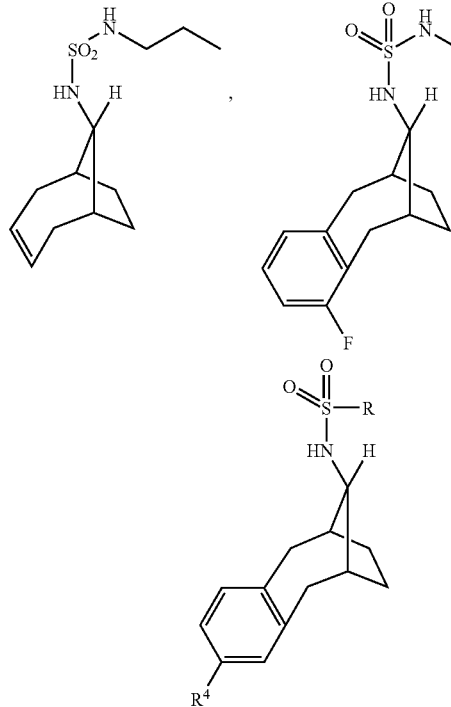

where R and $R^4$ are as indicated below:

| R | $R^4$ |
|---|---|
| dimethylamino | H |
| n-propylamino | H |
| cyclopentylamino | H |
| 2-hydroxycyclopentylamino | H |
| methylamino | H |
| ethylamino | H |
| isopropylamino | H |
| t-butylamino | H |
| n-butylamino | H |
| propargylamino | H |
| allylamino | H |

-continued

| R | $R^4$ |
|---|---|
| sec-butylamino | H |
| 2-methoxyethylamino | H |
| cyclopropylamino | H |
| cyclobutylamino | H |
| cyclohexylamino | H |
| 2,2,2-trifluoroethylamino | H |
| n-propylamino | 4-F-C6H4-O-CH2-C(O)-NH- |
| t-butylamino | 4-F-C6H4-O-CH2-C(O)-NH- |
| n-propylamino | 2,4-Cl2-C6H3-O-CH(Me)-C(O)-NH- |
| cyclobutylamino | 4-F-C6H4-O-CH2CH2-O-Me |
| cyclobutylamino | morpholino-CH2-CH=CH-Me |
| cyclobutylamino | PhCH2O— |
| 2,2,2-trifluoroethylamino | PhCH2O— |
| cyclobutylamino | morpholino-CH2CH2-O-Me |
| cyclobutylamino | morpholino-CH2CH2CH2CH3 |
| 2,2,2-trifluoroethylamino | morpholino-CH2CH2-O-Me |
| 2,2,2-trifluoroethylamino | morpholino-CH2-CH=CH-Me |
| 2,2,2-trifluoroethylamino | MeOCO— |
| 2,2,2-trifluoroethylamino | 2-(4-F-C6H4)-5-methyl-1,3,4-oxadiazole |
| 2,2,2-trifluoroethylamino | 2-phenyl-5-methyl-1,3,4-oxadiazole |
| 2,2,2-trifluoroethylamino | 4-(CF3)-piperidine-N-CH2-CH=CH-Me |

| R | R⁴ |
|---|---|
| 2,2,2-trifluoroethylamino | 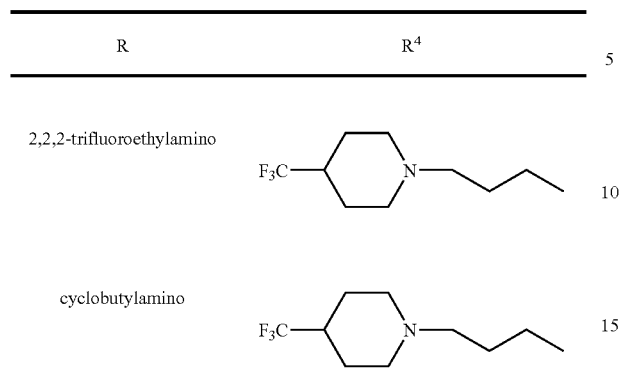 |
| cyclobutylamino | |

Another subclass of the compounds of formula I is defined by formula I(C):

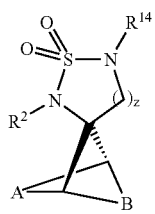

I(C)

wherein z is 1, 2 or 3; and A, B, $R^2$ and $R^{14}$ have the same meanings as before.

Preferably, z is 1 or 2, and most preferably z is 1.

A preferred subset of the compounds of formula I(C) is defined by formula I(D):

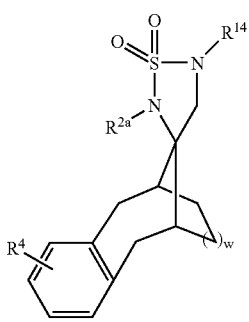

I(D)

wherein:

$R^{2a}$ represents H or $C_{2-6}$acyl which is optionally substituted with a carboxylic acid group or with an amino group; and w, $R^4$ and $R^{14}$ have the same meanings as before.

In formula I(D), w is preferably 1 and $R^{2a}$ is preferably H.

Examples of cyclic sulfamates in accordance with formula I(C) include:

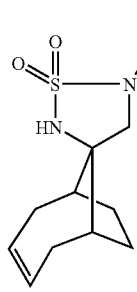

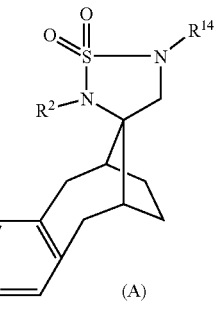

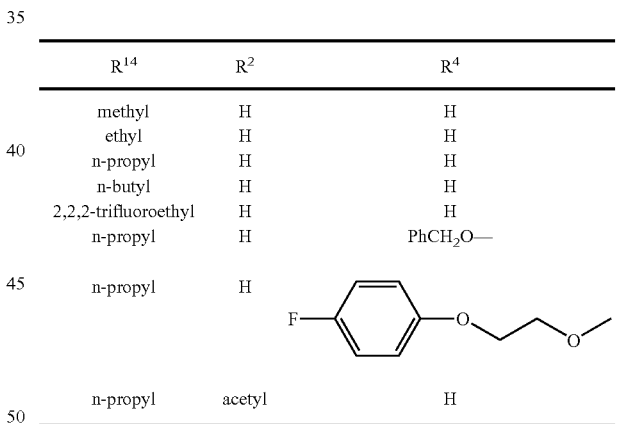

(A)

where $R^{14}$, $R^2$ and $R^4$ in (A) are as follows:

| $R^{14}$ | $R^2$ | $R^4$ |
|---|---|---|
| methyl | H | H |
| ethyl | H | H |
| n-propyl | H | H |
| n-butyl | H | H |
| 2,2,2-trifluoroethyl | H | H |
| n-propyl | H | PhCH₂O— |
| n-propyl | H | F-⟨phenyl⟩-O-CH₂CH₂-O-CH₃ |
| n-propyl | acetyl | H |

In further examples of embodiment (A), $R^2$ and $R^4$ are both H and $R^{14}$ is isopropyl, 2-methylpropyl, 2-fluoroethyl, cyclopropylmethyl, cyclobutylmethyl, cyclopentylmethyl, cyclohexylmethyl, cyclobutyl or cyclopentyl.

In further examples of embodiment (A), $R^2$ is H, $R^4$ is PhCH₂O—, and $R^{14}$ is cyclobutylmethyl, 2,2,2-trifluoroethyl, phenyl, benzyl, 3,4-difluorobenzyl, 2,5-difluorobenzyl or 4-chlorobenzyl.

In further examples of embodiment (A), $R^2$ is H, $R^{14}$ is n-propyl, and $R^4$ is 3-pyridyl, (pyridin-3-yl)methoxy, —CO₂Me, 2-(pyridin-2-yl)ethoxy, 3-(morpholin-4-yl)propyl, —CH₂OH, —CHO, —CH═CHCO₂Me, 3-[(4-methyl-1,2,4-triazol-3-yl)thio]prop-1-enyl, —CN, 5-(4-fluorophenyl)oxazol-2-yl, 5-(4-fluorophenyl)-1,3,4-oxadiazol-2-yl, 3-(pyridin-2-yl)-1,2,4-oxadiazol-5-yl, 3-pyrazinyl-1,2,4-oxadiazol-5-yl, —CH═CHCH$_2$OH, or 5-(4-fluorophenyl)pyrazol-3-yl.

In further examples of embodiment (A), R$^2$ is H, R$^{14}$ is n-propyl, and R$^4$ is —CH═CHCH$_2$N(R$^{16}$)$_2$ where —N(R$^{16}$)$_2$ is morpholin-4-yl, 4-trifluoromethylpiperidin-1-yl, 4,4-difluoropiperidin-1-yl, 4-carbamoylpiperidin-1-yl, 4-ethoxycarbonylpiperidin-1-yl, 4-carboxypiperidin-1-yl, 4-hydroxypiperidin-1-yl, 1,2,3,6-tetrahydropyridinyl, 5-aza-2-oxabicyclo[2.2.1]hept-1-yl, N-[(furan-2-yl)methyl]amino, N,N-bis(2-methoxyethyl)amino, N-(indan-1-yl)amino, or N-[(pyridin-2-yl)methyl]amino.

In further examples of embodiment (A), R$^2$ is H, R$^{14}$ is n-propyl, and R$^4$ is —OCH$_2$CH$_2$N(R$^{11}$)$_2$ where —N(R$^{11}$)$_2$ is morpholin-4-yl, or 2-oxo-imidazolin-1-yl.

In further examples of embodiment (A), R$^2$ is H, R$^{14}$ is 2,2,2-trifluoroethyl and R$^4$ is —OH, —CO$_2$Me, —CH$_2$OH, —CHO, —CO$_2$H, —CH═CHCO$_2$Me, —CH═CHCO$_2$H, —CH═CHCH$_2$OH, —CH═N—OH, —CH═N—OEt, —CH$_2$CH$_2$CO$_2$Me, —CH$_2$CH$_2$CO$_2$H, (morpholin-4-yl)methyl, 2-(imidazol-1-yl)ethoxy, 3-(4-trifluoromethylpiperidin-1-yl)propyl, —CH═N—OCH$_2$Ph, —CH═N—OCH$_2$(4-F—C$_6$H$_4$), —CH═N—OCH$_2$(4-CF$_3$—C$_6$H$_4$), 3-pyrazinyl-1,2,4-oxadiazol-5-yl, 3-(4-fluorophenyl)-1,2,4-oxadiazol-5-yl, 3-(pyridin-2-yl)-1,2,4-oxadiazol-5-yl, —CH═N—OCH$_2$(2-F—C$_6$H$_4$), —CH═N—OCH$_2$CH═CH$_2$, —CH═N—OCH$_2$(3-F—C$_6$H$_4$), or —CH═N—OCH$_2$(2,4-di-C—C$_6$H$_3$).

In further examples of embodiment (A), R$^2$ is H, R$^{14}$ is 2,2,2-trifluoroethyl and R$^4$ is —CH═CHCH$_2$N(R$^{16}$)$_2$ where —N(R$^{16}$)$_2$ is morpholin-4-yl, 4-trifluoromethylpiperidin-1-yl, 5-aza-2-oxabicyclo[2.2.1]hept-1-yl, 4,4-difluoropiperidin-1-yl, 4-hydroxy-4-trifluoromethylpiperidin-1-yl, 4-methylpiperidin-1-yl, 3-oxo-4-phenylpiperazin-1-yl, 3-oxo-4-cyclohexylpiperazin-1-yl, 3-oxo-piperazin-1-yl, N-(tetrahydrofuran-3-yl)amino, N-methyl-N-(tetrahydrofuran-3-yl)amino, N-(tetrahydropyran-4-yl)amino, N-methyl-N-(tetrahydropyran-4-yl)amino, N-(dioxanylmethyl)amino, N-[(tetrahydropyran-2-yl)methyl]amino, 3-hydroxypiperidin-1-yl, 5-aza-2-oxabicyclo[5.4.0]undeca-7,9,11-trien-5-yl, 2-(phenoxymethyl)morpholin-4-yl, N-[(4-phenylmorpholin-2-yl)methyl]amino, 3,3-difluoropyrrolidin-1-yl, N-(2,2,2-trifluoroethyl)amino, or 3-(pyridin-3-yl)pyrrolidin-1-yl.

In further examples of embodiment (A), R$^2$ is H, R$^{14}$ is 2,2,2-trifluoroethyl and R$^4$ is —OCH$_2$CH$_2$N(R$^{11}$)$_2$ where N(R$^{11}$)$_2$ is morpholin-1-yl, 4-acetylpiperazin-1-yl, N-(2-methoxyethyl)amino, N-[(thiophen-2-yl)methyl]amino, N-[(pyridin-3-yl)methyl]amino, N-(methoxycarbonylmethyl)amino, 3-oxo-4-phenylpiperazin-1-yl, or 4-trifluoromethypiperidin-1-yl.

Further examples of individual compounds in accordance with formula I(C) appear in the Examples appended hereto.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

Acyclic sulfamides of formula I(A) in which R$^{1a}$ and R$^2$ are both H may be prepared by reaction of the amines VI with sulfamoyl halides R$^{14}$(R$^{15a}$)N—SO$_2$-Hal

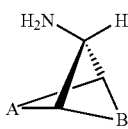

VI where Hal represents halogen (especially Cl) and A, B, $R^{14}$, and $R^{15a}$ have the same meanings as before. The reaction is advantageously carried out in an aprotic solvent such as dichloromethane in the presence of a base such as pyridine at ambient temperature.

The amines VI may be prepared by reduction of the oximes VII, derived from the ketones VIII:

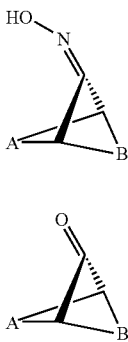

VII

VIII wherein A and B have the same meanings as before.

The reduction of VII to VI may be effected by conventional means, such as hydrogenation in a solvent such as acetic acid in the presence of a catalyst such as $PtO_2$, or treatment with sodium cyanoborohydride in alcoholic solution followed by Zn/acetic acid reduction of the resulting hydroxylamine. Conversion of the ketones VIII to the oximes VII is readily achieved by condensation of the ketones with hydroxylamine hydrochloride in refluxing ethanolic solution in the presence of a mild base such as sodium acetate.

Alternatively, the acyclic sulfamides of formula I(A) wherein $R^{1a}$ and $R^2$ are both H may be prepared by reaction of the amines $R^{14}(R^{15a})NH$ with sulfamate esters VA, or by reaction of amines VI with sulfamate esters VB:

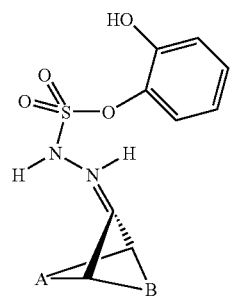

VA

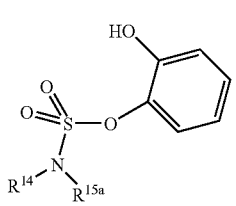

VB where A, B, $R^{14}$ and $R^{15a}$ have the same meanings as before. The reaction is typically carried out using excess of the amine in dioxan at 80° C. under nitrogen in a sealed tube.

The sulfamate esters VA and VB are prepared by treatment of catechol sulfate with amines VI or $R^{14}(R^{15a})NH$ respectively at ambient temperature in an aprotic solvent in the presence of a tertiary amine catalyst.

Compounds of formula I(A) in which $R^{1a}$ is an alkyl or alkenyl group and $R^2$ is H may be prepared by reaction of the sulphamylimine IX with RLi:

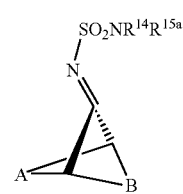

IX wherein R represents $C_{1-4}$alkyl or $C_{2-4}$alkenyl, and A, B, $R^{14}$ and $R^{15a}$ have the same meanings as before. The reaction is advantageously carried out at reduced temperature in a hydrocarbon solvent, with quenching by aqueous acid.

The sulphamylimines IX are obtained by condensation of the ketones VIII with a sulphamide $R^{14}(R^{15a})N$—$SO_2$—$NH_2$, where $R^{14}$ and $R^{15a}$ have the same meaning as before. The condensation may be effected by refluxing the reagents in toluene in the presence of an acid catalyst with azeotropic removal of water.

Cyclic sulfamides of formula I(C) in which $R^2$ is H may be prepared by reaction of the diamines XIV with sulfamide ($H_2NSO_2NH_2$), optionally followed (when $R^{14}$ in XIV is H) by N-alkylation with $R^{14b}$-L where $R^{14b}$ is $R^{14}$ which is other than H, L is a leaving group (especially bromide or iodide) and A, B and z have the same meanings as before:

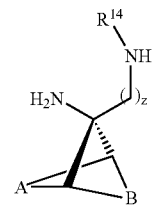

XIV

The reaction of the diamine with sulfamide is typically carried out in refluxing anhydrous pyridine, and alkylation of the product may be effected by treatment thereof with a strong base such as lithium bis(trimethylsilyl)amide in anhydrous THF at 0° C. followed by reaction with $R^{14b}$-L at ambient temperature.

Diamines XIV in which $R^{14}$ is H are available by the reduction of nitriles XIII:

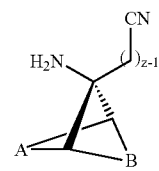

XIII where A, B and z have the same meanings as before. The reduction is typically carried out using lithium aluminium hydride at 0° C. under nitrogen under anhydrous conditions in an aprotic solvent such as THF.

Nitriles XIII in which z is 1 are obtained by reaction of ketones VIII with potassium cyanide and ammonium chloride, typically at ambient temperature in aqueous dioxan. Nitriles XIII in which z is 2 or 3 are obtainable from the corresponding nitrites XIII in which z is 1 by standard methods of homologation (e.g. hydrolysis to the corresponding carboxylic acid, followed by esterification with a lower alcohol, reduction to the primary alcohol, conversion to the tosylate and displacement by cyanide.)

An alternative route to diamines XIV in which z is 1 involves reaction of a t-butylsulphonyl-aziridine XIX with $R^{14}NH_2$, followed by cleavage of the t-butylsulphonyl group:

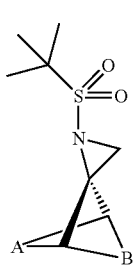

XIX where A, B and $R^{14}$ have the same meanings as before. Ring-opening of the aziridine is typically effected by heating at 100° C. with $R^{14}NH_2$ in DMF solution in a sealed tube, while cleavage of the t-butylsulphonyl group may be sffected by treatment with trifluoromethanesulphonic acid at 0° C.

The aziridines IX are available by reaction of the sulphonylimines XX with trimethylsulphoxonium iodide in the presence of sodium hydride:

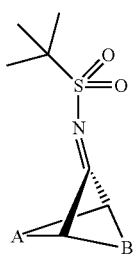

XX where A and B have the same meanings as before. The reaction may be carried out at ambient temperature in a THF-DMSO mixture.

The sulphonylimines XX are available form the condensation of ketones VIII with t-butylsulphonamide, the reaction taking place in refluxing dichloromethane in the presence of titanium (IV) chloride and triethylamine.

An alternative route to the diamines XIV in which z is 2 involves reaction of nitrites XIII (z=1) with allylmagnesium bromide to form alkenes XXI, followed by ozonolysis to give the aldehydes XXII, which are subsequently used to reductively alkylate an amine $R^{14}NH_2$:

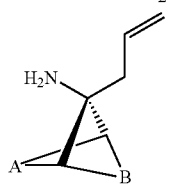

XXI

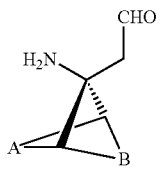

XXII where A, B and $R^{14}$ have the same meanings as before. The nitrite displacement may be carried out in THF/ether at ambient temperature, while the ozonolysis is advantageously carried out at low temperature (e.g. −80° C.). The resulting aldehydes XXII may reacted in situ with $R^{14}NH_2$ and then sodium triacetoxyborohydride to provide the relevant diamines.

Compounds of formula I in which $R^2$ is other than H may be obtained by appropriate transformations of the compounds of formulae I(A) and I(C) in which $R^2$ is H, for example by N-alkylation or N-acylation using standard methods. Alternatively, the primary amines VI may be converted to secondary amines by N-alkylation or N-arylation using standard methods, prior to reaction with $R^{14}(R^{15a})N$—$SO_2$-Hal.

The ketones VIII, sulphamoyl halides $R^{14}(R^{15a})N$—$SO_2$-Hal and sulphamides $R^{14}(R^{15a})N$—$SO_2$—$NH_2$ are commercially available or accessible by the application of known synthetic methods to commercially available materials. For example, a convenient route to ketones VIIIA, synthetic precursors of the compounds of formula IV, is illustrated in the following scheme:

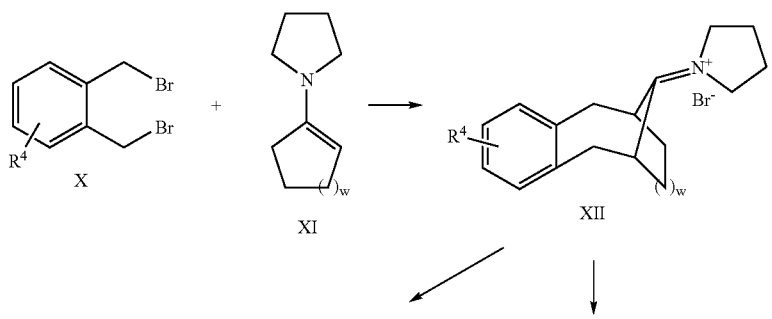

-continued

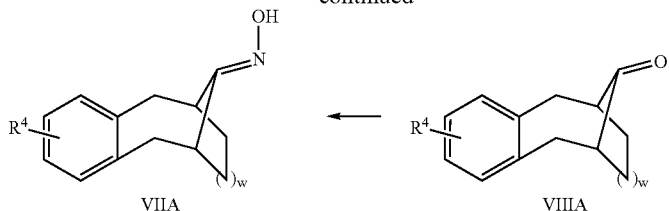

wherein w and $R^4$ have the same meanings as before.

The dibromide X reacts exothermically with the enamine XI in acetonitrile solution to form the salt XII, which may be hydrolysed in aqueous acid to form the ketone VIIIA, which may be converted to the oxime VIIA in the manner described previously. Alternatively, the salt XII may be reacted directly with hydroxylamine hydrochloride under similar conditions to provide oxime VIIA. Although the above illustration is with regard to monosubstituted benzo-fused derivatives, the process may readily be adapted to provide ketones of formula VIII in which A comprises a different fused ring system.

Individual compounds in accordance with formula I may be converted to different compounds in accordance with formula I by application of known synthetic techniques. Alternatively, such transformations may be carried out on the precursors of the compounds of formula I. For example, a compound in which A or B comprises an olefinic double bond may be converted to the corresponding alkane derivative by catalytic hydrogenation. Similarly, an exocyclic olefinic double bond may be converted to an oxo substituent by ozonolysis. Alternatively, an oxo substituent on A or B may be converted to an exocyclic olefin by means of a Wittig reaction, or an oxo substituent may be converted to a thioxo substituent by treatment with Lawesson's reagent.

Compounds of formula I wherein A or B comprises a —$CH_2$—$NR^{13}$— moiety may be prepared from the corresponding compounds comprising a —CO— moiety as illustrated in the scheme below:

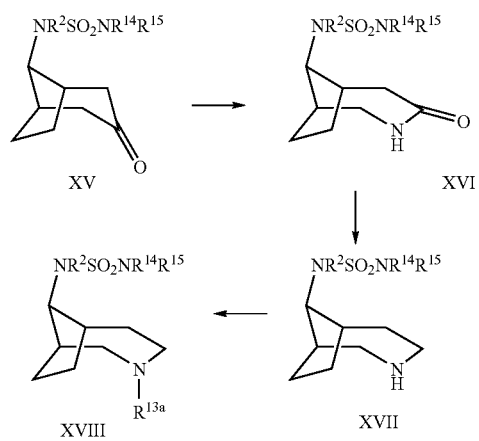

Treatment of ketone XV with hydroxylamine-O-sulfonic acid in refluxing formic acid yields the lactam XVI, which may be reduced to the amine XVII by reaction with aluminium hydride in refluxing THF. If desired, N-alkylation may be carried out by standard methods to provide XVIII where $R^{13a}$ is $R^{13}$ which is other than H and $R^{13}$ has the same meaning as before.

Likewise, compounds of formula I or their precursors comprising aryl or heteroaryl groups may have substituents attached thereto by conventional synthetic means, and said substituents may be converted to other substituents by known techniques.

As an illustration of this principle, compounds of formula IV in which $R^4$ is H may be nitrated under standard conditions (such as reaction with sodium nitrate in trifluoroacetic acid) to provide the nitro derivatives (IV, $R^4$=$NO_2$). Generally, a mixture of positional isomers is obtained, from which the individual isomers may be separated by conventional techniques of chromatography or fractional crystallisation. The nitro derivatives may be reduced to the corresponding anilines (IV, $R^4$=$NH_2$) by conventional methods, such as reaction with tin in hydrochloric acid. The anilines may be converted to the corresponding diazonium salts (e.g. by treatment with sodium nitrite and hydrochloric acid) and thence to a variety of derivatives by displacement of the diazonium group. Examples of substituents $R^4$ introducible by this route include F, Cl, Br, I, OH, CN and SH. A phenol group introduced by this process may be alkylated by standard procedures, for example by reaction with an alkyl halide (such as a phenoxyethyl bromide) in the presence of a base such as potassium carbonate. Such a reaction may be carried out at about 120° C. in DMF. An alternative alkylation method is a Mitsunobu reaction with an alcohol (e.g. $(R^{11})_2NCH_2CH_2OH$ where $R^{11}$ has the same meaning as before) in the presence of diethyl azodicarboxylate and triphenylphosphine.

Alternatively, the anilines IV ($R^4$=$NH_2$) may be reacted with $R^{10}$CO-Hal, $R^{10}$OCO-Hal or $R^{10}SO_2$-Hal to form the corresponding amides ($R^4$=—$NHCOR^{10}$), carbamates ($R^4$=—$NHCO_2R^{10}$) or sulphonamides ($R^4$=—$NHSO_2R^{10}$) respectively, where Hal and $R^{10}$ have the same meanings as before. In another alternative, the anilines may be alkylated, e.g. by reaction with $R^{10}$CHO and sodium cyanoborohydride to form IV ($R^4$=—$NHCH_2R^{10}$) where $R^{10}$ has the same meaning as before.

The bromo derivatives IV ($R^4$=Br) may be subjected to substitution by $R^9R^{10}$NH to form secondary or tertiary amines IV ($R^4$=—$NR^9R^{10}$), where $R^9$ and $R^{10}$ have the same meanings as before. The reaction may be carried out at elevated temperature in a sealed tube in the presence of a $Pd^0$ catalyst. In the case of secondary amines thus formed (i.e. if $R^9$ is hydrogen), subsequent reaction with $R^{10}$ CO-Hal, $R^{10}$OCO-Hal or $R^{10}SO_2$-Hal provides the corresponding amides, carbamate and sulphonamides respectively, where $R^{10}$ and Hal have the same meanings as before.

Alternatively, the bromo derivatives IV ($R^4$=Br) may react with boronic acids $R^{10}B(OH)_2$ (or esters thereof) to form IV ($R^4$=$R^{10}$), where $R^{10}$ has the same meaning as before, the reaction taking place in the presence of base and a $(Ph_3P)_4Pd^0$ catalyst.

Compounds of formula IV (or their precursors) in which $R^4$ is alkoxycarbonyl (available by elaboration of the compounds X in which $R^4$ is alkoxycarbonyl as described above) are particularly useful intermediates. Reduction of the alkoxycarbonyl group (e.g. by treatment with diisobutylaluminium hydride [DIBAL-H]) provides the corresponding benzyl alcohol ($R^4$=—$CH_2OH$), which may be converted to the tosylate, mesylate or similar, or to the corresponding bromide, and then subjected to nucleophilic displacement by an amine or ArO— where Ar has the same meaning as before, especially by a phenoxide. Alternatively, the benzyl alcohol may be oxidised to the corresponding aldehyde ($R^4$=—CHO) (e.g. by treatment with pyridinium dichromate at room temperature in dichloromethane), and then coupled with a variety of ylides to form olefinic derivatives, including propenoic acid derivatives ($R^4$=—CH=$CHCO_2R$ where R is alkyl such as methyl or ethyl). Reduction of the propenoic esters (e.g. by treatment with DIBAL-H) provides the corresponding allyl alcohols ($R^4$=—CH=$CHCH_2OH$ which may be elaborated in the same way as the benzyl alcohols discussed above. In particular, the alcohol may be converted to the corresponding bromide ($R^4$=—CH=$CHCH_2Br$) by treatment with phosphorus tribromide in dichloromethane at low temperature (e.g. −20° C.), and the bromine atom may be displaced by a variety of nucleophiles, in particular the amines $NH(R^{16})_2$ such as optionally substituted N-heterocycles, thereby providing the corresponding compounds in which $R^4$ is —CH=$CHCH_2N(R^{16})_2$ where $R^{16}$ has the same meaning as before. The displacement is typically carried out at about 80° C. in DMF in the presence of potassium carbonate.

Hydrogenation of the above-mentioned propenyl esters and amines (e.g. over a Pt or Pd catalyst) provides the corresponding saturated derivatives.

The above mentioned aldehydes ($R^4$=—CHO) may also be reacted with $R^{11}O$—$NH_2$ in the presence of weak base to provide the corresponding oximes and alkoximes ($R^4$=—CH=N—$OR^{11}$). Alternatively, the aldehydes may be treated with hydroxylamine hydrochloride in refluxing formic acid to provide the corresponding nitriles ($R^4$=—CN), which in turn may be reacted with hydroxylamine hydrochloride and triethylamine in refluxing ethanol to provided the corresponding carboxamidoximes ($R^4$=—$C(NH_2)$=NOH), which may be condensed with $ArCO_2H$ to yield the corresponding compounds in which $R^4$ is 5-Ar-1,2,4-oxadiazol-3-yl, where Ar has the same meaning as before.

The aforementioned esters ($R^4$=alkoxycarbonyl) may also be hydrolysed to the corresponding acids ($R^4$=—$CO_2H$). The resulting carboxylic acid group provides access to a variety of heteroaryl derivatives ($R^4$=heteroaryl) via conventional synthetic routes. For example, reaction of the acids with $ArCONHNH_2$ provides 5-Ar-1,3,4-oxadiazol-2-yl derivatives; reaction of the acids with Ar—$C(NH_2)$=NOH provides 3-Ar-1,2,4-oxadiazol-5-yl derivatives; reaction of the acids with $ArCOCH_2NH_2$ provides 5-Ar-oxazol-2-yl derivatives; and condensation of the acids with $ArCOCH_3$, followed by treatment with hydrazine, provides 5-Ar-1H-pyrazol-3-yl derivatives, where Ar has the same meaning as before.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 µL in minimal essential medium (MEM) (phenol red-free)+ 10% foetal bovine serum (FBS), 50 mM HEPES buffer (pH 7.3), 1% glutamine, 0.2 mg/ml G418 antibiotic, 10 mM sodium butyrate.

(3) Make dilutions of the compound plate. Dilute stock solution to 5.5% DMSO/110 µM compound. Mix compounds vigorously and store at 4° C. until use.

(4) Add 10 µL compound/well. Mix plate briefly, and leave for 18 h in 37° C. incubator.

(5) Remove 90 µL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.

(6) Add back 100 µL of warm MEM+10% FBS, 50 mM HEPES (pH 7.3), 1% glutamine, 0.2 mg/ml G418, 10 mM sodium butyrate to each well, and return plate to 37° C. incubator.

(7) Prepare reagents necessary to determine amyloid peptide levels, for example by ELISA assay.

(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 µL/well MTS/PES solution to the cells; mix and leave at 37° C.

(11) Read plate when the absorbance values are approximately 1.0 (mix briefly before reading to disperse the reduced formazan product).

Alternative assays are described in *Biochemistry*, 2000, 39(30), 8698–8704.

The Examples of the present invention all had an $ED_{50}$ of less than 10 µM, preferably less than 1 µM and most preferably less than 100 nM in at least one of the above assays.

The following examples illustrate the present invention.

EXAMPLES

Example 1

[N'-(11-endo)]-N'-(5,6,7,8,9,10-hexahydro-6,9-methanobenzo[a][8]annulen-11-yl)-N,N-dimethylsulfamide

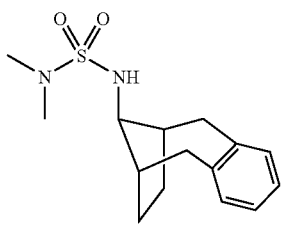

Dimethylsulfamoyl chloride (110 μL, 1.0 mmol) was added to a stirred solution of [11-endo]-5,6,7,8,9,10-hexahydro-6,9-methanobenzo[a][8]annulen-11-amine (J. Org. Chem. 1982, 47, 4329) (150 mg, 0.8 mmol) and triethylamine (225 μL, 1.6 mmol) in dry DCM (3 mL) at room temperature under nitrogen. The reaction was stirred at room temperature overnight before being partitioned between DCM and saturated aqueous sodium hydrogen carbonate. The aqueous layer was further extracted with DCM (x2). The combined organic extracts were dried ($Na_2SO_4$), filtered and evaporated. The residue was purified by chromatography on silica gel eluting with 20% ethyl acetate/hexanes to give the title sulfamide (60 mg, 25%) as a cream solid, δ ($^1H$, 360 MHz, $CDCl_3$) 1.16–1.22 (2H, m), 1.68–1.72 (2H, m), 2.45–2.51 (2H, m), 2.65 (2H, dd, J=16.1, 7.6), 2.85 (6H, s), 3.09 (2H, d, J=16.1), 3.76–3.81 (1H, m), 4.57 (br d, J=10), 7.09 (4H, br s).

Examples 2–16

Intermediate 1: [11-endo]-2-hydroxyphenyl 5,6,7,8,9,10-hexahydro-6,9-methanobenzo[a][8]annulen-11-ylsulfamate

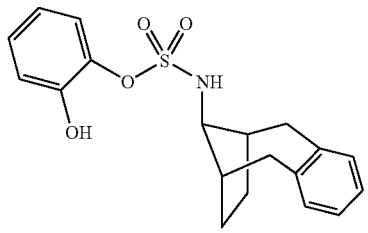

Catechol sulfate (Synth. Commun. 1994, 24, 1631) (970 mg, 5.6 mmol) was added in one portion to a stirred solution of [11-endo]-5,6,7,8,9,10-hexahydro-6,9-methanobenzo[a][8]annulen-11-amine (1.0 g, 5.3 mmol) in dry tetrahydrofuran (10 mL) at 0° C. under nitrogen. After two hours at 0° C. the cooling bath was removed and the reaction was allowed to warm to room temperature. After stirring at room temperature overnight the reaction mixture was partitioned between ethyl acetate and saturated aqueous ammonium chloride. The aqueous layer was further extracted with ethyl acetate (x2). The combined organic extracts were dried ($Na_2SO_4$), filtered and evaporated. The residue was purified by chromatography on silica gel eluting with 2% to 4% ethyl acetate/DCM to give the title sulfamate (1.3 g, 68%) as a colourless solid, δ ($^1H$, 360 MHz, $CDCl_3$) 1.18–1.26 (2H, m), 1.68–1.75 (2H, m), 2.50–2.58 (2H, m), 2.65 (2H, dd, J=16.2, 7.5), 3.03 (2H, d, J=16.1), 4.00–4.13 (1H, m), 5.28 (1H, br d, J=8.5), 6.25 (1H, s), 6.93 (1H, td, J=7.8, 1.5), 7.05–7.12 (4H, m), 7.20 (1H, br t, J=7.8), 7.24–7.28 (2H, m).

General procedure: (J. Org. Chem. 1980, 45, 5371 and 5373)

A solution of Intermediate 1 (1eq) and the appropriate amine (3eq) in dry dioxan (7 mL/mmol) was heated at 80° C. in a sealed tube for one hour. After cooling to room temperature the reaction mixture was diluted with DCM, then washed with 2N aqueous sodium hydroxide. The aqueous layer was extracted with DCM (x2). The combined organic extracts were dried ($Na_2SO_4$), filtered and evaporated. The residue was purified by chromatography on silica gel eluting with ethyl acetate/DCM mixtures as appropriate to give the corresponding sulfamide By this procedure, the products of Examples 2–16 were obtained.

Example 2

[N-(11-endo)]-N-(5,6,7,8,9,10-hexahydro-6,9-methanobenzo[a][8]annulen-11-yl)-N'-propylsulfamide

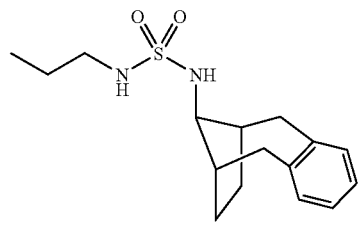

Colourless solid (88%), δ ($^1H$, 360 MHz, $CDCl_3$) 0.98 (3H, t, J=7.5), 1.17–1.23 (2H, m), 1.59–1.72 (4H, m), 2.47–2.54 (2H, m), 2.64 (2H, dd, J=16.0, 7.6), 3.04–3.12 (4H, m), 3.75–3.81 (1H, m), 4.14–4.18 (1H, m), 4.65 (1H, br d, J=8), 7.09 (4H, br s); MS (ES+) 309 ([MH]$^+$).

Example 3

[N'-(11-endo)]-N-cyclopentyl-N'-(5,6,7,8,9,10-hexahydro-6,9-methanobenzo[a][8]annulen-11-yl)sulfamide

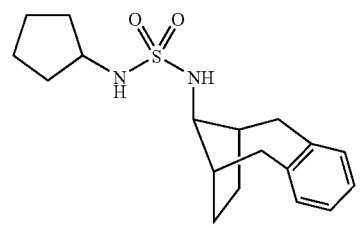

Solid (88%), δ ($^1H$, 360 MHz, $CDCl_3$) 1.16–1.23 (2H, m), 1.50–1.75 (8H, m), 1.98–2.07 (2H, m), 2.49–2.55 (2H, m), 2.64 (2H, dd, J=16.0, 7.6), 3.10 (2H, d, J=15.9), 3.73–3.80 (2H, m), 4.16 (1H, br d, J=7.5), 4.65 (1H, br d, J=8), 7.09 (4H, br s); δ ($^{13}C$, 90 MHz, $CDCl_3$) 25.1, 27.5, 35.5, 37.2, 39.7, 57.2, 61.8, 127.9, 133.4, 141.0; MS (ES+) 335 ([MH]$^+$).

Example 4

[N-(11-endo), N'-(1R/S,2R/S)]-N-(5,6,7,8,9,10-hexahydro-6,9-methanobenzo[a][8]annulen-11-yl)-N'-[2-hydroxycyclopentyl]sulfamide

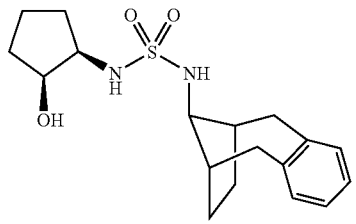

The amine was prepared as described in Tetrahedron, 1991, 47, 4941. This gave the title sulfamide (35 mg, 48%) as a colourless solid, δ ($^1$H, 360 MHz, $d_6$-DMSO) 0.91–1.02 (2H, m), 1.40–1.86 (8H, m), 2.37–2.45 (4H, m), 3.23–3.29 (2H, m), 3.35–3.41 (1H, m), 3.57–3.62 (1H, m), 3.98–4.01 (1H, m), 4.55 (1H, d, J=3.9), 6.31 (1H, d, J=7.6), 7.02–7.09 (4H, m), 7.12 (1H, d, J=6.6); δ ($^{13}$C, 90 MHz, $d_6$-DMSO) 21.8, 27.7, 30.6, 34.0, 37.1, 39.5, 59.7, 61.8, 73.4, 127.8, 133.3, 142.4; MS (ES+) 351 ([MH]$^+$).

Example 5

[N-(11-endo)]-N-(5,6,7,8,9,10-hexahydro-6,9-methanobenzo[a][8]annulen-11-yl)-N'-methylsulfamide

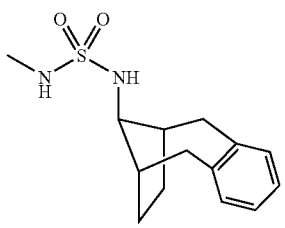

In this example tetrahydrofuran was used in place of dioxan. This gave the title sulfamide (62 mg, 80%) as a colourless solid, δ ($^1$H, 360 MHz, CDCl$_3$) 1.16–1.24 (2H, m), 1.65–1.74 (2H, m), 2.47–2.54 (2H, m), 2.64 (2H, dd, J=16.0, 7.6), 2.78 (3H, m), 3.10 (2H, d, J=15.9), 3.74–3.80 (1H, m), 4.17 (1H, br s), 4.69 (1H, br d, J=7.2), 7.09 (4H, m); δ ($^{13}$C, 90 MHz, CDCl$_3$) 27.4, 31.2, 37.1, 39.7, 61.8, 127.9, 133.3, 140.9; MS (ES+) 281 ([MH]$^+$).

Example 6

[N'-(11-endo)]-N-ethyl-N'-(5,6,7,8,9,10-hexahydro-6,9-methanobenzo[a][8]annulen-11-yl)sulfamide

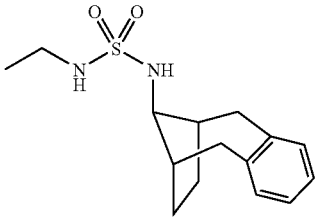

This example used tetrahydrofuran in place of dioxan, and gave the title sulfamide (76 mg, 61%) as a colourless solid, δ ($^1$H, 360 MHz, CDCl$_3$) 1.16–1.27 (5H, m), 1.65–1.73 (2H, m), 2.47–2.54 (2H, m), 2.63 (2H, dd, J=16.0, 7.6), 3.08–3.20 (4H, m), 3.74–3.81 (1H, m), 4.15 (1H, br t, J=5.8), 4.69 (1H, br d, J=7.8), 7.08 (4H, br s); δ ($^{13}$C, 90 MHZ, CDCl$_3$) 16.9, 27.4, 37.1, 39.8, 40.1, 61.8, 127.9, 133.3, 141.0; MS (ES+) 295 ([MH]$^+$).

Example 7

[N-(11-endo)]-N-(5,6,7,8,9,10-hexahydro-6,9-methanobenzo[a][8]annulen-11-yl)-N'-isopropylsulfamide

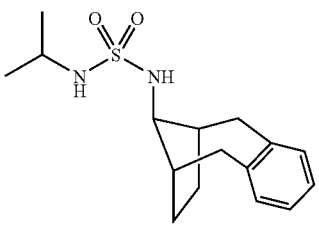

Colourless solid (86%), δ ($^1$H, 360 MHz, CDCl$_3$) 1.16–1.28 (8H, m), 1.67–1.72 (2H, m), 2.49–2.55 (2H, m), 2.64 (2H, dd, J=16.0, 7.5), 3.09 (2H, d, J=16.0), 3.57–3.65 (1H, m), 3.75–3.81 (1H, m), 3.99 (1H, br d, J=7), 4.62 (1H, br d, J=7), 7.09 (4H, br S); δ ($^{13}$C, 90 MHz, CDCl$_3$) 25.7, 27.4, 37.2, 39.7, 48.1, 61.8, 127.9, 133.4, 140.9; MS (ES+) 309 ([MH]$^+$).

Example 8

[N'-(11-endo)]-N-(tert-butyl)-N'-(5,6,7,8,9,10-hexahydro-6,9-methanobenzo[a][8]annulen-11-yl)sulfamide

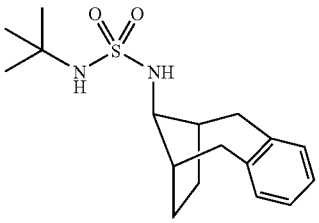

Colourless solid (70%), δ ($^1$H, 360 MHz, CDCl$_3$) 1.16–1.22 (2H, m), 1.40 (9H, s), 1.67–1.73 (2H, m), 2.50–2.57 (2H, m), 2.63 (2H, dd, J=16.0, 7.6), 3.10 (2H, d, J=15.8), 3.76–3.81 (1H, m), 4.11 (1H, br s), 4.58 (1H, br d, J=8), 7.09 (4H, br s); δ ($^{13}$C, 90 MHz, CDCl$_3$) 27.5, 31.8, 37.2, 39.7, 56.0, 61.9, 127.8, 133.3, 141.0; MS (ES+) 323 ([MH]$^+$).

Example 9

[N'-(11-endo)]-N-butyl-N'-(5,6,7,8,9,10-hexahydro-6,9-methanobenzo[a][8]annulen-11-yl)sulfamide

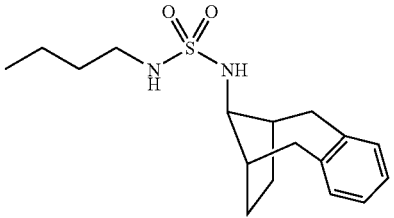

Colourless solid (93%), δ ($^1$H, 360 MHz, CDCl$_3$) 0.95 (3H, t, J=7.3), 1.16–1.23 (2H, m), 1.35–1.45 (2H, m), 1.53–1.62 (2H, m), 1.66–1.73 (2H, m), 2.47–2.54 (2H, m), 2.63 (2H, dd, J=16.0, 7.6), 3.07–3.13 (4H, m), 3.74–3.81 (1H, m), 4.13 (1H, m), 4.65 (1H, br d, J=8), 7.09 (4H, br s); δ ($^{13}$C, 90 MHz, CDCl$_3$) 15.5, 21.7, 27.4, 33.5, 37.1, 39.8, 44.9, 61.8, 127.9, 133.3, 141.0; MS (ES+) 323 ([MH]$^+$).

Example 10

[N-(11-endo)]-N-(5,6,7,8,9,10-hexahydro-6,9-methanobenzo[a][8]annulen-11-yl)-N'-prop-2-ynyl-sulfamide

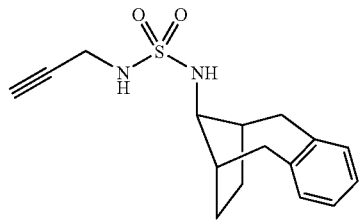

Colourless solid (77%), δ ($^1$H, 360 MHz, CDCl$_3$) 1.18–1.24 (2H, m), 1.67–1.72 (2H, m), 2.35 (1H, t, J=2.6), 2.52–2.59 (2H, m), 2.64 (2H, dd, J=15.8, 7.6), 3.11 (2H, dd, J=15.7), 3.78–3.84 (1H, m), 3.93 (2H, dd, J=6.0, 2.5), 4.48 (1H, br t, J=5.8), 4.77 (1H, br d, J=7), 7.09 (4H, br s); MS (ES+) 305 ([M!H]$^+$).

Example 11

[N'-(11-endo)]-N-allyl-N'-(5,6,7,8,9-hexahydro-6,9-methanobenzo[a][8]annulen-11-yl)sulfamide

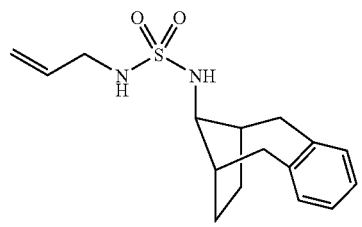

Colourless solid (82%), δ ($^1$H, 360 MHz, CDCl$_3$) 1.16–1.24 (2H, m), 1.65–1.73 (2H, m), 2.46–2.55 (2H, m), 2.63 (2H, dd, J=16.0, 7.6), 3.09 (2H, d, J=15.9), 3.70–3.82 (3H, m), 4.29 (1H, br t, J=6), 4.71 (1H, br d, J=8), 5.22 (1H, d, J=11.4), 5.31 (1H, d, J=17.1), 5.86–5.97 (1H, m), 7.09 (4H, br s); δ ($^{13}$C, 90 MHz, CDCl$_3$) 27.4, 37.1, 39.7, 47.7, 61.8, 119.7, 127.9, 133.3, 135.2, 140.9; MS (ES+) 307 ([MH]$^+$).

Example 12

[N-(R/S), N'-(11-endo)]-N-(sec-butyl)-N'-(5,6,7,8,9,10-hexahydro-6,9-methanobenzo[a][8]annulen-11-yl)sulfamide

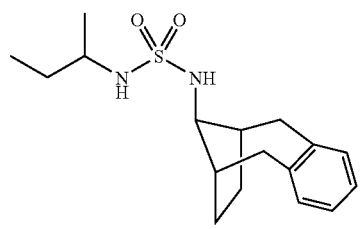

Solid (81%), δ ($^1$H, 360 MHz, CDCl$_3$) 0.97 (3H, t, J=7.5), 1.16–1.26 (5H, m) 1.48–1.71 (4H, m), 2.48–2.55 (2H, m), 2.63 (2H, dd, J=16.0, 7.6), 3.09 (2H, dd, J=16.0, 2.6), 3.36–3.45 (1H, m), 3.75–3.81 (1H, m), 4.03 (1H, br d, J=8), 4.65 (1H, br d, J=8), 7.09 (4H, br s); δ ($^{13}$C, 90 MHz, CDCl$_3$) 11.9, 23.0, 27.4, 32.1, 37.2, 39.7, 53.4, 61.8, 127.9, 133.8, 141.0; MS (ES+) 323 ([MH]$^+$).

Example 13

[N-(11-endo)]-N-(5,6,7,8,9,10-hexahydro-6,9-methanobenzo[a][8]annulen-11-yl)-N'-(2-methoxy-ethyl)sulfamide

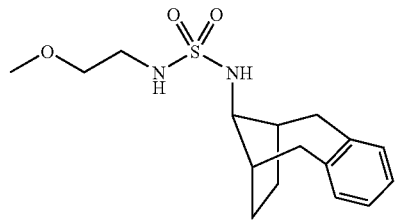

Colourless solid (84%), δ ($^1$H, 360 MHz, CDCl$_3$) 1.17–1.24 (2H, m), 1.66–1.72 (2H, m), 2.49–2.56 (2H, m), 2.63 (2H, dd, J=15.9, 7.6), 3.10 (2H, d, J=15.9), 3.25–3.30 (2H, m), 3.37 (3H, s), 3.55 (2H, t, J=5.0), 3.75–3.81 (1H, m), 4.65 (1H, br t, J=5), 4.78 (1H, br d, J=8), 7.09 (4H, s); δ($^{13}$C, 90 MHz, CDCl$_3$) 27.5, 37.1, 39.7, 45.0, 60.7, 61.8, 72.7, 127.9, 133.3, 141.0; MS (ES+) 325 ([MH]$^+$).

Example 14

[N'-(11-endo)]-N-cyclopropyl-N'-(5,6,7,8,9,10-hexahydro-6,9-methanobenzo[a][8]annulen-11-yl)sulfamide

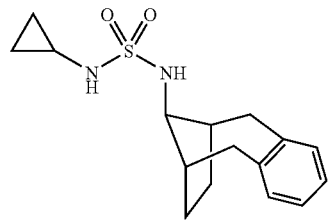

Colourless solid (95%), δ ($^1$H, 400 MHz, CDCl$_3$) 0.71–0.74 (4H, m), 1.17–1.24 (2H, m), 1.65–1.72 (2H, m), 2.48–2.67 (5H, m), 3.14 (2H, d, J=14.4), 3.70–3.76 (1H, m), 4.73 (1H, br s), 4.81 (1H, br d, J=7), 7.09 (4H, s); δ ($^{13}$C, 90 MHz, CDCl$_3$) 8.0, 26.2, 27.4, 37.1, 39.9, 61.9, 127.9, 133.3, 141.0; MS (ES+) 307 ([MH]$^+$).

Example 15

[N'-(11-endo)]-N-cyclobutyl-N'-(5,6,7,8,9,10-hexahydro-6,9-methanobenzo[a][8]annulen-11-yl)sulfamide

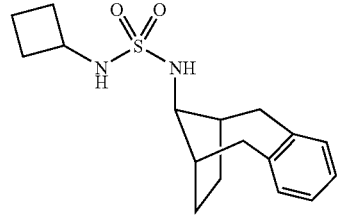

Colourless solid (85%), δ ($^1$H, 360 MHz, CDCl$_3$) 1.16–1.22 (2H, m), 1.64–1.79 (4H, m), 1.90–2.02 (2H, m), 2.35–2.43

(2H, m), 2.74–2.52 (2H, m), 2.63 (2H, dd, J=16.0, 7.6), 3.08 (2H, d, J=15.9), 3.71–3.77 (1H, m), 3.84–3.93 (1H, m), 4.43 (1H, br d, J=9), 4.65 (1H, br d, J=8), 7.09 (4H, s); δ ($^{13}$C, 90 MHz, CDCl$_3$) 16.7, 27.3, 33.7, 37.0, 39.6, 50.0, 61.7, 127.8, 133.2, 140.9; MS (ES+) 321 ([MH]$^+$).

Example 16

[N'-(11-endo)]-N-cyclohexyl-N'-(5,6,7,8,9,10-hexahydro-6,9-methanobenzo[a][8]annulen-11-yl)sulfamide

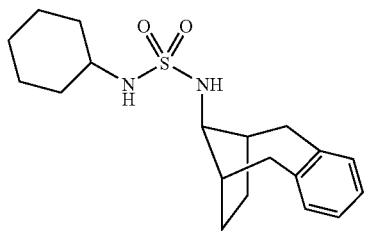

Colourless solid (77%), δ ($^1$H, 360 MHz, CDCl$_3$) 1.14–1.42 (8H, m), 1.55–1.77 (4H, m), 2.00–2.06 (2H, m), 2.47–2.54 (2H, m), 2.64 (2H, dd, J=16.0, 7.6), 3.10 (2H, d, J=16.0), 3.20–3.32 (1H, m), 3.74–3.80 (1H, m), 4.20 (1H, br d, J=8), 4.73 (1H, br d, J=8), 7.08 (4H, s); δ ($^{13}$C, 90 MHz, CDCl$_3$) 26.7, 27.1, 27.5, 36.0, 37.2, 39.7, 54.7, 61.8, 127.9, 133.3, 141.0; MS (ES+) 349 ([MH]$^+$).

Example 17

[N-(9-endo)]-N-bicyclo[4.2.1]non-3-en-9-yl-N'-propylsulfamide

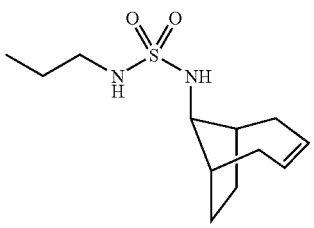

Step 1. Bicyclo[4.2.1]non-3-en-9-one oxime

Hydroxylamine hydrochloride (1.53 g, 22.0 mmol) and sodium acetate (2.99 g, 36.4 mmol) were added to a solution of bicyclo[4.2.1]non-3-en-9-one (1.0 g, 7.3 mmol) and the resulting solution warmed to reflux overnight. The reaction was then cooled to room temperature and the solvent removed under reduced pressure. The residue was partitioned between EtOAc (50 mL) and NaOH solution (1N aq 50 mL), the organic layer separated, dried over MgSO$_4$, filtered and the solvent removed under reduced pressure to give the title compound (1.02 g, 93%). m/z 152 (M+H)$^+$.

Step 2. endo-Bicyclo[4.2.1]non-3-en-9-ylamine

NaCNBH$_3$ (451 mg, 7.3 mmol) was added to a solution of bicyclo[4.2.1]non-3-en-9-one oxime (550 mg, 3.6 mmol) in MeOH (10 mL) at −30° C. containing methyl orange indicator (20 μl of 0.1% solution) followed by enough HCl (5N, aq) to turn the solution pink. As the reaction proceeded sufficient HCl was added to maintain a pink colour. After two hours the reaction was allowed to warm to room temperature and poured onto ice/NaOH (4N, aq), and extracted into EtOAc (30 mL), dried over MgSO$_4$, filtered and the solvent removed under reduced pressure. The recovered hydroxylamine was taken up in AcOH (2 mL) an added to a stirred suspension of activated Zn dust (4.72 g 72.6 mmol) in AcOH (50 mL). After 30 min TLC (2N NH$_3$/MeOH: DCM 5:95) showed complete reduction of the hydroxylamine to a more polar product. The solution was filtered through celite to remove the zinc and the solvent removed under reduced pressure. The residue was basified with NaHCO$_3$ and extracted into EtOAc (50 mL), dried over MgSO$_4$, filtered and the solvent removed under reduced pressure to afford the title product (220 mg 46%). $^1$H NMR (CDCl$_3$) δ 1.33–1.43 (2H, m), 1.48 (2H bs, NH$_2$), 1.78–1.81 (2H, m), 1.82 (2H, bd, J=16 Hz), 2.09–2.32 (4H, m), 3.39 (1H, t, J=8.0 Hz), 5.48 (2H, d, J=4 Hz). m/z 138 (M+H)$^+$.

Step 3: [9-endo]-2-hydroxyphenyl bicyclo[4.2.1]non-3-en-9-ylsulfamate

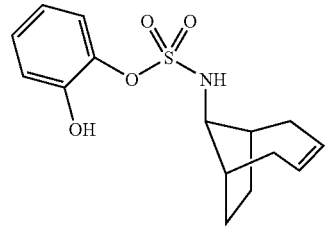

A solution of [9-endo]-bicyclo[4.2.1]non-3-en-9-amine (640 mg, 4.7 mmol) and triethylamine (655 μL, 4.7 mmol) in dry DCM (5+5 mL) was added to a solution of catechol sulfate (940 mg, 5.5 mmol) in dry DCM (10 mL) at 0° C. under nitrogen. After thirty minutes at 0° C. the cooling bath was removed and the reaction was stirred at room temperature for two hours. The reaction mixture was then partitioned between DCM and 2N hydrochloric acid. The aqueous layer was further extracted with DCM (x2). The combined extracts were dried (Na$_2$SO$_4$), filtered and evaporated. The residue was purified by chromatography on silica gel eluting with 2% to 5% ethyl acetate/DCM to give the title sulfamate (210 mg, 14%) as a thick oil, δ ($^1$H, 400 MHz, CDCl$_3$) 1.41–1.48 (2H, m), 1.81–1.88 (2H, m), 2.16–2.27 (4H, m), 2.48–2.53 (2H, m), 4.10 (1H, t, J=6.7), 4.8 (1H, br s), 5.48 (2H, m), 6.91 (1H, td, J=8.0, 1.5), 7.05 (1H, dd, J=8.2, 1.6), 7.17–7.25 (2H, m).

Step 4: [N-(9-endo)]-N-bicyclo[4.2.1]non-3-en-9-yl-N'-propylsulfamide.

This compound was prepared by the method of examples 2–16, using the sulfamate from Step 3 and n-propylamine. This gave the title sulfamide (70 mg, 90%) as a colourless solid, δ ($^1$H, 400 MHz, CDCl$_3$) 0.96 (3H, t, J=7.4), 1.40–1.46 (2H, m), 1.55–1.64 (2H, m), 1.78–1.84 (2H, m), 2.15–2.33 (4H, m), 2.45–2.52 (2H, m), 3.00–3.05 (2H, m), 3.81–3.88 (1H, m), 4.11 (1H, br t, J=6), 4.23 (1H, br d, J=11), 5.46–5.49 (2H, m).

Example 18

[11-endo]2',3',4',5,5',6,7,8,9,10-decahydro-5'-methyl-spiro[6,9-methanobenzocyclooctene-11,3'-[1,2,5]thiadiazole]1',1'-dioxide

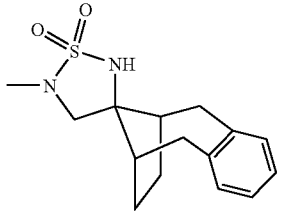

Step 1. [11-endo]2',3',4',5,5',6,7,8,9,10-decahydro-spiro[6,9-methanobenzocyclooctene-11,3'-[1,2,5]thiadiazole]1',1'-dioxide.

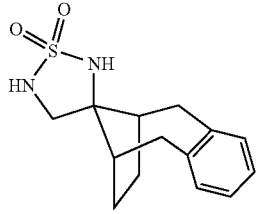

A mixture of 5,6,7,8,9,10-hexahydro-6,9-methanobenzo[a][8]annulen-11-one (J. Org Chem. 1982, 47, 4329) (4.0 g, 21.5 mmol), potassium cyanide (1.4 g, 21.5 mmol) and ammonium chloride (1.2 g, 22.4 mmol) in dioxan (5 mL) and water (5 mL) was stirred vigorously at room temperature for 72 hours. The mixture was then extracted with diethyl ether (x3). The combined organic extracts were dried ($Na_2SO_4$), filtered and evaporated. The residue was purified by chromatography on silica gel eluting with 10% to 20% to 30% ethyl acetate/hexanes to give a mixture of the α-amino nitrile and the cyanohydrin in a 2:1 ratio (2.3 g) as a colourless solid. This material was used directly in the next step.

Lithium aluminium hydride (1.0M in tetrahydrofuran, 18 mL, 18 mmol) was added dropwise to a stirred solution of the mixture of the α-amino-nitrile and the cyanohydrin (2.0 g) in dry tetrahydrofuran (20 mL) at 0° C. under nitrogen. Upon complete addition the reaction was allowed to warm to room temperature and stirred at this temperature overnight. The reaction was then recooled to 0° C. and quenched by dropwise addition of water (0.75 mL), then 4N aqueous sodium hydroxide (0.75 mL) and finally water (2.25 mL). The reaction mixture was diluted with ethyl acetate and anhydrous sodium sulfate was added to aid filtration. The reaction mixture was filtered through Hyflo®, washing with methanol. The filtrate was evaporated to give the crude diamine (~3 g) as a thick oil. The crude diamine was taken up in dry pyridine (60 mL) at room temperature under nitrogen, and sulfamide (2.6 g, 27 mmol) was added in one portion. The solution was then stirred and heated at reflux overnight. Upon cooling, the pyridine was removed in vacuo. The residue was azeotroped with toluene (x2), then partitioned between DCM and 2N hydrochloric acid. The aqueous layer was further extracted with DCM (x2). The combined organic extracts were dried ($Na_2SO_4$), filtered and evaporated. The residue was purified by chromatography on silica gel eluting with 5% to 10% ethyl acetate/DCM to give the title cyclic sulfamide (630 mg, ~10% from the ketone) as an off white solid, δ ($^1H$, 400 MHz, $CDCl_3$) 1.24–1.33 (2H, m), 1.65–1.72 (2H, m), 2.39–2.44 (2H, m), 2.71 (2H, dd, J=15.9, 7.6), 3.22 (2H, d, J=15.8), 3.37 (2H, d, J=7.4), 4.60–4.69 (2H, m), 7.06–7.14 (4H, m); δ ($^1H$, 360 MHz, $d_6$-DMSO) 0.96–1.03 (2H, m), 1.60–1.66 (2H, m), 2.30–2.35 (2H, m), 2.57 (2H, dd, J=15.7, 7.7), 3.10–3.19 (4H, m), 7.04–7.12 (5H, m), 7.38 (1H, s); δ ($^{13}C$, 90 MHz, $d_6$-DMSO) 26.7, 38.7, 43.0, 58.8, 77.4, 128.1, 133.4, 141.7; MS (ES+) 279 ([MH]$^+$).

Step 2: [11-endo]2',3',4',5,5',6,7,8,9,10-decahydro-5'-methylspiro[6,9-methanobenzocyclooctene-11,3'-[1,2,5]thiadiazole]1',1'-dioxide.

Lithium bis(trimethylsilyl)amide (1.0M in tetrahydrofuran, 330 μL, 0.33 mmol) was added to a stirred solution of the product from Step 1 (92 mg, 0.33 mmol) in dry tetrahydrofuran (3 mL) at 0° C. under nitrogen. The cooling bath was removed and the reaction was stirred at room temperature for one hour. Iodomethane (20 μL, 0.32 mmol) was then added, and the reaction was stirred at room temperature overnight. The mixture was partitioned between ethyl acetate and water. The aqueous layer was further extracted with ethyl acetate (x2). The combined organic extracts were dried ($Na_2SO_4$), filtered and evaporated. The residue was purified by chromatography on silica gel eluting with 2% to 5% ethyl acetate/DCM. The initial sample was further purified by preparative HPLC to give the title cyclic sulfamide (16 mg, 17%) as a colourless solid, δ ($^1H$, 360 MHz, $CDCl_3$) 1.24–1.31 (2H, m), 1.65–1.71 (2H, m), 2.38–2.44 (2H, m), 2.68 (2H, dd, J=16.1, 7.6), 2.76 (3H, s), 3.14–3.21 (4H, m) 4.71 (1H, br s), 7.06–7.14 (4H, m); δ ($^{13}C$, 90 MHz, $CDCl_3$) 26.5, 34.4, 38.2, 45.1, 66.1, 70.9, 128.1, 133.3, 140.4; MS (ES+) 293 ([MH]$^+$).

Example 19

[11-endo]2',3',4',5,5',6,7,8,9,10-decahydro-5'-ethyl-spiro[6,9-methanobenzocyclooctene-11,3'-[1,2,5]thiadiazole]1',1'-dioxide

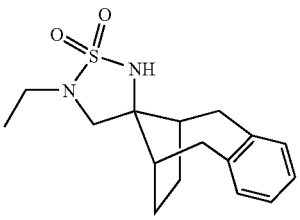

Sodium hydride (60% dispersion in oil, 15 mg, 0.38 mmol) was added in one portion to a stirred solution of the product from Example 18 Step 1. (100 mg, 0.35 mmol) in dry DMF (1 mL) at 0° C. under nitrogen. The cooling bath was removed and the reaction was stirred at room temperature for one hour before the addition of ethyl iodide (30 μL, 0.38 mmol). The reaction was stirred at room temperature overnight, before being quenched by the addition of saturated aqueous sodium hydrogen carbonate. The mixture was then partitioned between ethyl acetate and water. The aqueous layer was further extracted with ethyl acetate (x2). The combined organic extracts were washed with saturated aqueous sodium chloride (x1), then dried ($Na_2SO_4$), filtered and evaporated. The residue was purified by chromatography on silica gel eluting with 2% to 5% ethyl acetate/DCM to give the title cyclic sulfamide (46 mg, 44%) as a colourless solid, δ ($^1H$, 360 MHz, $CDCl_3$) 1.24–1.31 (5H, m), 1.65–1.72 (2H, m), 2.38–2.45 (2H, m), 2.68 (2H, dd, J=16.0, 7.6), 3.10–3.15 (3H, m), 3.19–3.22 (3H, m), 4.67 (1H, br s), 7.06–7.14 (4H, m); δ ($^{13}C$, 90 MHz, $CDCl_3$) 15.1, 26.6, 38.2, 43.9, 45.1, 63.6, 70.9, 128.1, 133.3, 140.5; MS (ES+) 307 ([MH]$^+$).

Example 20

[11-endo]2',3',4',5,5',6,7,8,9,10-decahydro-5'-propyl-spiro[6,9-methanobenzocyclooctene-11,3'-[1,2,5]thiadiazole]1',1'-dioxide

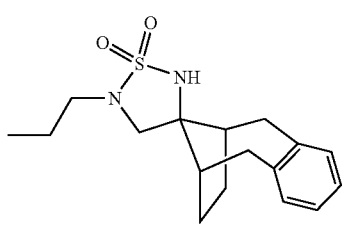

Sodium hydride (60% dispersion in oil, 20 mg, 0.5 mmol) was added in one portion to a stirred solution of the product from Example 18 Step 1 (140 mg, 0.5 mmol) in dry DMF (2.5 mL) at room temperature under nitrogen. After one hour 1-bromopropane (50 μL, 0.55 mmol) was added. The reaction was stirred at room temperature for two hours, before being quenched with water. The mixture was then partitioned between ethyl acetate and water. The aqueous layer was further extracted with ethyl acetate (x2). The combined organic extracts were dried ($Na_2SO_4$), filtered and evaporated. The residue was purified by chromatography on silica gel eluting with 2% to 5% ethyl acetate/DCM to give the title cyclic sulfamide (75 mg, 47%) as a colourless solid, δ ($^1$H, 360 MHz, $CDCl_3$) 0.98 (3H, t, J=7.4), 1.24–1.31 (2H, m), 1.61–1.71 (4H, m), 2.38–2.44 (2H, m), 2.67 (2H, dd, J=16.0, 7.6), 2.99–3.04 (2H, m), 3.16–3.21 (4H, m), 4.68 (1H, br s), 7.06–7.13 (4H, m); δ ($^{13}$C, 90 MHz, $CDCl_3$) 13.2, 23.1, 26.6, 38.2, 45.0, 50.2, 64.1, 71.1, 128.1, 133.3, 140.5; MS (ES+) 321 ([MH]$^+$).

Example 21

[11-endo]2',3',4',5,5',6,7,8,9,10-decahydro-5'-butyl-spiro[6,9-methanobenzocyclooctene-11,3'-[1,2,5]thiadiazole]1',1'-dioxide

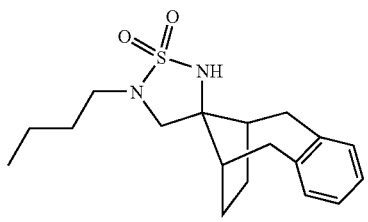

Sodium hydride (60% dispersion in oil, 15 mg, 0.38 mmol) was added in one portion to a stirred solution of the product from Example 18 Step 1 (100 mg, 0.35 mmol) in dry DMF (1 mL) at 0° C. under nitrogen. The cooling bath was removed and the reaction was stirred at room temperature for one hour before the addition of n-butyl iodide (45 μL, 0.40 mmol). The reaction was stirred at room temperature overnight, before being quenched by the addition of saturated aqueous ammonium chloride. The mixture was then partitioned between ethyl acetate and water. The aqueous layer was further extracted with ethyl acetate (x3). The combined organic extracts were washed with saturated aqueous sodium chloride (x1), then dried ($Na_2SO_4$), filtered and evaporated. The residue was purified by chromatography on silica gel eluting with 1% to 2% ethyl acetate/DCM to give the title cyclic sulfamide (65 mg, 56%) as a colourless solid, δ ($^1$H, 360 MHz, $CDCl_3$) 0.95 (3H, t, J=7.4), 1.24–1.31 (2H, m), 1.35–1.46 (2H, m), 1.55–1.71 (4H, m), 2.38–2.45 (2H, m), 2.67 (2H, dd, J=16.0, 7.6), 3.02–3.08 (2H, m), 3.15–3.22 (4H, m), 4.68 (1H, br s), 7.05–7.14 (4H, m); δ ($^{13}$C, 90 MHz, $CDCl_3$) 15.5, 21.9, 26.6, 31.8, 38.2, 45.0, 48.2, 64.0, 71.0, 128.1, 133.3, 140.5.

Example 22

[11-endo]2',3',4',5,5',6,7,8,9,10-decahydro-5'-(2,2,2-trifluoroethyl)-spiro[6,9-methanobenzocyclooctene-11,3'-[1,2,5]thiadiazole]1',1'-dioxide

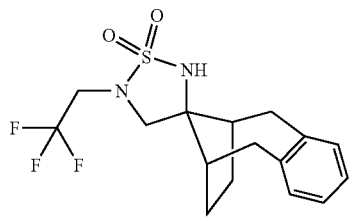

A mixture of the product from Example 18 Step 1 (118 mg, 0.4 mmol), cesium carbonate (130 mg, 0.4 mmol) and 2-iodo-1,1,1-trifluoroethane (50 μL, 0.5 mmol) in dry DMF (2 mL) was stirred and heated at 65° C. in a sealed tube overnight. The reaction was allowed to cool, then partitioned between ethyl acetate and water. The aqueous layer was further extracted with ethyl acetate (x3). The combined organic extracts were washed with saturated aqueous sodium chloride (x1), then dried ($Na_2SO_4$), filtered and evaporated. The residue was purified by chromatography on silica gel eluting with DCM to give the title cyclic sulfamide (15 mg, 10%), δ ($^1$H, 360 MHz, $CDCl_3$) 1.28–1.35 (2H, m), 1.67–1.73 (2H, m), 2.42–2.46 (2H, m), 2.69 (2H, dd, J=16.0, 7.6), 3.22 (2H, d, J=15.9), 3.43 (2H, s), 3.68 (2H, q, J=8.7), 4.73 (1H, br s), 7.06–7.14 (4H, m); δ ($^{13}$C, 90 MHz, $CDCl_3$) 26.7, 28.1, 44.8, 50.2 (q, $J^{13C-19F}$=35), 66.1, 72.1, 128.2, 133.3, 140.2.

Example 23

[9-endo]2',3',4',5'-tetrahydro-5'-propylspiro[bicyclo[4.2.1]non-3-ene-9,3'-[1,2,5]thiadiazole]1',1'-dioxide

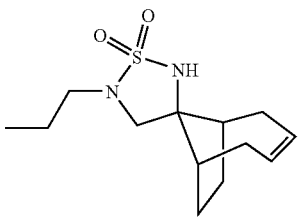

Step 1: [9-endo]2',3'4',5'-tetrahydro-spiro[bicyclo[4.2.1]non-3-ene-9,3'-[1,2,5]thiadiazole]1',1'-dioxide.

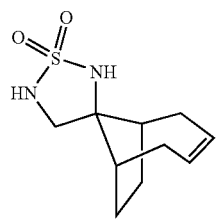

This compound was prepared by the method of Example 18 starting from bicyclo[4.2.1]non-3-en-9-one (5.0 g, 37 mmol). The cyclic sulfamide (180 mg,) was obtained as a colourless solid, δ ($^1$H, 400 MHz, CDCl$_3$) 1.52–1.61 (2H, m), 1.84–1.92 (2H, m), 2.15–2.24 (2H, m), 2.32–2.42 (4H, m), 3.37–3.40 (2H, m), 4.38 (1H, br s), 4.55 (1H, br s), 5.47–5.52 (2H, m); δ ($^{13}$C, 100 MHz, CDCl$_3$) 26.7, 32.9, 43.0, 57.2, 74.7, 126.8.

Step 2

Sodium hydride (60% dispersion in oil, 15 mg, 0.38 mmol) was added in one portion to a stirred solution of the cyclic sulfamide from Step 1 (87 mg, 0.38 mmol) in dry DMF (2 mL) at room temperature under nitrogen. After one hour 1-bromopropane (36 μL, 0.40 mmol) was added. The reaction was stirred at room temperature for 1.5 hours, before being quenched with water. The mixture was then partitioned between ethyl acetate and water. The aqueous layer was further extracted with ethyl acetate (x2). The combined organic extracts were washed with water (x1), saturated aqueous sodium chloride (x1), then dried (Na$_2$SO$_4$), filtered and evaporated. The residue was purified by chromatography on silica gel eluting with 20% ethyl acetate/hexanes to give the N-alkylated cyclic sulfamide (64 mg, 85%) as a colourless solid, δ ($^1$H, 360 MHz, CDCl$_3$) 0.98 (3H, t, J=7.4), 1.49–1.55 (2H, m), 1.60–1.70 (2H, m), 1.84–1.92 (2H, m), 2.13–2.22 (2H, m), 2.32–2.43 (4H, m), 2.95–3.00 (2H, m), 3.21 (2H, s), 4.31 (1H, br s), 5.46–5.53 (2H, m); δ ($^{13}$C, 90 MHz, CDCl$_3$) 13.2, 23.0, 28.4, 34.5, 45.4, 50.1, 63.2, 71.0, 128.6; MS (ES+) 271 ([MH]$^+$).

Example 24

(2-(4-Fluorophenoxy)-N-endo-(11-{[(propylamino)sulfonyl]amino}-5,6,7,8,9,10-hexahydro-6,9-methanobenzo[a][8]annulen-2-yl)acetamide

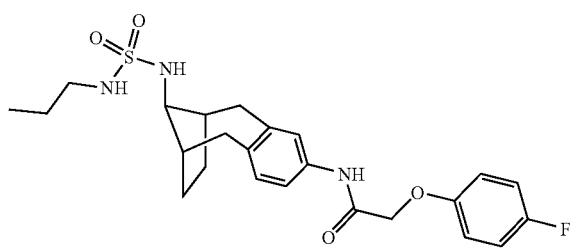

Step 1  5-Nitro-tricyclo[8.2.1.0$^{3,8}$]trideca-3(8),4,6-trien-13-one oxime

Hydroxylamine hydrochloride (9.72 g) was added to a stirred solution of 5-nitro-tricyclo[8.2.1.03,8]trideca-3(8),4,6-trien-13-one* (10.82 g) and sodium acetate (19.08 g) in a mixture of absolute ethanol (50 rat) and water (50 mL). The reaction was warmed to reflux for 18 hours cooled to room temperature and diluted with water (200 mL). The product was filtered off, dried under high vacuum to afford the title compound as a white powder (10.73 g) m/z 247 (M+H$^+$).

*J. Org. Chem. 1982, 47, 4329–4334

Step 2  N-(5-Nitro-tricyclo[8.2.1.0$^{3,8}$]trideca-3(8),4,6-trien-13-yl)hydroxylamine

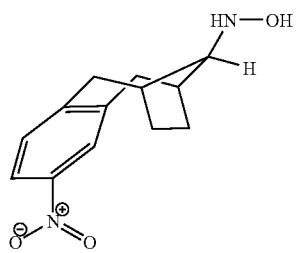

Sodium cyanoborohydride (255 mg) was added in a single portion to a solution of the oxime of Step 1 (500 mg) in dry methanol (20 mL) at −20° C. 2N HCl was then added until the solution was at pH 3 (Methyl Orange). After 3 hours the reaction was diluted with 4N NaOH (50 mL) and reduced to 1/3 volume. The residue was extracted with DCM (4×50 mL), the organic layers combined and dried over MgSO$_4$, filtered and the solvent removed under reduced pressure to afford the title compound as a white foam (477 mg). m/z 249 (M+H$^+$).

Step 3:  Tricyclo[8.2.1.0$^{3,8}$]trideca-3(8),4,6-triene-5,13-diamine

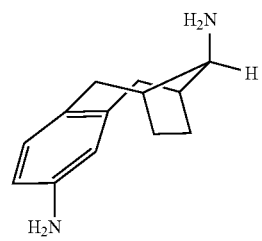

Activated zinc dust (excess) was added to a rapidly stirring solution of the hydroxylamine from Step 2 (2.0 g) in 1:1 tetrahydrofuran:2N aqueous HCl (100 ml). After two hours the reaction mixture was filtered and reduced to half volume under reduced pressure. The residue was basified to pH 9 with 4N NaOH and extracted into ether (4×100 mL). The organic extracts were combined, dried over MgSO$_4$, filtered and the solvent removed under reduced pressure to afford the title compound as a clear oil. (1.6 g). m/z 203 (M+H$^+$).

Step 4:  (5-Amino-tricyclo[8.2.1.0$^{3,8}$]trideca-3(8),4,6-trien-13-yl)-carbamic acid tert-butyl ester*

*-alternative name-[6S/R,9R/S,11R/S] tert-butyl 2-amino-5,6,7,8,9,10-hexahydro-6,9-methanobenzo[a][8]annulen-11-ylcarbamate.

A solution of di-tertbutyldicarbonate (864 mg) in DCM (20 mL) was added over four hours to a stirred solution of the diamine from Step 3 (800 mg) in DCM (50 ml) at −20° C. After a further two hours the solution was warmed to room temperature and the solvent removed under reduced pressure. The residual oil was purified by chromatography on silica gel (30% EtOAc/isohexane) to afford the product as a white solid (500 mg). $^1$H NMR (CDCl$_3$ 400 MHz) δ

1.20–1.25 (2H, m), 1.46 (9H, s), 1.65–1.69 (2H, m), 2.40–2.46 (4H, m), 2.86–2.90 (2H, m), 4.05 (1H, brs), 5.29 (1H, brs), 6.41–6.44 (2H, m), 6.84 (1H, d, J=5.0 Hz).

Step 5: [6S/R,9R/S,11R/S] tert-butyl 2-{[(4-fluorophenoxy) acetyl]amino}-5,6,7,8,9,10-hexahydro-6,9-methanobenzo [a][8]annulen-11-ylcarbamate.

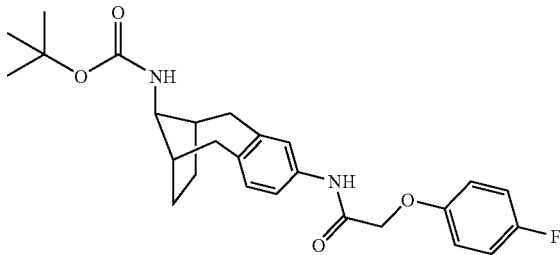

To a solution of 4-fluorophenoxyacetic acid (177 mg) in THF (5 ml) at room temperature under nitrogen was added CDI (168 mg) in one portion. The mixture was heated to 70° C. for 2 hrs, then the aniline derivative from Step 4 (210 mg) was added. The reaction was maintained at this temperature for a further 16 hrs. Upon cooling, the reaction mixture was diluted with EtOAc (10 ml), then washed with 1M HCl (10 ml), 1M NaHCO$_3$ (10 ml) and brine. The organic extracts were dried, filtered and concentrated to give the title amide (270 mg, 87%) as a white solid δ ($^1$H, 360 MHz CDCl$_3$) 1.09 (2H, m), 1.39 (9H, s), 1.61 (2H, m), 2.40 (2H, m), 2.50 (2H, m), 2.90 (2H, m), 3.93 (1H, brm), 4.45 (2H, s), 4.95 (1H, brs), 6.84 (2H, m), 6.96 (3H, m), 7.25 (2H, m), 8.15 (1H, brs).

Step 6: [6S/R,9R/S,11R/S] 2-hydroxyphenyl 2-{[(4-fluorophenoxy)acetyl]amino}-5,6,7,8,9,10-hexahydro-6,9-methanobenzo[a][81 annulen-11-ylsulfamate.

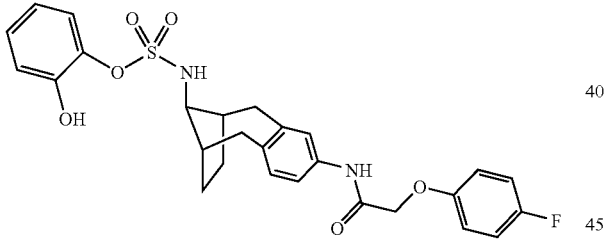

The product from Step 5 was dissolved in DCM (10 ml), cooled to 0° C. and TFA (2 ml) added dropwise. The mixture was allowed to warm to room temperature and stirred for 2.5 hrs, concentrated, added to ice-chilled saturated NaHCO$_3$ (20 ml) and extracted with DCM (3×20 ml). The extracts were dried and concentrated to give the amine as an oil (210 mg, 100%), which was dissolved in THF (2 ml) and catechol sulfate (108 mg) added in one portion at 0° C. The mixture was allowed to warm to room temperature and stirred for 16 hrs., then diluted with aqueous NH$_4$Cl (10 ml) and extracted with EtOAc (3×20 ml). The extracts were dried, concentrated and purified using column chromatography on silica eluting with 30% EtOAc/hexane to give the title sulfamate (138 mg, 44%) as a white solid δ ($^1$H 360 MHz, CDCl$_3$) 1.06 (2H, m), 1.58 (2H, m), 2.43 (4H, m), 2.82 (1H, d, J=14.6), 2.90 (1H, d, J=14.6), 3.84 (1H, m), 4.58 (2H, ABq, J=15.2, 16.9), 6.19 (1H, d, J=6.8), 6.99 (7H, m), 7.23 (5H, m), 8.29 (1H, brs); MS(ES+): 527 ([MH]$^+$).

Step 7: [6S/R,9R/S,11R/S](2-(4-Fluorophenoxy)-(11-} [(propylamino)sulfonyl]amino]-5,6,7,8,9,10-hexahydro-6, 9-methanobenzo[a][8]annulen-2-yl)acetamide.

The product of Step 6 (68 mg) was reacted with n-propylamine by the method of Examples 2–16 to give the title sulfamide (29 mg, 47%) as a white powder, (360 MHz $^1$H, δ-CDCl$_3$) 0.98 (3H, t, J=6.7), 1.20 (2H, m), 1.62 (2H, m), 1.69 (2H, m), 2.50 (2H, m), 2.61 (2H, m), 3.07 (4H, m), 3.76 (1H, dd, J=5.7, 12.2), 4.21 (1H, t, J=5.5), 4.56 (2H, s), 4.70 (1H, d, J=7), 6.94 (2H, m), 7.03 (3H, m), 7.33 (2H, m), 8.16 (1H, brs); MS(ES+): 476 ([MH]$^+$).

Example 25

[6S/R,9R/S,11R/S] (11-{[(tert-butylamino)sulfonyl] amino}-5,6,7,8,9,10-hexahydro-6,9-methanobenzo [a][8]annulen-2-yl)-2-(4-fluorophenoxy)acetamide

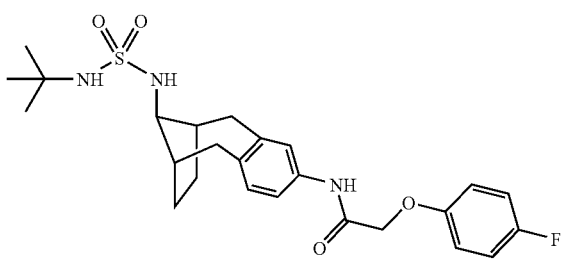

This compound was prepared as described in Example 24, substituting t-butylamine for propylamine in the last step. This gave the title sulfamide (38 mg, 60%) as a colourless solid, (360 MHz $^1$H, δ-CDCl$_3$) 1.21 (2H, m), 1.39 (9H, s), 1.70 (2H, m), 2.52 (2H, m), 2.61 (2H, m), 3.08 (2H, m), 3.77 (1H, m), 4.16 (1H, s), 4.56 (2H, s), 4.62 (1H, d, J=6.8), 6.94 (2H, m), 7.05 (3H, m), 7.33 (2H, m), 8.16 (1H, brs); MS(ES+): 512 (M+Na).

Example 26:

[6S/R,9R/S,11R/S] 2',3',4',5,5',6,7,8,9,10-decahydro-2-benzyloxy-spiro[6,9-methanobenzocyclooctene-11,3'-[1,2,5]thiadiazole]1',1'-dioxide

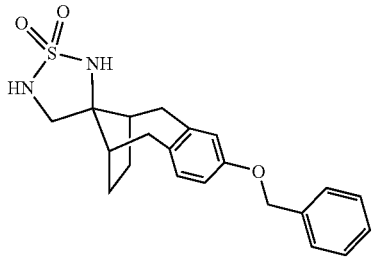

Step 1: 2-benzyloxy-5,6,7,8,9,10-hexahydro-6,9-methanobenzo[a][8]annulen-11-one.

A mixture of 2-hydroxy-5,6,7,8,9,10-hexahydro-6,9-methanobenzo[a][8]annulen-11-one (15 g; J. Org. Chem 1982, 47, 4329), K$_2$CO$_3$ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether the title benzyl ether (19.5 g, 90%) as a white solid (360 MHz $^1$H, δ-CDCl$_3$) 1.32 (2H, m), 1.85 (2H, m), 2.57 (2H, m), 2.87 (4H, m), 5.05 (2H, s), 6.82 (2H, m), 7.11 (1H, d, J=8.2), 7.37 (5H, m).

Step 2: [6S/R,9R/S,11R/S] 11-amino-2-(benzyloxy)-5,6,7,8,9,10-hexahydro-6,9-methanobenzo[a][8]annulene-11-carbonitrile.

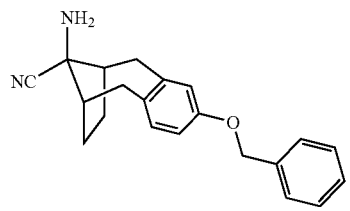

To methanol (1 litre) saturated with ammonia cooled to 0° C. were added ammonium hydroxide (60.4 ml), ammonium chloride (30 g), sodium cyanide (3 g) and 2-benzyloxy-5,6,7,8,9,10-hexahydro-6,9-methanobenzo[α][8]annulen-11-one (9.5 g). The reaction was stirred vigorously for 1 hr to ensure complete dissolution and left standing at 3° C. for 18 hrs. The precipitate was filtered, washed with ice-chilled water, ice-chilled methanol and dried in vacuo at 50° C. to give the title compound (8.4 g, 81%) as a white solid (360 MHz δd$_6$-DMSO) 1.17 (2H, m), 1.84 (2H, m), 2.38 (2H, m), 2.78 (2H, m), 3.40 (2H, m), 5.03 (2H, s), 6.73 (2H, m), 6.98 (1H, d, J=8.2), 7.37 (5H, m).

Step 3: [6S/R,9R/S,11R/S] 2',3',4',5,5',6,7,8,9,10-decahydro-2-benzyloxy-spiro [6,9-methanobenzocyclooctene-11,3'-[1,2,5]thiadiazole]1',1'-dioxide.

To the product of Step 2 (9.3 g) in THF (65 ml) at 0° C. was added LiAlH$_4$ (1M, 58 ml) dropwise and the reaction allowed to warm to room temperature with stirring for 16 hrs. The reaction was cooled to 0° C., EtOAc (100 ml) added, followed by NaOH (2M, 5 ml), filtered and the mixture concentrated. Column chromatography on silica eluting with 5% MeOH/EtOAc gave an oil (3.2 g, 30%) which was dissolved in pyridine (65 ml), sulfamide (2.9 g) added and the mixture heated to reflux for 18 hrs. The mixture was cooled, concentrated in vacuo, azeotroped with toluene and purified using column chromatography on silica eluting with DCM then 10% EtOAc/DCM to give the title cyclic sulfamide as a white foam (2.3 g, 68%), (360 MHz $^1$H, δ-CDCl$_3$) 1.32 (2H, m), 1.66 (2H, m), 2.39 (2H, m), 2.63 (2H, m), 3.13 (1H, d, J=15.8), 3.21 (1H, d, J=15.8), 3.34 (1H, d, J=7.3), 4.80 (1H, t, J=7.3), 4.87 (1H, s), 5.01 (2H, s), 6.72 (2H, m), 6.97 (1H, d, J=8.2), 7.37 (5H, m); MS(ES+): 385 ([MH]$^+$).

Example 27

[6S/R,9R/S,11R/S] 2',3',4',5,5',6,7,8,9,10-decahydro-2-benzyloxy-5'-propylspiro[6,9-methanobenzocyclooctene-11,3'[1,2,5]thiadiazole]1',1'-dioxide

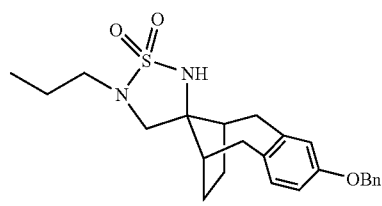

To the product of Example 26 (1.9 g) in DMF (20 ml) at 0° C. under nitrogen was added NaH (218 mg) portionwise and the reaction stirred for 1 hr. Added n-PrBr (494 μl) and allowed to warm to room temperature with stirring for 18 hrs. Added water (100 ml) and extracted with EtOAc (3×50 ml). The combined organic phases were washed with water (2×75 ml) and brine (50 ml). Drying, concentration and column chromatography on silica eluting with DCM then 1–2% EtOAc/DCM gave the title sulfamide (1.1 g, 52%) as a white solid (360 MHz $^1$H, δ-CDCl$_3$) 0.97 (3H, t, J=7.3), 1.31 (2H, m), 1.66 (4H, m), 2.33 (2H, m), 2.60 (2H, m), 3.01 (2H, t, J=7.1), 3.08 (1H, d, J=15.9), 3.18 (1H, d, J=15.9), 3.20 (2H, m), 4.71 (1H, s), 5.02 (2H, s), 6.72 (2H, m), 6.98 (1H, d, J=7.8), 7.37 (5H, m); MS(ES+): 427 ([MH]$^+$).

Example 28

[11-endo] 2',3',4',5,5',6,7,8,9,10-decahydro-2'-acetyl-5'-propylspiro[6,9-methanobenzocyclooctene-11,3'-[1,2,5]thiadiazole]1',1'-dioxide

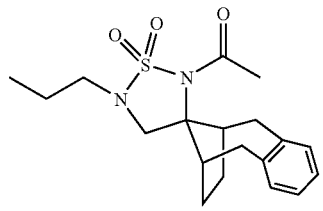

To the product from Example 20 (120 mg) in THF at 0° C. under nitrogen was added NaH (18 mg) portionwise and the reaction stirred for 15 mins. Acetyl chloride (32 μl) was added, the mixture allowed to warm to room temperature and stirred for 18 hrs. Water (20 ml) was added and the mixture extracted with EtOAc (2×20 ml). Drying, concentration and column chromatography on silica eluting with 10% EtOAc/hexane gave the title sulfamide (60 mg, 44%) as a white solid (360 MHz $^1$H, δ-CDCl$_3$) 0.97 (3H, t, J=7.3), 1.29 (2H, m), 1.60 (4H, m), 2.52 (3H, s), 2.66 (2H, dd, J=16, 8.1), 3.09 (6H, m), 3.32 (2H, s), 7.10 (4H, m).

Example 29

2-(2,4-dichlorophenoxy)-N-((11-endo)-11-{[(propylamino)sulfonyl]amino}-5,6,7,8,9,10-hexahydro-6,9-methanobenzo[a][8]annulen-2-yl)propanamide

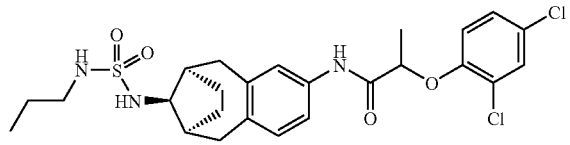

To a stirred solution of the product from Example 24, Step 4; (446 mg, 1.48 mmol) in acetonitrile (20 mL) was added (R/S)-2-(2,4-dichlorophenoxy)-propionic acid (382 mg, 1.63 mmol), HBTU (616 mg, 1.63 mmol) and triethylamine (420 μl, 2.96 mmol). The reaction was stirred at ambient temperature for 24 hours then evaporated. The residue was taken up in DCM (50 mL) and washed with 2N HCl (50 mL), 1N NaOH (50 mL) and brine (50 mL) then dried (MgSO$_4$) and evaporated to leave a residue (0.67 g) which was recrystallized from ether/hexane to afford the desired amide as colourless crystals (380 mg). A solution of the amide from the foregoing step (420 mg) was dissolved in DCM (25 mL) and treated with trifluoroacetic acid (5 mL). After stirring at ambient temperature for 2 hours, the mixture was diluted with ethyl acetate (50 mL), washed with 4N NaOH (2×50 mL), dried (MgSO$_4$) and evaporated to leave the desired amine (0.34 g). This amine (45 mg, 0.11 mmol) was dissolved in DMF (5 mL), cooled to 0° C. and treated with triethylamine (15 μL) and catechol sulfate (20 mg, 0.12 mmol). The mixture was stirred at 0° C. for 2 hours and then at room temperature for 15 hours. The DMF was evaporated and the residue taken up in DCM (25 mL) and washed with sodium bicarbonate solution (20 mL) and water (20 mL) then dried (MgSO$_4$) and evaporated to leave an oil that was purified by preparative thin layer chromatography eluting with ethyl acetate/hexane. The resultant sulfamate ester (8 mg, 0.014 mmol) was dissolved in dioxane (0.5 mL) in a thick walled flask and treated with propylamine (4 μL, 3eq.). The flask was sealed and heated to 80μ C. for 2 hours then cooled, and the contents diluted with DCM (5 mL) and washed with 1N NaOH (3 mL), dried (MgSO$_4$) and evaporated to leave an oil that was purified by HPLC to afford the desired product. $^1$H NMR (360 MHz, CDCl$_3$) 8.47 (1H, s), 7.44 (1H, d, J=2.5 Hz), 7.32 (2H, m), 7.22 (1H, dd, J=9.0, 2.5 Hz), 7.06 (1H, d, J=9.0 Hz), 6.92 (1H, d, J=9.0 Hz), 4.78 (1H, q, J=6.5 Hz), 4.63 (1H, br d, J=7.5 Hz), 4.15 (1H, br s), 3.77 (1H, m), 3.10–3.02 (4H, m), 2.67–2.59 (2H, m), 2.54–2.48 (2H, m), 1.75–1.55 (4H, m), 1.70 (3H, d, J=6.5 Hz), 1.26–1.16 (2H, m) and 0.98 (3H, t, J=7.5 Hz). m/z (ES+)=540.

Example 30

N-[(11-endo)-5,6,7,8,9,10-hexahydro-6,9-methanobenzo[a][8]annulen-11-yl]-N'-(2,2,2-trifluoroethyl) sulfamide

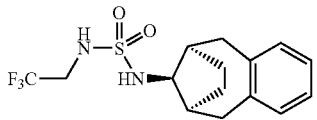

To a solution of (6R/S,9S/R)-5,6,7,8,9,10-hexahydro-6,9-methanobenzo [a][8]annulen-11-amine (100 mg) in DCM at 0° C. under nitrogen was added dropwise a solution containing 2,2,2-trifluoroethylsulfamoyl chloride* (116 mg) and triethylamine (82 μl). Allowed to warm to room temperature and stirred o/n. Added water and extracted with DCM (3×). Dried over MgSO$_4$, concentrated and purified by column chromatography on silica eluting with DCM to give the title compound as a white solid (70 mg). $^1$H NMR (360 MHz, CDCl$_3$) δ$_H$1.21 (2H, m), 1.70 (2H, m), 2.52 (2H, brm), 2.65 (2H, m), 3.05 (2H, d, J=16), 2.69–3.83 (3H, m), 4.72 (1H, brt, J=6.8), 4.81 (1H, d, J=7.8), 7.09 (4H, m).
*-prepared as in-DE 3429048

Example 31

N-cyclobutyl-N'-[(6S/R,9R/S,11R/S)-1-fluoro-5,6,7,8,9,10-hexahydro-6,9-methanobenzo[a][8]annulen-11-yl]sulfamide

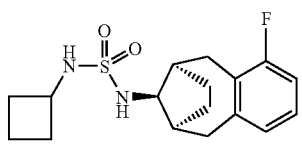

Step 1 1,2-Bis-bromomethyl-3-fluoro-benzene

3-Fluoro-o-xylene (5.05 ml, 40.3 mmol), NBS (15.8 g, 88.71 mmol) and AIBN (20 mg) in carbon tetrachloride (60 ml) were stirred and heated under reflux for 18 hours. On cooling the mixture was filtered and the filtrate was concentrated to dryness. The crude product was dissolved in methanol, a solid was precipitated out of solution at −50° C. and isolated by filtration. This procedure was repeated once to give pure dibromide 4.84 g (43%). $^1$H NMR (CDCl$_3$, 360 MHz) δ 7.26–7.32 (1H, m), 7.17 (1H, d, J=7.6 Hz), 7.05 (1H, t, J=8.6 Hz), 4.70 (2H, s), 4.63 (2H, s).

Step 2 1-(4-Fluoro-tricyclo[8.2.1.0$^{3,8}$]trideca-3(8),4,6-trien-13-ylidene)-pyrrolidinium bromide A solution of 1,2-bis-bromomethyl-3-fluoro-benzene (4.4 g, 15.6 mmol) in MeCN (10 ml) was added to stirred solution of 1-cyclopent-1-enyl-pyrrolidine (2.3 ml, 15.6 mmol) and DIPEA (5.4 ml, 31.2 mmol) in MeCN (20 ml). The mixture was stirred at room temperature for 18 hours and then filtered. Washing with cold MeCN afforded an off-white solid 1.02 g (19%). m/z 258 (M$^+$).

Step 3 4-Fluoro-tricyclo[8.2.1.0$^{3,8}$]trideca-3(8),4,6-trien-13-one oxime

The product from Step 2 (1.02 g, 3.02 mmol), hydroxylamine hydrochloride (624 mg, 9.05 mmol) and sodium acetate trihydrate (1.23 g, 9.05 mmol) in 2:1 ethanol-water (12 ml) were heated to reflux and allowed to cool to room temperature, then stirred for 18 hours at this temperature. Water (10 ml) was added and the mixture filtered. The white solid was washed with water and dried under vacuum. 590 mg (89%). m/z 220 (M+H$^+$).

Step 4 4-Fluoro-tricyclo[8.2.1.0$^{3,8}$]trideca-3(8),4,6-trien-13-ylamine

The oxime from Step 3 (590 mg, 2.69 mmol) and platinum dioxide (40 mg) in AcOH (20 ml) were hydrogenated in a Parr reactor at 30 psi for 2 hours. The mixture was filtered through Celite and the filtrate was concentrated by lyophilization to give an off-white solid. The solid was dispersed in 1N NaOH and extracted with DCM. The organic extract was dried and concentrated to dryness to give a yellow oil 525 mg (95%). m/z 206 (M+H$^+$).

Step 5 (4-Fluoro-tricyclo[8.2.1.0$^{3,8}$]trideca-3(8),4,6-trien-13-yl)-sulfamic acid 2-hydroxy-phenyl ester Catechol sulphate (332 mg, 1.93 mmol) was added to an ice-cooled solution of the amine from Step 4 (360 mg, 1.76 mmol) in THF (5 ml). The mixture was allowed to warm to room temperature, stirred for 18 hours, diluted with ethyl acetate and washed with ammonium chloride (aq) followed by brine. The organic phase was dried and evaporated to give a crude oil which was purified by column chromatography on silica gel eluting with 4:1 isohexane-ethyl acetate to give an orange oil 335 mg (51%). $^1$H NMR (CDCl$_3$, 360 MHz) δ 7.27 (1H, m), 7.21 (1H, m), 7.05 (2H, m), 6.85–7.95 (3H, m), 6.32 (1H, br s), 5.40 (1H, br d, J=7.5 Hz), 4.02 (1H, q, J=6.4 Hz), 3.19–3.25 (1H, dd, J=16.7, 7.6 Hz), 3.04 (1H, d, J=16.3 Hz), 2.70 (1H, m), 2.50–2.61 (3H, m), 1.74 (2H, m), 1.21 (2H, m). m/z 376 (M−H)$^-$ Step 6 N-cyclobutyl-N'-[(6S/R,9R/S,11R/S)-1-fluoro-5,6,7,8,9,10-hexahydro-6,9-methanobenzo[a][8]annulen-11-yl] sulfamide The product from Step 5 (335 mg, 0.889 mmol) and cyclobutylamine in 1,4-dioxane were stirred and heated in a sealed tube at 80° C. for 75 minutes. The mixture was allowed to cool to room temperature, diluted with DCM, washed with 1M NaOH solution, and the organic phase dried over sodium sulphate, filtered and concentrated. The crude product was purified by column chromatography on silica gel eluting with 4:1 isohexane-ethyl acetate to give a white solid which was subsequently triturated with diethyl ether 163 mg (54%). $^1$H NMR (CDCl$_3$, 400 MHz) δ 7.03 (1H, m), 6.86 (2H, m), 4.68 (1H, br d, J=7.5 Hz), 4.49 (1H, br d, J=8.9 Hz), 3.89 (1H, m), 3.74 (1H, m), 3.18–3.24 (1H, dd, J=16.6, 7.7 Hz), 3.09 (1H, d, J=16.0 Hz), 2.69 (1H, m), 2.49–2.61 (3H, m), 2.39 (2H, m), 1.92–2.01 (2H, m), 1.65–1.79 (4H, m), 1.13–1.25 (2H, m). m/z 339 (M+H$^+$).

Example 32

1-Cyclobutyl-3-[5-(3-morpholin-4-yl-propenyl) tricyclo[8.2.1.0$^{3,8}$]trideca-3(8),4,6-trien-13-yl]-sulfamide

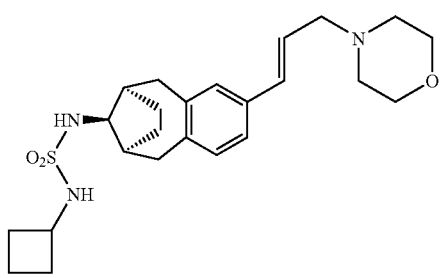

Step 1 13-Amino-tricyclo[8.2.1.0$^{3,8}$]trideca-3(8),4,6-triene-5-carboxylic acid methyl ester.

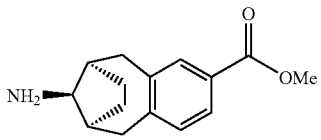

This compound was prepared by the process of Example 31 steps 2–4 (with minor modifications), starting from 3,4-bis (bromomethyl)benzoic acid methyl ester. For step 2 the reaction mixture was stirred and heated under reflux for 18 hours rather than at room temperature. For step 3 the mixture was not heated under reflux initially and the product was dried by azeotropic removal of water in toluene. For step 4 the hydrogenation was carried out under 1 atm. of hydrogen at room temperature rather than at 30 psi on a Parr hydrogenator. m/z 245 (M+H$^+$).

Step 2: 13-tert-Butoxycarbonylamino-tricyclo[8.2.1.0$^{3,8}$]trideca-3(8),4,6-triene-5-carboxylic acid methyl ester The amine from step 1 (3.0 g, 12.24 mmol) and di-tert-butyl dicarbonate (2.94 g, 13.47 mmol) in DCM (50 ml) were stirred, with ice-cooling, for 90 minutes. The reaction was quenched with N,N-dimethylethylenediamine, diluted with DCM, washed with 10% citric acid (aq), water, dried and concentrated. The crude product was purified by column chromatography on silica gel eluting with 5:1 isohexane-ethyl acetate to give a colourless oil. $^1$H NMR (CDCl$_3$, 360 MHz) δ 7.73–7.78 (2H, m), 7.16 (1H, d, J=7.8 Hz), 4.98 (1H, m), 4.03 (1H, m), 3.89 (3H, s), 3.05 (2H, m), 2.70 (2H, m), 2.53 (2H, m), 1.73 (2H, m), 1.48 (9H, s), 1.14 (2H, m).

Step 3

[5-(3-Hydroxy-propenyl)-tricyclo[8.2.1.0$^{3,8}$]trideca-3(8),4,6-trien-13-yl]-carbamic acid tert-butyl ester

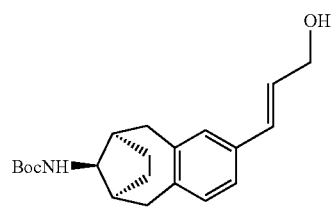

Prepared from the methyl ester of Step 2 using procedures analogous to methods described below. The ester was reduced to the benzyl alcohol (cf. Example 80), then oxidised to the aldehyde (cf. Example 81), converted to the cinnamyl ester (cf. Example 82) and reduced to the cinnamyl alcohol (cf. Example 54, Step 1).

Step 4

[5-(3-Morpholin-4-yl-propenyl)-tricyclo[8.2.1.0$^{3,8}$]trideca-3(8),4,6-trien-13-yl]-carbamic acid tert-butyl ester

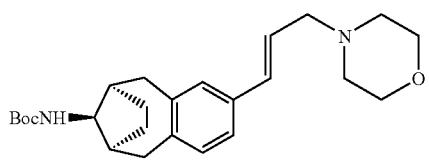

To a stirred solution of (1-bromo-2-methyl-propenyl)-dimethyl-amine (713 mg, 4.0 mmol) in dry DCM (30 ml) at 0° C. was added, via a stainless steel cannula, a solution of the cinnamyl alcohol (Step 3) (917 mg, 2.67 mmol) in dry DCM (15 ml). The mixture was allowed to warm to room temperature, and stirred for a further 1.5 h. Morpholine (1.16 g, 13.35 mmol) was added and the mixture was stirred for a further 30 min., and then quenched with water (30 ml). The aqueous phase was extracted with DCM (3×30 ml) and the combined organic phased were dried (Na$_2$SO$_4$) and concentrated to give an oil, which subjected to flash chromatography (eluent: DCM/methanol/ammonium hydroxide 97.5:2.5:0.15) gave a colourless oil (532 mg), which was used in Step 5 without further purification.

Step 5

The crude Boc-amine from Step 4 (532 mg) was treated with 4 M HCl in dioxane (20 ml) for 20 min. The solvent was removed under reduced pressure and the residual solid was triturated with chilled EtOAc and filtered. The residue was partitioned between 1 M aqueous sodium hydroxide (20 ml) and DCM (30 ml). The aqueous phase was extracted with DCM (3×30 ml) and the combined organic phases were dried (Na$_2$SO$_4$) and concentrated to give a pale yellow oil (230 mg). m/z 313 (M+H)$^+$.

The free amine (166 mg, 0.53 mmol), cyclobutyl-sulfamic acid 2-hydroxy-phenyl ester (cf. Example 117, Step 5) (188 mg, 7.73 mmol) and DMAP (50 mg) were heated to 80° C. in dry acetonitrile overnight. The solvent was removed under reduced pressure and the residue was partitioned between water (20 ml) and DCM (30 ml). The aqueous phase was extracted with DCM (2×30 ml) and the combined organic phases were dried (Na$_2$SO$_4$) and concentrated. The resulting oil was purified by flash chromatography (eluent: DCM/methanol/ammonium hydroxide 97.5:2.5:0.15) to give the title compound as a colourless oil (120 mg). $^1$H NMR (400 MHz, CDCl$_3$) δ$_H$ 1.15–1.20 (2H, m), 1.63–1.78 (3H, m), 1.91–2.01 (2H, m), 2.34–2.41 (2H, m), 2.45–2.55 (6H, br m), 2.56–2.62 (2H, m), 3.04 (1H, d, J=7.3 Hz), 3.08 (1H, d, J=7.2 Hz), 3.13 (2H, dd, J=6.8 and 0.9 Hz), 3.69–3.74 (6H, m), 3.72–3.91 (1H, m), 4.54 (1H, d, J=8.9 Hz), 4.72 (1H, d, J=7.7 Hz), 6.20 (1H, dt, J=15.8 and 6.8 Hz), 6.45 (1H, d, J=15.8 Hz), 7.01 (1H, d, J=7.6 Hz), 7.08–7.12 (2H, m). m/z 446 (M+H)$^+$.

Example 33

N-[(6S/R,9R/S,11R/S)-2-(benzyloxy)-5,6,7,8,9,10-hexahydro-6,9-methanobenzo[a][8]annulen-11-yl]-N'-cyclobutylsulfamide

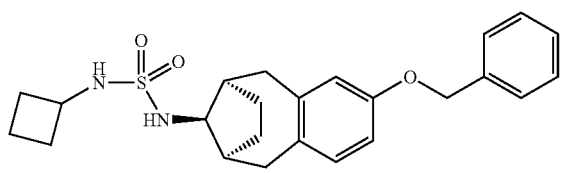

To a solution of (6R/S,9S/R,11S/R)-2-(benzyloxy)-5,6,7,8,9,10-hexahydro-6,9-methanobenzo[a][8]annulen-11-amine (prepared as in Example 17 steps 1 and 2, using the ketone from Example 26 step 1) (1.1 g) in THF (5 ml) at 0° C. was added catechol sulfate (0.6 g) in one portion. The reaction was allowed to warm to room temperature and stirred o/n, then quenched with ammonium chloride and extracted with EtOAc (3×). After drying over MgSO$_4$ and evaporation, the crude product was chromatographed using silica eluting with 30% 5:1 EtOAc:DCM in hexane to give 2-hydroxyphenyl (6R/S,9S/R,11S/R)-2-(benzyloxy)-5,6,7,8,9,10-hexahydro-6,9-methanobenzo[a][8]annulen-11-ylsulfamate as a glassy solid (1.35 g). This sulfamate (300 mg), dioxane (4 ml) and cyclobutylamine (0.17 ml) were heated in a sealed tube at 80° C. for 5 hrs. Upon cooling, 1M NaOH was added and the mixture extracted with EtOAc (3×). After drying over MgSO$_4$ and evaporation, the crude product was chromatographed using silica eluting with 25% 5:1 EtOAc:DCM in hexane to give the title compound as a white solid (188 mg). $^1$H NMR (360 MHz, CDCl$_3$) δ$_H$ 1.21 (2H, m), 1.73 (4H, m), 1.95 (2H, m), 2.34–2.60 (6H, m), 3.00 (1H, d, J=15.9), 3.07 (1H, d, J=15.9), 3.73 (1H, m), 3.88 (1H, m), 4.40 (1H, d, J=8.9), 4.62 (1H, d, J=8.8), 5.02 (2H, s), 6.71 (2H, m), 6.98 (1H, d, J=8.1), 7.38 (5H, m).

Example 34

N-[(6S/R,9R/S,11R/S)-2-(benzyloxy)-5,6,7,8,9,10-hexahydro-6,9-methanobenzo[a][8]annulen-11-yl]-N'-(2,2,2-trifluoroethyl)sulfamide

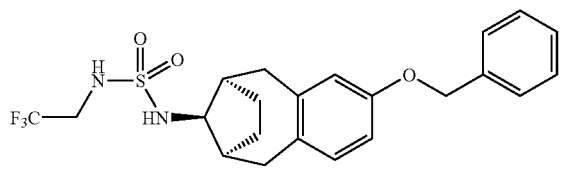

Prepared as in Example 33, replacing cyclobutylamine with 2,2,2-trifluoroethylamine. $^1$H NMR (360 MHz, CDCl$_3$) δ$_H$ 1.23 (2H, m), 1.67 (2H, m), 2.50 (4H, m), 2.97 (1H, d, J=15.8), 3.03 (1H, d, J=15.9), 3.66 (2H, m), 3.74 (1H, m), 5.02 (3H, m), 6.71 (2H, m), 6.98 (1H, d, J=8.1), 7.31 (5H, m).

Example 35

N-cyclobutyl-N'-[(6S/R,9S/R,11S/R)-2-(2-morpholin-4-ylethoxy)-5,6,7,8,9,10-hexahydro-6,9-methanobenzo[a][8]annulen-11-yl]sulfamide hydrochloride

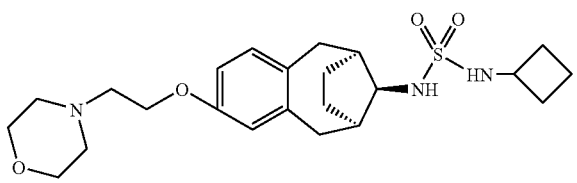

Step 1:

Ethyl bromoacetate (8.01 g) was added to a stirred solution of [6S/R,9R/S]2-Hydroxy-5,6,7,8,9,10-hexahydro-6,9-methanobenzo[a][8]annulen-11-one (9.7 g; J. Org. Chem 1982, 47, 4329) and potassium carbonate (6.6 g) in dry DMF (150 mL). The reaction was warmed to 90° C. for 18 hours, cooled to room temperature, diluted with water (200 mL), and extracted into ether (4×100 mL). The organic extracts were washed with water (100 mL), brine (100 mL), dried over MgSO$_4$, filtered and the solvent removed under reduced pressure. Flash chromatography over silica (200–400 mesh, 0–30% EtOAc/isoHexane) afforded (13-oxo-tricyclo[8.2.1.0$^{3,8}$]trideca-3,5,7-trien-5-yloxy)-acetic acid ethyl ester (11.07 g) $^1$H NMR (CDCl$_3$ 400 MHz) δ 1.28 (3H, m), 1.84 (2H, m), 2.58 (2H, m), 2.86 (4H, m), 4.15 (2H, m), 4.22 (2H, m), 4.59 (2H, s), 6.71 (1H, dd, J=8.0, 4.0 Hz), 6.80 (1H, d, J=4.0 Hz), 7.10 (1H, d, J=8.0 Hz).

Step 2:

The product recovered from Step 1 (11.07 g) was converted to (13-amino-tricyclo[8.2.1.0 $^{3,8}$]trideca-3,5,7-trien-5-yloxy)-acetic acid ethyl ester using the method of Example 17, Steps 1 and 2. The recovered amine (7.4 g) was taken up in dry DCM (100 mL) and treated with di-$^t$butyldicarbonate (5.6 g). After 24 hrs the reaction was diluted with water, the organic layer separated, dried over MgSO$_4$, filtered and the solvent removed under reduced pressure to give a clear oil. Purification by flash chromatography over silica (200–400 mesh, 30% EtOAc/isoHexane) gave (13-tert-Butoxycarbonylamino-tricyclo[8.2.1.0 $^{3,8}$]trideca-3,5,7-trien-5-yloxy)-acetic acid ethyl ester as a white solid (5.7 g). $^1$H NMR (CDCl$_3$ 400 MHz), δ 1.19 (2H, m), 1.27 (3H, t, J=8.0 Hz), 1.52 (9H, s), 1.68 (2H, m), 2.5 (4H, m), 2.94 (2H, m), 4.16 (1H, brm), 4.25 (2H, q, J=8.0 Hz), 4.57 (2H, s), 4.99 (1H, brm), 6.17 (1H, dd, J=8.0, 1.0 Hz), 6.67 (1H,d, J=1.0 Hz), 6.98 (1H, d, J=8.0 Hz).

Step 3:

Lithium borohydride (56 mg) was added in a single portion to a stirred solution of the product from Step 2 (1.0 g) in dry THF. (20 mL). The resulting solution was stirred at room temperature for 18 hrs, quenched with NH$_4$Cl (aq. sat$^d$ 50 mL) and extracted into DCM. The organic extract was dried over MgSO$_4$, filtered and the solvent removed under reduced pressure and the product purified by flash chromatography over silica (200–400 mesh, 10–60% EtOAc/isohexane) to give [5-(2-hydroxy-ethoxy)tricyclo [8.2.1.0$^{3,8}$]trideca-3,5,7-trien-13-yl]-carbamic acid tert-butyl ester as a white solid (340 mg). $^1$H NMR (CDCl$_3$ 400 MHz), δ 1.20 (2H, m), 1.47 (9H, s), 1.69 (2H, m), 2.04 (1H, m), 2.50 (4H, m), 2.96 (2H, m), 3.94 (2H, m), 4.05 (3H, m), 4.99 (1H, brm), 6.62 (1H, dd, J=8.0, 1.0 Hz), 6.67 (1H, d, J=1.0 Hz), 6.98 (1H, d, J=8.0 Hz).

Step 4:

Trifluoromethanesulfonic anhydride (162 μL) was added to a solution of the product from Step 3 (340 mg) and 2,6 di-$^t$butyl-4-methypyridine (198 mg) in dry DCM at −78° C. After 30 mins, excess morpholine was added and the reaction allowed to warm to room temperature over 4 hours. The reaction was quenched with NH$_4$Cl (aq. sat$^d$ 50 mL) and extracted into DCM. The organic extract was dried over MgSO$_4$, filtered and the solvent removed under reduced pressure. The recovered material was treated with 20% TFA/DCM for 3 hours, basified with NaHCO$_3$ (aq. sat$^d$), the organic layer separated, dried over MgSO$_4$, filtered and the solvent removed under reduced pressure. Product purified by flash chromatography over silica (200–400 mesh, 3% 2N NH$_3$/MeOH/DCM) to give 5-(2-morpholin-4-yl-ethoxy)-tricyclo[8.2.1.0$^{3,8}$]trideca-3,5,7-trien-13-ylamiine (190 mg). $^1$H NMR (CDCl$_3$ 400 MHz), δ 1.17 (2H, m), 1.67 (4H, m), 2.24 (2H, m), 2.45 (2H, M), 2.56 (4H, m), 2.76 (2H, m), 3.17 (2H, m), 3.36 (1H, m), 3.73 (4H, m), 4.05 (2H, m), 6.61 (1H, dd, J=8.0, 1.0 Hz), 6.65 (1H, d, J=1.0 Hz), 6.96(1H, d, J=8.0 Hz).

Step 5:

Cyclobutyl-sulfamic acid 2-hydroxy-phenyl ester (prepared as in Example 117, Step 5) (167 mg) was added to a stirred solution of the product from Step 4 (182 mg) and DMAP (cat) in dry CH$_3$CN (10 mL) and the resulting solution warmed to reflux for 18 hrs. After this time the solvent was removed under reduced pressure, and flash chromatography of the residue over silica (200–400 mesh, 3% 2N NH$_3$/MeOH/DCM) gave the product as a gum. Treatment with ethereal HCl and trituration with ether afforded N-cyclobutyl-N'-[(6S/R,9S/R,11S/R)-2-(2-morpholin-4-ylethoxy)-5,6,7,8,9,10-hexahydro-6,9-methanobenzo[a][8]annulen-11-yl]sulfamide hydrochloride as a white powder (40 mg). m/z ES+(M+H)$^+$450.

Example 36

1-Cyclobutyl-3-[5-(3-morpholin-4-yl-propyl)-tricyclo[8.2.1.03,8]trideca-3(8),4,6-trien-13-yl]-sulfamide

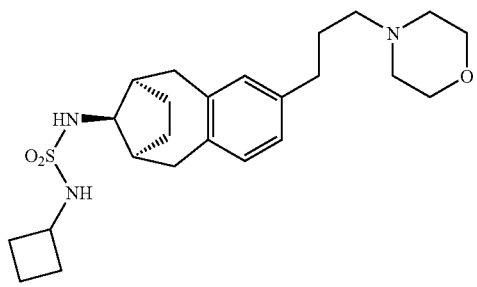

The product of Example 32 (as the hydrochloride) (30 mg, 0.06 mmol) and 10% Pd/C (10 mg) were suspended in methanol (3 ml) and stirred under a hydrogen atmosphere for 2 h. The mixture was filtered, and the filtrate concentrated to dryness and the residual solid was partitioned between DCM (10 ml) and saturated NaHCO$_3$(aq) (5 ml). The aqueous phase was extracted with DCM (3×10 ml), the combined organic phases were dried (Na$_2$SO$_4$) and concentrated. Purification by flash chromatography (eluant: DCM/MeOH/ammonium hydroxide 97.5:2.5:0.15) gave a white solid (18 mg). $^1$H NMR (400 MHz, CDCl$_3$) δ$_H$ 1.16–1.24 (2H, m), 1.61–1.82 (6H, m), 1.90–2.01 (2H, m), 2.33–2.49 (10H, m), 2.53–2.61 (4H, m), 3.03 (1H, d, J=13 Hz), 3.06 (1H, d, J=13 Hz), 3.70–3.75 (5H, m), 3.85–3.91 (1H, m), 4.50 (1H, d, J=8.9 Hz), 4.67 (1H, d, J=7.9 Hz), 6.89–6.90 (2H, m), 6.98 (1H, d, J=8.12 Hz). m/z 448 (M+H)$^+$ Example 37

N-[(6S/R,9R/S,11R/S)-2-(2-morpholin-4-ylethoxy)-5,6,7,8,9,10-hexahydro-6,9-methanobenzo[a][8]annulen-11-yl]-N'-(2,2,2-trifluoroethyl)sulfamide

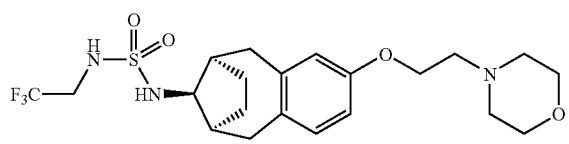

Prepared from the amine from Example 35 Step 4 by coupling with 2,2,2-trifluoroethylsulfamoyl chloride, following the procedure of Example 38 Step 2.

MW for MH+=478.

Example 38

N-[{(6S/R,9R/S,11R/S)-2-[(1E)-3-morpholin-4-yl-prop-1-enyl]-5,6,7,8,9,10-hexahydro-6,9-methanobenzo[a][8]annulen-11-yl}-N'-(2,2,2-trifluoroethyl) sulfamide

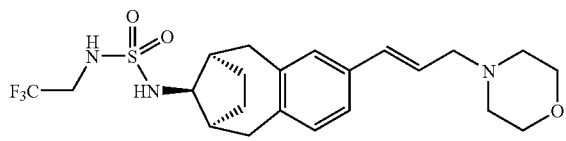

Step 1: 3-(13-Amino-tricyclo[8.2.1.03,8]trideca-3(8),4,6-trien-5-yl)-acrylic acid methyl ester.

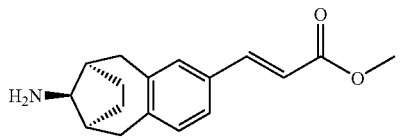

Prepared as in Example 32 Steps 1–3, omitting the final reduction, followed by removal of the Boc group by treatment of the Boc-amine (1.2 g) in DCM (5 ml) with 4M HCl in 1,4-dioxane (10 ml), and stirring the resulting solution at room temperature for 4 hours. After this time the reaction mixture was concentrated in vacuo giving an off-white solid. This solid was dissolved in 50 ml of de-ionised water and was neutralised using sat. NaHCO$_3$ solution. The resulting solution was extracted with DCM (2×50 ml) and the organics combined, dried over MgSO$_4$ and solvent removed in vacuo yielding the title compound as a white solid (870 mg).
MS (ES+) 272 [M+H]$^+$.

Step 2: methyl (2E)-3-[(6R/S,9S/R,11S/R)-11-({[(2,2,2-trifluoroethyl)amino]sulfonyl}amino)-5,6,7,8,9,10-hexahydro-6,9-methanobenzo[a][8]annulen-2-yl]prop-2-enoate.

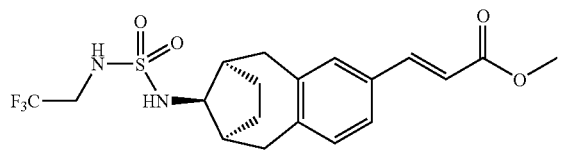

A mixture the product from Step 1 (330 mg), pyridine (1.9 ml), DMAP (7.4 mg) and 2,2,2-trifluoroethylsulfamoyl chloride (265 mg) in DCM (12 ml) was stirred at room temperature for 16 hours. The reaction mixture was diluted with DCM (75 ml) and washed with 1M HCl solution (50 ml) and then with saturated brine (50 ml). The organics were separated, dried over MgSO$_4$ and concentrated in vacuo giving a pale oil. This oil was purified by flash column chromatography on silica using 25% EtOAc in isohexane as eluant. The title compound was isolated as a white foam requiring no further purification (385 mg). (400 MHz $^1$H, δ-CDCl$_3$), 1.18–1.20 (2H, m), 1.69–1.72 (2H, m), 2.52–2.54 (2H, m), 2.61–2.68 (2H, m), 3.05 (1H, d, J=2.6 Hz), 3.09 (1H, d, J=2.4 Hz), 3.69–3.74 (2H, m), 3.75 (1H, m), 3.80 (3H, s), 4.90 (1H, t), 4.97 (1H, d), 6.37–6.41 (1H, J=16 Hz), 7.09–7.11 (1H, d), 7.23–7.27 (2H, m), 7.61–7.65 (1H, d, J=16 Hz).
MS (ES+) 433 [M+H]$^+$.

Step 3: N-{(6R/S,9S/R,11S/R)-2-[(1E)-3-hydroxyprop-1-enyl]-5,6,7,8,9,10-hexahydro-6,9-methanobenzo[a][8]annulen-11-yl}-N'-(2,2,2-trifluoroethyl)sulfamide

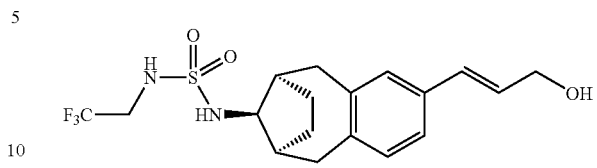

To a solution of the product from Step 2 (121 mg) in toluene (5 ml) at −78° C. was added 1M DIBAL-H solution in toluene (1.12 ml). The mixture was stirred at −78° C. for 2 hours before quenching with methanol (3 ml) and the temperature was allowed to rise to room temperature. The reaction mixture was then diluted with EtOAc (50 ml) and washed successively with 1M HCl solution (50 ml), dilute NaHCO$_3$ (50 ml) and saturated brine (50 ml). The organics were separated, dried over MgSO$_4$ and evaporated to dryness giving a foaming solid. This was purified by flash chromatography on silica using 20% EtOAc in isohexane as eluant, giving the title compound as a white foam (112 mg).
400 MHz $^1$H, δ-CDCl$_3$, 1.17 (2H, m), 1.68–1.70 (2H, m), 2.48–2.52 (2H, m), 2.56–2.63 (2H, m), 3.00 (1H, d, J=3.52 Hz), 3.05 (1H, d, J=3 Hz), 3.66–3.70 (2H, m), 3.75–3.77 (1H, m), 4.29–4.30 (2H, dd), 5.02–5.04 (1H, t), 5.05–5.07 (1H, d), 6.27–6.34 (1H, m), 6.51–6.55 (1H, d, J=15.9 Hz), 7.00–7.12 (3H, m). MS (ES+) 405 [M+H]$^+$.

Step 4:

The product from Step 3 (60 mg) was dissolved in DCM (5 ml) and cooled to −20° C. before dropwise addition of 1M PBr$_3$ in DCM (150 μl). Once addition was completed the temperature was allowed to rise to room temperature over 1 hour. The reaction mixture was re-cooled to −20° C. before dropwise addition of morpholine (280 μl), then the temperature in the flask was allowed to rise to room temperature over 2 hours. Evaporation to dryness, then purification by column chromatography using 65% EtOAc in isohexane as eluant, gave the title compound as a slowly crystallising oil (15.6 mg).
(400 MHz $^1$H, δ-CDCl$_3$), 1.22–1.24 (2H, m), 1.68–1.72 (2H, m), 2.48–2.58 (6H, m), 2.55–2.65 (2H, m), 3.02–3.06 (2H, m), 3.15 (2H, d), 4.70–4.80 (7H, m), 4.70–4.75 (2H, m), 6.18–6.26 (1H, m), 6.46–6.52 (1H, d), 7.01–7.05 (1H, d), 7.08–7.15 (2H, m). MS (ES+) 474 [M+H]$^+$.

Example 39

Methyl [6S/R,9R/S,11R/S]-11-{[(2,2,2-trifluoroethylamino)sulfonyl]amino}-5,6,7,8,9,10-hexahydro-6,9-methanobenzo[a][8]annule-2-carboxylate

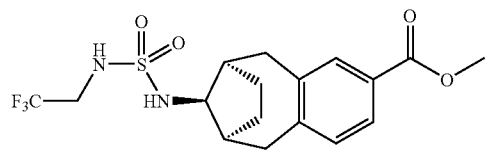

A solution of 2,2,2-trifluoroethylsulfamoyl chloride (0.91 g) in DCM (5 mL) was added dropwise at 0° C. to a stirred solution of the amine from Step 1 of Example 32 (1.02 g) and triethylamine in DCM (10 mL). After 24 hours the solution was diluted with DCM (20 mL) and washed with 1M citric acid (20 mL) and brine (20 mL). The organic layer was dried over Na$_2$SO$_4$, filtered and concentrated. The residue was purified by filtration through silica gel, eluting with ethyl acetate, to give the title sulfamide (1.55 g, 92%) as a white foam, δ ($^1$H, 360 MHz, CDCl$_3$) 1.16–1.23 (2H, m), 1.70–1.74 (2H, m), 2.50–2.60 (2H, m), 2.68–2.77 (2H, m), 3.09 (2H, dd, J=16, 9), 3.70–3.82 (3H, m), 3.90 (3H, s), 4.78 (1H, t, J=7), 4.84 (1H, d, J=7), 7.16 (1H, d, J=8), 7.75–7.77 (3H, m); MS (ES+) 407 ([MH]$^+$).

Example 40

N-{(6S/R,9R/S,11R/S)-2-[5-(4-Fluorophenyl)-1,3,4-oxadiazol-2-yl]-5,6,7,8,9,10-hexahydro-6,9-methanobenzo[a][8]annulen-11-yl}-N'-(2,2,2-trifuoroethyl)sulfamide

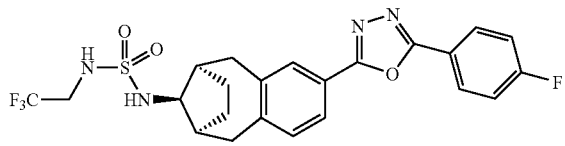

Step 1: [6S/R,9R/S,11R/S]-11-{[(2,2,2-Trifluoroethylamino)sulfonyl]amino}-5,6,7,8,9,10-hexahydro-6,9-methanobenzo[a][8]annule-2-carboxylic acid

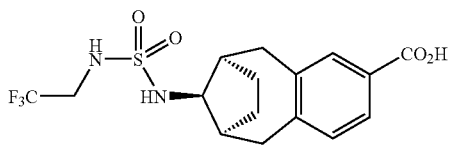

A mixture of the ester from Example 39 (1.55 g) and lithium hydroxide (0.5 g) in tetrahydrofuran-water (2:1, 15 mL) was stirred for 18 hours at room temperature. The solution was diluted with water (50 mL), acidified with 1M HCl and extracted with ethyl acetate (50 mL). The extract was dried over Na$_2$SO$_4$, filtered and concentrated to give the acid (1.48 g, 99%) as a white foam, MS (ES+) 393 ([MH]$^+$).

Step 2:
A solution of the acid from Step 1 (0.125 g), diisopropylethylamine (0.07 mL), HBTU (0.15 g) and 4-fluorobenzhydrazide (0.06 g) in acetonitrile (4 mL) was stirred at 40° C. for 18 hours. The mixture was diluted with water (20 mL) and the white solid was collected, redissolved in ethyl acetate, dried over Na$_2$SO$_4$, filtered and concentrated. The resulting white solid (0.088 g) and Burgess reagent (0.17 g) was dissolved in tetrahydrofuran (2 mL) and subjected to microwave irradiation (120° C., 240 seconds, Smith Personal Synthesiser microwave reactor). Flash column chromatography on silica, eluting with 40% ethyl acetate-isohexanes, then preparative thin-layer chromatography, eluting with 20% ethyl acetate-isohexanes, gave the title sulfamide (0.006 g, 7%) as a white solid, δ ($^1$H, 360 MHz, CDCl$_3$) 1.17–1.28 (2H, m), 1.73–1.77 (2H, m), 2.58–2.64 (2H, m), 2.70–2.81 (2H, m), 3.15 (2H, d, J=16), 3.72–3.92 (3H, m), 4.97–5.06 (2H, m), 7.20–7.25 (3H, m), 7.82 (2H, d, J=8), 7.86 (1H, s), 8.13–8.16 (2H, m); MS (ES+) 511 ([MH]$^+$).

Example 41

N-[(6S/R,9R/S,11R/S)-2-(5-Phenyl-1,3,4-oxadiazol-2-yl)-5,6,7,8,9,10-hexahydro-6,9-methanobenzo[a][8]annulen-11-yl]-N'-(2,2,2-trifluoroethyl)sulfamide

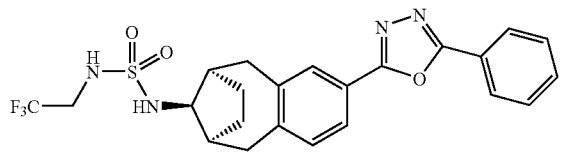

Prepared as described for Example 40, using benzhydrazide in place of 4-fluorobenzhydrazide in Step 2 to give the title sulfamide (0.042 g, 27%) as a white solid, δ ($^1$H, 360 MHz, CDCl$_3$) 1.20–1.30 (2H, m), 1.72–1.80 (2H, m), 2.55–2.63 (2H, m), 2.70–2.85 (2H, m), 3.15 (2H, d, J=16), 3.72–3.82 (3H, m), 4.72 (1H, t, J=7), 4.80 (1H, d, J=7) 7.27 (1H, d, J=8), 7.54–7.56 (3H, m), 7.86 (1H, d, J=8), 7.90 (1H, s), 8.13–8.16 (2H, m); MS (ES+) 493 ([MH]$^+$).

Example 42

N-(2,2,2-trifluoroethyl)-N'-((6S/R,9R/S,11R/S)-2-(1E)-3-[4-(trifluoromethyl)piperidin-1-yl]prop-1-enyl}-5,6,7,8,9,10-hexahydro-6,9-methanobenzo[a][8]annulen-11-yl)sulfamide

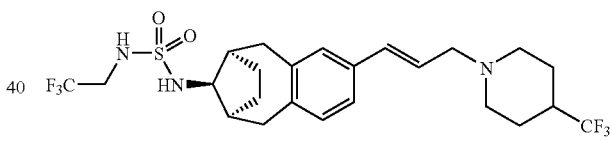

Prepared by the procedure of Example 38, substituting 4-trifluoromethylpiperidine for morpholine. MS (ES+) 540 [M+H]$^+$.

Example 43

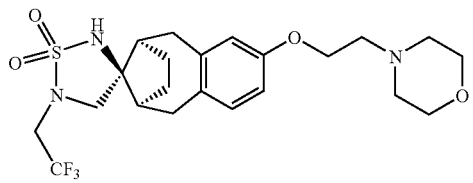

Step 1:
A solution of the product from Example 65 (5.46 g) in THF (20 ml) was added dropwise to NaH (0.61 g) in THF (20 ml) at 0° C. under nitrogen. The reaction was stirred for 30 min then MOM chloride (1.0 ml) was added. The reaction was allowed to warm to room temperature with stirring for 1 hr. Added water (40 ml) and extracted with EtOAc (3×50 ml). The combined organic phases were washed with brine (50 ml). Drying, concentration and column chromatography on silica eluting with 10% EtOAc/hexane gave the MOM-protected sulfamide (5.82 g, 97%). $^1$H NMR (360 MHz, CDCl$_3$) $\delta_H$ 1.33 (2H, m), 1.63 (2H, m), 2.56–2.73 (4H, m), 3.34–3.44 (4H, m), 3.41 (3H, s), 3.69 (2H, dq, J=1.4, 8.8), 4.95 (2H, s), 5.03 (2H, s), 6.72 (2H, m), 6.98 (1H, d, J=7.7), 7.37 (5H, m).

Step 2:

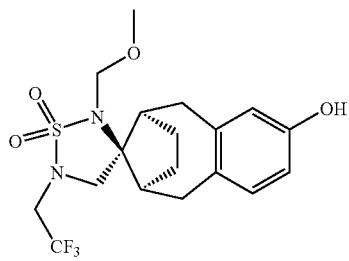

To a degassed solution of the MOM-protected sulfamide (4.53 g) in ethanol/EtOAc (1:1; 300 ml) was added 10% palladium on carbon (0.7 g). The mixture was hydrogenolysed at 50 psi for 18 hrs, filtered and concentrated to give the phenol (3.66 g, 98%).

Step 3:

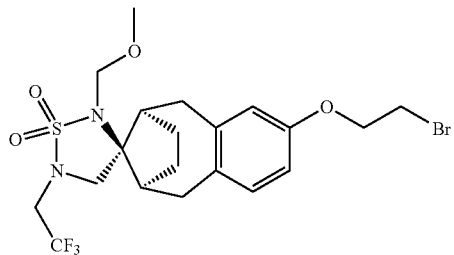

A mixture of the product from Step 2 (420 mg), potassium carbonate (276 mg) and 1,2-dibromoethane (0.43 ml) in acetone (20 ml) was heated under reflux for 6 hr. Then potassium carbonate (276 mg) and 1,2-dibromoethane (0.43 ml) were added and the reaction heated under reflux overnight. The reaction was allowed to cool, concentrated then partitioned between ethyl acetate and water. The aqueous layer was extracted with ethyl acetate (x2) and the combined organic extracts were washed with brine, then dried (MgSO$_4$), filtered and evaporated. The residue was purified by chromatography on silica gel eluting with 10–40% EtOAc/hexane to give the bromide (222 mg, 42%). $^1$H NMR (360 MHz, CDCl$_3$) $\delta_H$ 1.31 (2H, m), 1.64 (2H, m), 2.57–2.72 (4H, m), 3.34–3.44 (4H, m), 3.41 (3H, s), 3.63 (2H, t, J=6.3), 3.69 (2H, dq, J=1.8, 8.8), 4.27 (2H, t, J=6.3), 4.95 (2H, s), 6.66 (2H, m), 6.98 (1H, d, J=8.0).

Step 4:

A mixture of the product from Step 3 (50 mg), potassium carbonate (16 mg), potassium iodide (16 mg) and morpholine (10 mg) in acetonitrile (2 ml) was stirred at rt for 3 days. Water was added and the reaction was extracted with ethyl acetate (x3). The combined organic extracts were washed with brine, dried (MgSO$_4$), filtered and evaporated. The residue was purified by chromatography on silica gel eluting with DCM-2% MeOH/DCM then redissolved in DCM and stirred at rt with two drops of TFA for 1 hr. The reaction was concentrated to give the desired product (25 mg, 44%). $^1$H NMR (360 MHz, MeOH) $\delta_h$ 1.20 (2H, m), 1.73 (2H, m), 2.42 (2H, m), 2.59 (2H, m), 3.19–3.68 (8H, m), 3.62 (2H, t, J=4.9), 3.80 (2H, m), 3.84 (2H, q, J=9.2), 4.06 (2H, m), 4.35 (2H, t, J=4.9), 6.76 (2H, m), 7.04 (1H, d, J=8.1). MS(ES+) 490, MH$^+$.

Example 44

[6S/R,9R/S,11 R/S] 2',3',4',5,5',6,7,8,9,10-decahydro-2-hydroxy-5'-propylspiro[6,9-methanobenzocyclooctene-11,3'-[1,2,5]thiadiazole]1',1'-dioxide

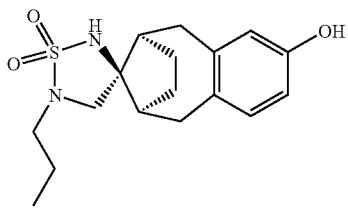

To a degassed solution of the product of Example 27 (7.6 g) in methanol/EtOAc (1:1; 300 ml) was added 10% palladium on carbon (1.3 g). The mixture was hydrogenolysed at 50 psi for 4 hrs, filtered and concentrated to give the title compound as a white foam (5.5 g). $^1$H NMR (d$_6$-DMSO 360 MHz) $\delta_H$ 0.90 (3H, t, J=7.2), 1.03 (2H, m), 1.55 (2H, m), 1.63 (2H, m), 2.24 (2H, brm), 2.40 (2H, m), 2.87 (2H, t, J=7.1), 3.04 (1H, d, J=15.6), 3.10 (1H, d, J=15.6), 3.14 (2H, s), 6.47 (2H, m), 6.84 (1H, d, J=8), 7.60 (1H, s), 9.00 (1H, s).

Example 45

[6S/R,9R/S,11R/S] 2',3',4',5,5',6,7,8,9,10-decahydro-2-(2-(4-fluorophenoxy)ethoxy)-5'-propylspiro[6,9-methanobenzocyclooctene-11,3'-[1,2,5]thiadiazole] 1',1'-dioxide

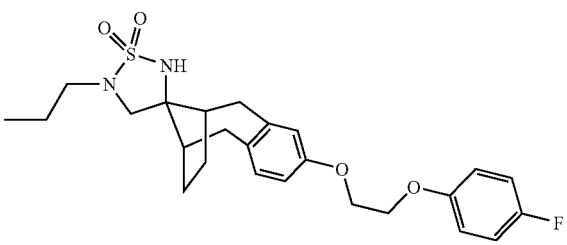

The phenol from Example 44 (180 mg), K$_2$CO$_3$ (223 mg) and 4-fluorophenoxyethyl bromide (129 mg) in DMF (5 ml) were heated to 50° C. for 24 hrs. Added water (30 ml) and extracted with EtOAc (3×20 ml). The combined organic phases were washed with water (2×30 ml), NaOH (1M, 50 ml), brine, then dried and concentrated in vacuo. The resultant gum was purified using HPLC to give the title ether (27 mg, 11%) a white solid, (360 MHz $^1$H, δ-CDCl$_3$) 0.98 (3H, t, J=7.3), 1.29 (2H, m), 1.66 (4H, m), 2.39 (2H, m), 2.60 (2H, m), 3.01 (2H, t, J=7.1), 3.09 (1H, d, J=15.9), 3.19 (3H, m), 4.27 (4H, s), 4.71 (1H, s), 6.69 (2H, m), 6.88 (2H, m), 6.97 (3H, m);

MS(ES+): 475 ([MH]$^+$).

Example 46

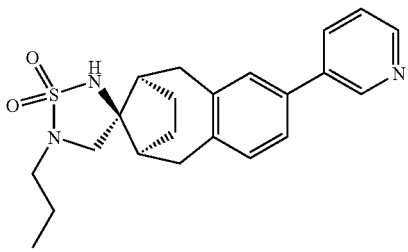

A solution of the triflate (60 mg) from Example 51 (first step) and pyridine-3-boronic acid-1,3-propanediol cyclic ester (25 mg) in DME (2 ml) and 2M sodium carbonate (0.5 ml) was degassed and then Pd(PPh$_3$)$_4$ (4 mg) was added. The mixture was heated at 80° C. under nitrogen for 4 hrs, allowed to cool, water added and then extracted with EtOAc (3×). After evaporation, the crude material was purified by column chromatography on silica eluting with 50% EtOAc/hexane to give the product which was then dissolved in Et$_2$O/MeOH, cooled to 0° C. and bubbled with HCl for 5 mins. Concentration and trituration with Et$_2$O gave the title compound as a white powder (39 mg). $^1$H NMR (d$_6$-DMSO 360 MHz) δ$_H$ 0.91 (3H, t, J=7.3), 1.06 (2H, m), 1.56 (2H, m), 1.71 (2H, brm), 2.36 (2H, brs), 2.71 (2H, m), 2.90 (2H, t, J=7.1), 3.24 (4H, m), 7.30 (1H, d, J=7.1), 7.61 (1H, d, J=7.0), 7.66 (1H, s), 7.74 (1H, s), 8.02 (1H, dd, J=5.1, 7.2), 8.81 (2H, m), 9.21 (1H, s).

Example 47

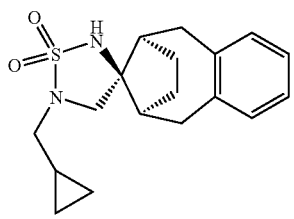

Prepared as in Example 21, using cyclopropyl methyl iodide instead of n-butyl iodide. $^1$H NMR (360 MHz, CDCl$_3$) δ$_H$ 0.24 (2H, m), 0.60 (2H, m), 1.03 (1H, m), 1.28 (2H, m), 1.69 (2H, m), 2.45 (2H, m), 2.67 (2H, dd, J=7.7, 16), 2.94 (2H, d, J=6.9), 3.19 (2H, d, J=15.9), 3.31 (2H, s), 4.81 (1H, s), 7.10 (4H, m).

Example 48

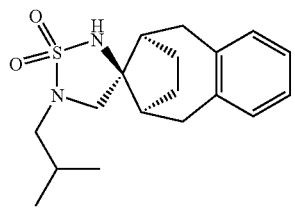

Prepared as in Example 21, using 1-bromo-2-methylpropane instead of n-butyl iodide. $^1$H NMR (360 MHz, CDCl$_3$) δ$_H$ 0.98 (6H, d, J=6.6), 1.29 (2H, m), 1.66 (2H, m), 1.87 (1H, m), 2.41 (2H, m), 2.67 (2H, dd, J=7.7, 16.1), 2.84 (2H, d, J=6.9), 3.19 (2H, d, J=16.7), 3.21 (2H, s), 4.69 (1H, s), 7.10 (4H, m).

Example 49

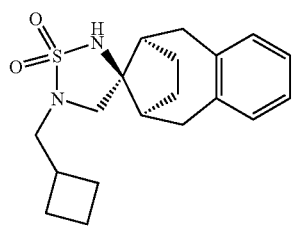

Prepared as in Example 21, using bromomethylcyclobutane instead of n-butyl iodide. $^1$H NMR (360 MHz, CDCl$_3$) δ$_H$ 1.27 (2H, m), 1.63–1.97 (6H, m), 2.09 (2H, m), 2.41 (2H, m), 2.54–2.70 (3H, m), 3.07 (2H, d, J=7.5), 3.18 (4H, m), 4.72 (1H, s), 7.09 (4H, m).

Example 50

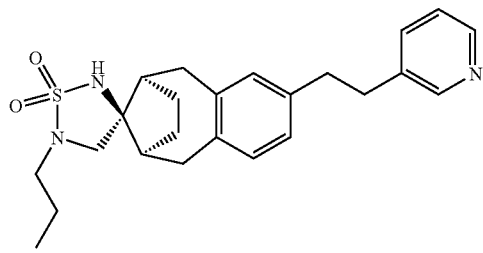

A mixture of the phenol from Example 44 (50 mg), 3-picolyl chloride (29 mg) and potassium carbonate (62 mg) in DMF was stirred o/n at room temperature. Added water and extracted with EtOAc (x3), then washed the combined organic phases with water and brine. Dried over MgSO$_4$, evaporated and purified by HPLC to give the desired compound as the triflate salt. $^1$H NMR (360 MHz, CDCl$_3$) δ$_H$ 0.98 (3H, t, J=7.3), 1.27 (2H, m), 1.66 (4H, m), 2.41 (2H, m), 2.63 (2H, m), 3.02 (2H, t, J=7.2), 3.10 (1H, d, J=15.9), 3.21 (3H, m), 4.78 (1H, s), 5.21 (2H, s), 6.71 (2H, m), 7.03 (1H, d, J=8.2), 7.86 (1H, m), 8.38 (1H, d, J=8), 8.80 (2H, m), 8.89 (1H, s).

Example 51

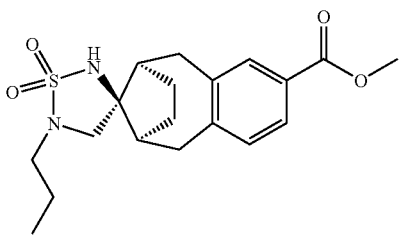

Step 1

To a suspension of the phenol from example 44 (6.1 g) in DCM (100 ml) cooled to 0° C. were added dropwise trifluoromethane sulfonic anhydride (4.5 ml) and pyridine (2.2 ml) and the reaction allowed to warm to room temperature with stirring for 2 hrs. Added water and extracted with DCM (3×), dried (MgSO$_4$), filtered and concentrated. Trituration with ether/hexane gave the triflate (8 g) as a white powder.

Step 2

This triflate (6 g) was dissolved in dimethylsulfoxide/methanol (240:150 ml) and triethylamine (23 ml) and then degassed for 15 mins. 1,3-Bis(diphenylphosphino)propane (527 mg) and palladium acetate (287 mg) were added, the solution saturated with carbon monoxide and then heated to 85° C. for 4 hrs, bubbling carbon monoxide into the reaction mixture continuously. Allowed to cool, added water and extracted with EtOAc (x3), washed with water and brine, dried and filtered. Concentration in vacuo, then chromatography on silica eluting with 2–4% EtOAc:DCM gave the desired compound as a white powder (4.06 g). $^1$H NMR (360 MHz, CDCl$_3$) $\delta_H$ 0.97 (3H, t, J=7.3), 1.24 (2H, m), 1.68 (5H, m), 2.45 (2H, brs), 2.76 (2H, m), 3.02 (2H, t, J=7.2), 3.22 (4H, m), 3.90 (3H, s), 4.89 (1H, s), 7.16 (1H, m), 7.77 (2H, m).

Example 52

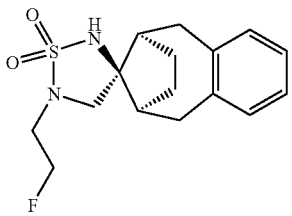

A mixture of the product of Example 18 Step 1 (300 mg), caesium carbonate (490 mg) and ethyl bromoacetate (168 μl) in DMF (3 ml) was stirred o/n at room temperature. Added water, extracted with EtOAc (3×) and washed the combined organic extracts with water and brine. Dried, concentrated and triturated with ether to give a white solid (175 mg), a quantity of which (150 mg) was dissolved in THF (5 ml). The solution was cooled to 0° C. under nitrogen and 1M LAH in THF (0.43 ml) was added dropwise and the reaction was stirred at this temperature for 15 mins. After standard workup (water, NaOH, water), the mixture was extracted with EtOAc (3×), dried and evaporated. Trituration with ether gave a white powder (90 mg), a quantity of which (65 mg) was dissolved in DCM (2 ml), cooled to 0° C. and diethylaminosulfur trifluoride (35 μl) was added dropwise and the reaction stirred for 15 mins. Poured onto ice-chilled saturated NaHCO$_3$ and extracted with DCM (3×). Dried and evaporated then purified by column chromatography on silica eluting with 25% EtOAc:hexane, giving the desired compound as a white powder (25 mg). $^1$H NMR (360 MHz, CDCl$_3$) $\delta_H$ 1.26 (2H, m), 1.69 (2H, m), 2.44 (2H, m), 2.67 (2H, dd, J=7.6, 16.0), 3.19 (2H, d, J=16.0), 3.38 (2H, s), 3.40 (2H, dt, J=4.6, 27.6), 4.66 (2H, dt, J=4.6, 47.2), 4.82 (1H, s), 7.10 (4H, m).

Example 53

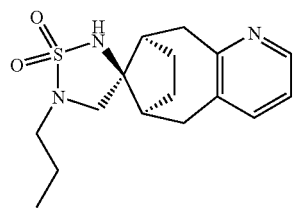

Step 1: (6S/R,9R/S)-5,6,7,8,9,10-hexahydro-6,9-methano-cycloocta[b]pyridin-11-one.

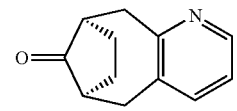

2,3-bis(hydroxymethyl)pyridine hydrochloride (JP 49 020181) (2.7 g, 15.4 mmol) was added portionwise to stirred thionyl chloride (20 mL) at 0° C. under nitrogen. The cooling bath was removed, and the reaction allowed to come to room temperature, then heated at reflux for one hour. The dark mixture was allowed to cool to room temperature, then the thionyl chloride was removed in vacuo. The residue was azeotroped with toluene (x2), the brown solid residue treated with ice, basified with Na$_2$CO$_3$ (sat), then extracted with diethyl ether (x3). The combined extracts were dried (Na$_2$SO$_4$), filtered and evaporated to give 2,3-bis(chloromethyl)pyridine (2.6 g) as a red/brown liquid. This material was used immediately in the next step.

Diethylisopropyl amine (6.6 mL, 38 mmol) and 1-pyrrolidinocyclopentene (2.8 mL, 19.2 mmol) were added to a solution of 2,3-bis(chloromethyl)pyridine in dry acetonitrile (50 mL) at 0° C. The dark mixture was stirred at 0° C. for fifteen minutes, at room temperature for one hour, then at reflux for two hours. The acetonitrile was then removed in vacuo and the residue was taken up in water (40 mL). The solution was adjusted to pH 1 with concentrated hydrochloric acid and then heated at reflux for 24 hours. After cooling to 0° C., the pH was adjusted to >8 with 4N sodium hydroxide. The aqueous layer was extracted with dichloromethane (x4), and the combined extracts dried (Na$_2$SO$_4$), filtered and evaporated. Partial purification of the residue was achieved by chromatography on silica, eluting with 80% ethyl acetate/hexanes followed by 100% ethyl acetate. This gave the title ketone (~700 mg, ~25%) as a dark oil; MS (ES+) 188 ([MH]$^+$).

Step 2

The product from step 1 was converted to the N-propyl cyclic sulfamide using the procedures described in Example 18, step 1 and then Example 20. Final purification by preparative HPLC gave the N-propyl cyclic sulfamide (17 mg) as a solid, δ ($^1$H, 360 MHz, CDCl$_3$) 0.98 (3H, t, J=7.3), 1.21–1.30 (2H, m), 1.61–1.78 (5H, m), 2.49 (2H, br m), 2.62 (1H, dd, J=16.1, 7.3), 2.99–3.30 (6H, m), 4.77 (1H, br s), 7.05–7.09 (1H, m), 7.40 (1H, br d J=7.6), 8.36 (1H, br d J=3.4); MS (ES+) 322 ([MH]$^+$).

Example 54

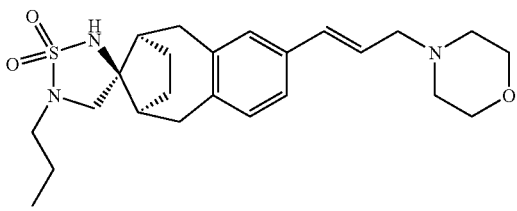

To a solution of ester (160 mg) from example 82 in THF (2 ml) at 0° C. under nitrogen was added 1M DIBAL in toluene (1.2 ml) dropwise. Allowed to warm to room temperature and stirred for 3 hrs, recooled to 0° C., added methanol (few drops) and stirred for 5 mins. Added 1M HCl, allowed to warm to room temperature, extracted with EtOAc (3×) and washed the combined organic extracts with saturated NaHCO$_3$. Dried and concentrated, residue dissolved in DCM (2 ml) and cooled to −20° C. Added 1M PBr$_3$ (0.15 ml) dropwise and allowed to warm to 0° C. and stirred for 20 mins. Added morpholine (0.2 ml) and allowed to warm to room temperature and stirred for 30 mins, before adding saturated NaHCO$_3$ and extracting with DCM (3×). Dried and concentrated and purified by chromatography on silica eluting with EtOAc, then dissolved in Et$_2$O/MeOH, cooled to 0° C. and bubbled in HCl for 5 mins. Concentrated and triturated with Et$_2$O to give the desired compound (HCl salt) as a white powder (78 mg). $^1$H NMR (d$_6$-DMSO 360 MHz) δ$_H$ 0.90 (3H, t, J=7.3), 1.01 (2H, m), 1.55 (2H, m), 1.68 (2H, m), 2.31 (2H, brs), 2.58 (2H, dd, J=7.8, 15.9), 2.89 (2H, t, J=7.1), 3.04–3.21 (6H, m), 3.39 (2H, m), 3.76–3.98 (6H, m), 6.34 (1H, m), 6.75 (1H, d, J=15.8), 7.11 (1H, d, J=7.6), 7.21 (2H, m), 7.70 (1H, s), 11.39 (1H, s).

Example 55

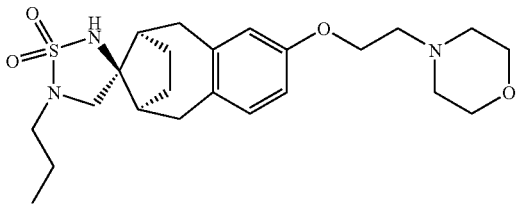

To the phenol from example 44 (100 mg) in DCM (1 ml) at 0° C. were added dropwise PPh$_3$ (117 mg) and 4-(2-hydroxyethyl)morpholine (54 μl) then diethylazodicarboxylate (70 μl). Allowed to warm to room temperature and stirred for 2 hrs. Added water and extracted with DCM (3×), dried and concentrated and purified by column chromatography on silica eluting with 90% EtOAc: hexane then by HPLC. Dissolved in Et$_2$O/MeOH and bubbled in HCl at 0° C., concentrated and triturated with Et$_2$O to give the desired product (HCl salt) as a white powder (35 mg). $^1$H NMR (d$_6$-DMSO 360 MHz) δ$_H$ 0.90 (3H, t, J=7.3), 1.03 (2H, m), 1.55 (2H, m), 1.66 (2H, m), 2.28 (2H, brm), 2.54 (2H, m), 2.88 (2H, t, J=7.1), 3.06–3.20 (6H, m), 3.48 (4H, m), 3.80 (2H, m), 3.96 (2H, m), 4.36 (2H, t, J=4.5), 6.71 (1H, dd, J=2.2, 8.2), 6.75 (1H, brs), 7.03 (1H, d, J=8.2), 7.65 (1H, s),11.04 (1H, brs).

Example 56

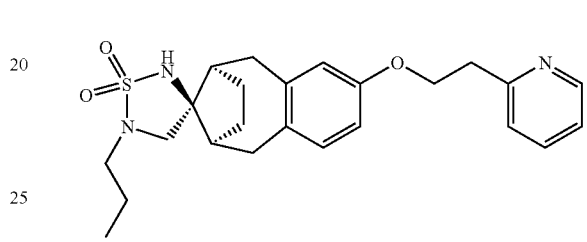

To a solution of the phenol from example 44 (80 mg) in DCM (1 ml) at room temperature was added polymer-supported triphenyl phosphine (Aldrich-179 mg), 2-(2-hydroxyethyl)pyridine) and diethylazodicarboxylate (56 μl) and the mixture stirred o/n. Methanol was added to the reaction and the mixture filtered through a short plug of Celite and purified by HPLC and the HCl salt prepared as in the previous example to give the desired product as a white powder (25 mg).). $^1$H NMR (d$_6$-DMSO 360 MHz) δ$_H$ 0.90 (3H, t, J=7.3), 1.00 (2H, m), 1.52 (2H, m), 1.64 (2H, brm), 2.27 (2H, brm), 2.47 (2H, m), 2.88 (2H, t, J=7.1), 3.06–3.16 (4H, m), 3.41 (2H, t, J=6.2), 4.35 (2H, t, J=6.3), 6.64 (2H, m), 6.97 (1H, d, J=8.1), 7.63 (1H, s), 7.79 (1H, m), 7.91 (1H, d, J=8), 8.36 (1H, m), 8.78 (1H, d, J=6.3).

Example 57

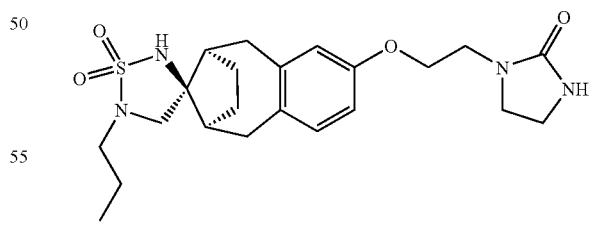

Prepared as in example 56, replacing 2-(2-hydroxyethyl) pyridine) with 1-(2-hydroxyethyl)-2-imidazoline. $^1$H NMR (360 MHz, CDCl$_3$) δ$_H$ 0.98 (3H, t, J=7.3), 1.27 (2H, m), 1.66 (4H, m), 2.38 (2H, brm), 2.59 (2H, m), 3.01 (2H, t, J=7.2), 3.10 (1H, d, J=15.9), 3.20 (3H, m), 3.41 (2H, t, J=8.4), 3.56 (2H, t, J=5.1), 3.64 (2H, m), 4.06 (2H, t, J=5.1), 4.58 (1H, s), 5.04 (1H, s), 6.62 (2H, m), 6.97 (1H, d, J=9).

Example 58

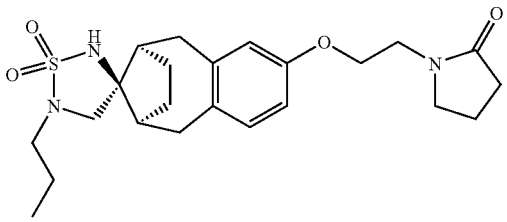

Prepared as in example 56, replacing 2-(2-hydroxyethyl) pyridine) with 1-(2-hydroxyethyl)-2-pyrrolidinone. $^1$H NMR (360 MHz, CDCl$_3$) $\delta_H$ 0.97 (3H, t, J=7.3), 1.27 (3H, m), 1.67 (3H, m), 2.01 (2H, m), 2.39 (2H, brm), 2.59 (2H, m), 3.01 (2H, t, J=7.2), 3.10 (1H, d, J=15.9), 3.20 (3H, m), 3.58 (2H, t, J=8.4), 3.65 (2H, t, J=5.1), 4.06 (2H, t, J=5.1), 4.93 (1H, s), 6.61 (2H, m), 6.97 (1H, d, J=9).

Example 59

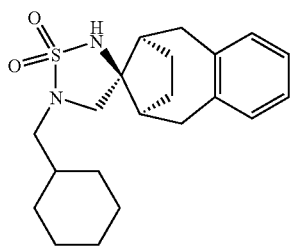

Prepared as in example 21, using cyclohexyl methyl bromide instead of n-butyl iodide. $^1$H NMR (360 MHz, CDCl$_3$) $\delta_H$ 0.96 (2H, m), 1.21 (6H, m), 1.55 (1H, m), 1.65–1.82 (6H, m), 2.41 (2H, m), 2.67 (2H, dd, J=7.7, 16), 2.88 (2H, d, J=7.3), 3.19 (2H, d, J=16.9), 3.21 (2H, s), 4.65 (1H, s), 7.10 (4H, m).

Example 60

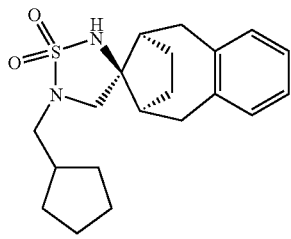

Prepared as in example 21, using cyclopentyl methyl bromide instead of n-butyl iodide. $^1$H NMR (360 MHz, CDCl$_3$) $\delta_H$ 1.26 (4H, m), 1.65–1.82 (6H, m), 1.80 (2H, m), 2.15 (1H, m), 2.41 (2H, m), 2.67 (2H, dd, J=7.7, 16.2), 2.96 (2H, d, J=7.3), 3.18 (2H, d, J=16.3), 3.23 (2H, s), 4.68 (1H, s), 7.09 (4H, m).

Example 61

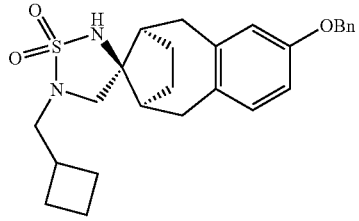

Prepared as in example 27, using cyclobutylmethyl bromide instead of n-propyl bromide. $^1$H NMR (360 MHz, CDCl$_3$) $\delta_H$ 1.25 (2H, m), 1.59–1.96 (6H, m), 2.08 (2H, m), 2.35 (2H, m), 2.56 (3H, m), 3.06–3.20 (6H, m), 4.71 (1H, s), 5.02 (2H, s), 6.71 (2H, m), 6.98 (1H, d, J=7.8), 7.37 (5H, m).

Example 62

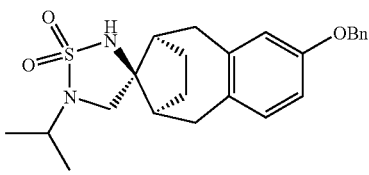

Prepared as in example 27, using 2-iodopropane instead of n-propyl bromide. $^1$H NMR (360 MHz, CDCl$_3$) $\delta_H$ 1.27 (6H, d, J=6.6), 1.30 (2H, m), 1.68 (2H, m), 2.39 (2H, m), 2.59 (2H, m), 3.11 (1H, d, J=15.9), 3.20 (3H, m), 3.70 (1H, m), 4.75 (1H, s), 5.02 (2H, s), 6.71 (2H, m), 6.98 (1H, d, J=7.8), 7.39 (5H, m).

Example 63

[11-endo][6S/R,9R/S,11R/S] 2',3',4',5,5',6,7,8,9,10-decahydro-2-benzyloxy-spiro[6,9-methanobenzocyclooctene-11-3'-{4'4'-spirobut-2"-ene[1',2',5']thiadiazole]}1',1'-dioxide

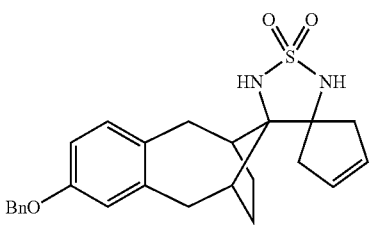

Step 1

To a solution of the nitrile from Example 26 Step 2 (0.41 g, 1.29 mmol), in THF (10 ml) was added chlorotrimethylsilane (0.163 ml, 1.29 mmol). The solution was cooled (−40° C.) and allylmagnesium bromide in diethyl ether (1M, 4 ml 3.1 mmol) was added. The solution was stirred at −40° C. for 15 minutes and then warmed to room temperature for 30 minutes. The solution was partition between ethyl acetate and aqueous potassium carbonate and the organic phase was dried (MgSO$_4$) and evaporated to dryness. The residue was purified by chromatography on silica gel eluting with 100% ethyl acetate to give [11-endo]-11-allyl-11-amino-2-(benzyloxy)-5,6,7,8,9,10-hexahydro-6,9-methanobenzo[a][8]annulene (104 mg) as the first eluting compound followed by elution with 10% methanol and 0.4% aqueous ammonia in ethyl acetate to give [11-endo]-11-[4-aminohepta-1,6-dien-4-yl]-11-amino-2-(benzyloxy)-5,6,7,8,9,10-hexahydro-6,9-methanobenzo[a][8]annulene (117 mg). MS m/z 403(M+H)

Step 2

A solution of second product of Step 1 (117 mg) and sulfamide (120 mg) in pyridine (0.5 ml) was heated at 120° C. for 0.5 h. The solution was evaporated to dryness and the residue was partitioned between ethyl acetate and 0.2M aqueous hydrochloric acid. The organic phase was washed with saturated brine, dried (MgSO$_4$) and evaporated. The residue was dissolved in DCM and purified by chromatography on silica gel (eluting with 10% ethyl acetate in isohexane) to give [11-endo][6S/R,9R/S,11R/S] 2',3',4',5,5', 6,7,8,9,10-decahydro-4',4'-diallyl-2-benzyloxy-spiro[6,9-methanobenzocyclooctene-11-3'-[1,2,5]thiadiazole]1',1'-dioxide $^1$H NMR (400 MHz, CDCl$_3$) δ 1.42(2H, dd J 14.5 Hz and 6.6 Hz), 1.73(2H, m), 2.53–2.60(4H, m), 2.65–2.71(2H, m), 2.77–2.80(2H, m), 3.20(1H, d J 15.9 Hz), 3.35(1H, d J 16.0 Hz), 4.51(1H, s), 4.79(1H, s), 5.02(2H, s), 5.21(4H, m), 5.98–6.10(2H,m), 6.72(2H, m), 6.99(1H, d J 9.0 Hz), 7.30–7.44(5H, m). MS m/z 465(M+H)

Step 3

To a solution of the product of Step 2 (24 mg) in DCM (10 ml) was added bis(tricyclohexylphosphine)benzylidene ruthenium (IV) dichloride (Grubb's catalyst, 4 mg). After stirring the solution at room temperature for 1 h, the solvent was removed in vacuo and the residue purified by chromatography on silica gel (eluting with 10%, followed by 25%, ethyl acetate in isohexane to give the title compound $^1$H NMR (400 MHz, CDCl$_3$) δ 1.40(1H, d J 6.6 Hz), 1.44(1H, d J6.2 Hz), 1.75(2H, m), 2.60(1H, d J 15.6 Hz), 2.66–2.72(5H, m), 2.80(2H, dd J 16.8 Hz and 2.3 Hz), 3.28(1H, d J 14.4 Hz) 3.40(1H, d J 2.3 Hz), 4.85(1H, s), 5.00(2H, s), 5.02(1H, s), 5.75(2H, s), 6.69(2H, m), 6.96(1H, d J 8.8 Hz), 7.29–7.42(5H, m).

Examples 64, 66, 68–73, 75, 78, 79, 97–102, 109, 119–126 and 130–139

The compounds in table 1 were prepared from the corresponding allyl alcohols by the methods of Example 54, using the appropriate amine (4eq.) and Hunig's base (5eq.) instead of morpholine. The allyl alcohols were obtained by the sequential procedures of Examples 27, 44, 51, 80, 81, 82 and 54 (first step), using the appropriate alkyl halide in Example 27.

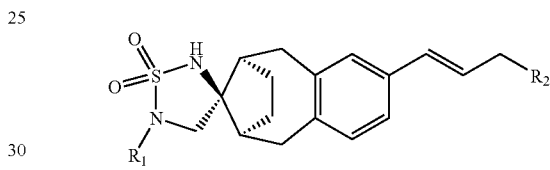

TABLE 1

| Example | R$^1$ | R$^2$ | m/z (M + H$^+$) |
|---|---|---|---|
| 64 | nPr | —N(piperidine)—CF$_3$ | 512 |
| 66 | cyclobutylmethyl | —N(morpholine)—O | 472 |
| 68 | nPr | —N(piperidine)(F)(F) | 480 |
| 69 | nPr | —N(piperidine)—C(O)NH$_2$ | 487 |
| 70 | nPr | —N(piperidine)—C(O)OEt | 516 |
| 71 | nPr | —N(piperidine)—C(O)OH | 488 |

TABLE 1-continued
| Example | R¹ | R² | m/z (M + H⁺) |
|---|---|---|---|
| 72 | nPr | 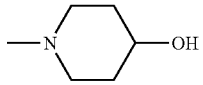 | 460 |
| 73 | 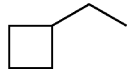 | 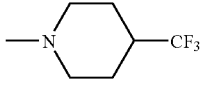 | * |
| 75 | CF₃CH₂ |  |  |
| 78 | nPr | 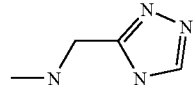 | 483 |
| 79 | nPr | 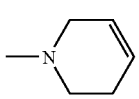 | 442 |
| 97 | nPr | 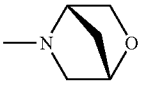 | 458 |
| 98 | nPr | 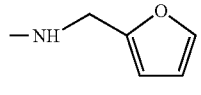 | 456 |
| 99 | nPr | 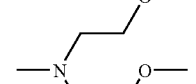 | 492 |
| 100 | nPr | 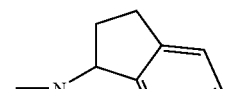 | 492 |
| 101*** | nPr | 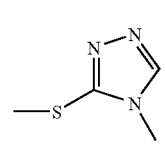 | 474 |
| 102 | nPr | 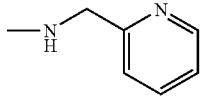 | 467 |
| 109 | CF₃CH₂ | 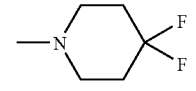 | 520 |
| 119 | CF₃CH₂ | 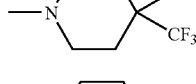 | 568 |
| 120 | CF₃CH₂ | 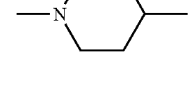 | 498 |

TABLE 1-continued
| Example | R¹ | R² | m/z (M + H⁺) |
|---|---|---|---|
| 121 | CF₃CH₂ | 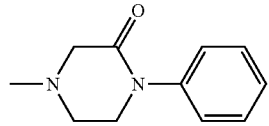 | 498 (MH-Ph) |
| 122 | CF₃CH₂ | 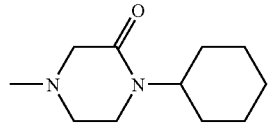 | 498 (MH-cyclohexyl) |
| 123 | CF₃CH₂ | 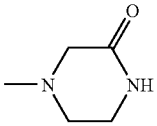 | 498 |
| 124 | CF₃CH₂ | 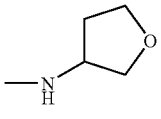 | 486 |
| 125 | CF₃CH₂ | 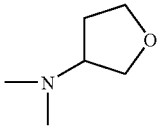 | 500 |
| 126 | CF₃CH₂ | 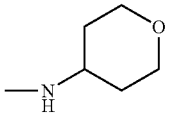 | 500 |
| 130 | CF₃CH₂ | 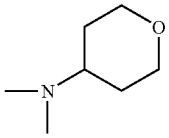 | 514 |
| 131 | CF₃CH₂ | 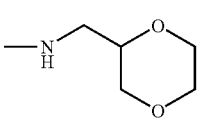 | 516 |
| 132 | CF₃CH₂ | 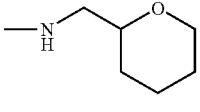 | 514 |
| 133 | CF₃CH₂ | 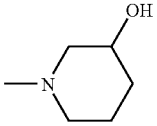 | 500 |
| 134 | CF₃CH₂ | 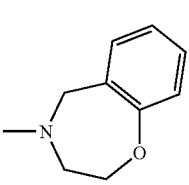 | 548 |

TABLE 1-continued

| Example | R¹ | R² | m/z (M + H⁺) |
|---|---|---|---|
| 135 | CF₃CH₂ | 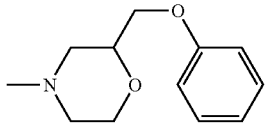 | 592 |
| 136 | CF₃CH₂ | 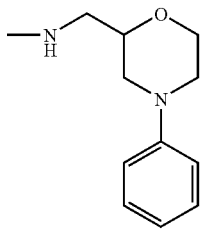 | 591 |
| 137 | CF₃CH₂ | 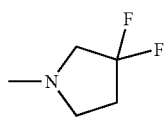 | 506 |
| 138 | CF₃CH₂ | 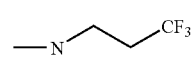 | 512 |
| 139 | CF₃CH₂ | 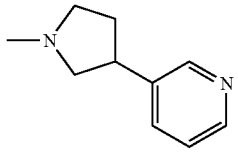 | 547 |

*NMR data for Example 73 - ¹H NMR(360MHz, d₆-DMSO) δ_H 1.10(2H, m), 1.67–2.09(12H, m), 2.31(2H, brs), 2.57(4H, m), 2.98(4H, m), 3.21(4H, m), 3.52(2H, brm), 3.90(2H, brm), 6.30 (1H, dt, J=7.5, 15.7), 6.77(1H, d, J=15.9), 7.09(1H, d, J=7.6), 7.19(2H, m), 7.44(1H, s), 10.75 (1H, s).

**Allyl alcohol precursor - Example 89. NMR data for Example 75 - ¹H NMR(360MHz, d₆-DMSO) δ_H 1.03(2H, m), 1.69(2H, m), 1.86(2H, brm), 2.04(2H, brm), 2.37(2H, brs), 2.60(3H, m), 2.97(2H, brm), 3.18(2H, m), 3.46(2H, s), 3.54(2H, d, J=12), 3.84(2H, m), 4.02(2H, q, J=8.7), 6.32(1H, dt, J=5.6, 15.9), 6.77(1H, d, J=15.6), 7.12(1H, d, J=7.6), 7.22(2H, m), 8.02(1H, s), 10.67(1H, s).

***using 3-mercapto-4-methyl-1,2,4-triazole instead of an amine.

Example 65

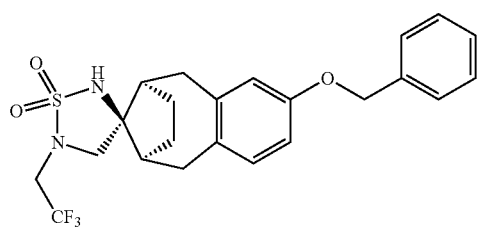

To the diamine from Example 26, Step 3a (20 g) in THF (1200 ml) cooled to −70° C. under nitrogen was added dropwise (over 15 mins) a solution of trifluoroacetic anhydride (9.2 ml) in THF (70 ml). The reaction was allowed to warm to room temperature overnight, then concentrated to give a pale yellow foam which was dissolved in THF (250 ml), cooled to 0° C. under nitrogen and treated dropwise with 1M borane in THF (180 ml). After 10 mins the reaction was allowed to warm to room temperature, stirred for 30 mins, before heating to reflux for 2 hrs. The reaction was recooled to 0° C. and 5M HCl (50 ml) was added dropwise, stirred for 15 mins, then basified with 4M NaOH. The mixture was extracted with EtOAc (3×), washed with water and brine, dried and evaporated. Column chromatography on silica eluting with 2–4–8% MeOH:DCM gave a pale yellow oil (16 g). This was dissolved in pyridine (200 ml) and sulfamide (16 g) was added and the reaction heated to reflux for 6 hrs. The reaction mixture was concentrated and then DCM and 1M HCl were added and the mixture stirred vigorously for 30 mins. The layers were separated and the aqueous layer re-extracted with DCM (4×). The DCM layers were dried, concentrated and azeotroped with toluene. Column chromatography on silica, eluting with 90% DCM: hexane then DCM, gave the desired product as a white foam (11.5 g). ¹H NMR (360 MHz, CDCl₃) δ_H 1.34 (2H, m), 1.70 (2H, m), 2.41 (2H, m), 2.62 (2H, m), 3.11 (2H, d, J=15.9), 3.20 (1H, d, J=15.9), 3.42 (2H, ABq, J=9.3, 13.3), 3.67 (2H, dq, J=2.2, 8.7), 4.76 (1H, s), 5.02 (2H, s), 6.72 (2H, m), 6.99 (1H, d, J=7.8), 7.37 (5H, m).

Example 67

[11-endo]2-benzyloxy-2',3',4',5,5',6,7,8,9,10-decahydro-5'-propylspiro[6,9-methanobenzocyclooctene-11-3'-[1,2,5]thiadiazole]1',1'-dioxide

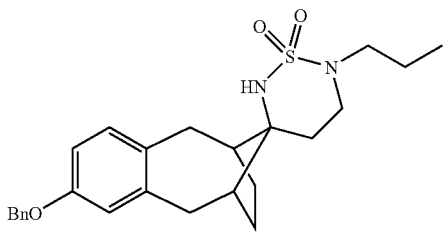

Step 1

To a solution of the nitrile from Example 26 Step2 (0.384 g, 1.21 mmol) in THF (10 ml) was added allylmagnesium bromide (1M, in diethyl ether, 2.4 ml). The solution was quenched by addition of saturated ammonium chloride and the product extracted into ethyl acetate. After drying (MgSO$_4$) and removal of the solvent in vacuo the residue was purified by chromatography on silica gel (eluting with 30% ethyl acetate in isohexane) to give the [11-endo]-11-allyl-11-amino-2-(benzyloxy)-5,6,7,8,9,10-hexahydro-6,9-methanobenzo[a][8]annulene.

$^1$H NMR (400 MHz, CDCl$_3$) δ 1.24(2H, m), 1.77(2H, m), 2.00(2H,m), 2.22(2H, d J 7.5 Hz), 2.55(2H, m), 3.18(1H, d J 16.2 Hz), 3.23(1H, d J 16.2 Hz), 5.01(2H, s), 5.14(2H, m), 5.92(1H, m), 6.69(1H, dd J 8.2 Hz and 2.6 Hz), 6.74(1H, d J 2.4 Hz), 6.99(1H, d J 8.2 Hz), 7.28–7.43(5H, m). The hydrochloride salt was formed by addition of ethereal HCl and evaporation to an oil.

Step 2

A solution of the hydrochloride salt from Step 1 (228 mg, 0.62 mmol) in a mixture of methanol: DCM (1:1) at –80° C. was ozonolysed until a persistent blue colour formed. After purging the solution with oxygen and nitrogen, dimethyl sulphide (0.5 ml) was added and the solution warmed to room temperature for 2 h. To the residue was added propylamine (0.2 ml) and DCM (10 ml) and after 15 minutes sodium triacetoxyborohydride (0.51 g) was added. After stirring the solution for 2 h at room temperature the solvent was removed by evaporation and the residue was partitioned between ethyl acetate and aqueous K$_2$CO$_3$. The organic phase was dried, evaporated, and the residue purified by chromatography on silica gel (eluting with increasing concentrations 10%, 20%, 30% of a mixture of methanol: aqueous ammonia:DCM (10:0.4:90) in DCM) to give [11-endo]11-(2-(propylamino)ethyl)-11-amino-2-(benzyloxy)-5,6,7,8,9,10-hexahydro 6,9-methanobenzo[a][8]annulene.

Step 3

The product from Step 2 (36 mg) and sulfamide (42 mg) were heated in pyridine (0.5 ml) at 120° C. for 8 h. The solution was evaporated in vacuo to remove the solvent and the residue dissolved in DCM was chromatographed on silica gel (eluting with increasing concentrations of ethyl acetate in isohexane, 0, 10%, 20%). The product was evaporated and the residue crystallized from diethyl ether to give the title product.

$^1$H NMR (400 MHz, CDCl$_3$) δ 0.95(3H, t J 7.4 Hz), 1.27(2H,d J 8.8 Hz), 1.62(2H,q J 7.4 Hz), 1.68(2H, m), 1.75(2H, t J 5.9 Hz), 2.41(1H, m), 2.45–2.52(3H,m), 3.04 (2H, td J 7.0 Hz and 2.8 Hz), 3.33(2H, m), 3.38(1H, d J 15.8 Hz), 3.47(1H, dm J 15.1 Hz), 4.1(1H, s), 5.02(2H, s), 6.68(1H, dd J 8.4 Hz and 2.6 Hz), 6.7(1H, d J 2.1 Hz), 6.96(1H, d J 8.1 Hz), 7.31–7.44(5H, m). MS nm/z 441 (M+H).

Example 74

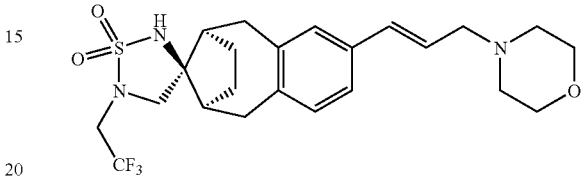

Prepared from the allyl alcohol from Example 89 by the method of Example 54. $^1$H NMR (360 MHz, d$_6$-DMSO) δ$_H$ 1.34 (2H, m), 1.68 (4H, m), 1.84–2.04 (5H, brm), 2.44 (2H, m), 2.66 (2H, m), 3.04–3.23 (6H, m), 3.43 (2H, s), 3.68 (2H, q, J=8.7), 4.77 (1H, brs), 6.22 (1H, dt, J=5.6, 15.9), 6.45 (1H, d, J=15.8), 7.02–7.15 (3H, m).

Example 76

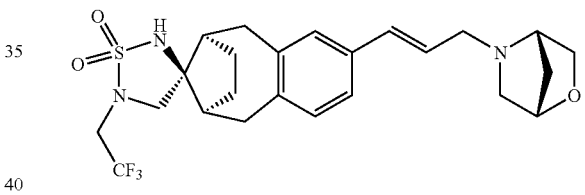

Prepared from the allyl alcohol from Example 89 by the method of Example 54, substituting 2-aza-5-oxabicyclo [2.2.1]heptane for morpholine, and isolated as a mixture of diastereoisomers. MS(ES+) 498, MH$^+$.

Example 77

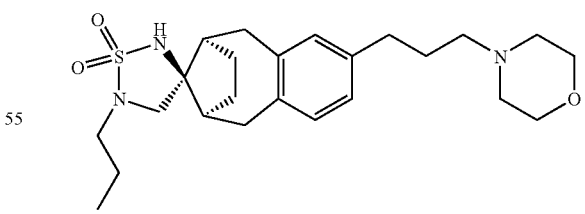

The HCl salt (250 mg) from Example 54 was dissolved in EtOH, Pearlman's catalyst (50 mg) added and the mixture hydrogenolysed for 4 hrs at 50 psi. The mixture was filtered, concentrated and triturated with ether to give the desired product as a white powder (210 mg). $^1$H NMR (360 MHz, d$_6$-DMSO) δ$_H$ 0.90 (3H, t, J=7.3), 1.02 (2H, m), 1.55 (2H, q, J=12.8), 1.66 (2H, m), 1.99 (2H, brm), 2.30 (2H, brm), 2.55 (4H, m), 3.03–3.19 (8H, m), 3.04–3.21 (6H, m), 3.39 (3H, m), 3.80–3.90 (3H, m), 6.93–7.03 (3H, m), 7.65 (1H, s), 11.09 (1H, s).

Example 80

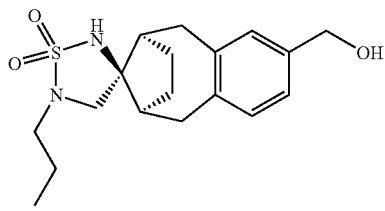

To a solution of ester (2.4 g) from Example 51 in THF (40 ml) at 0° C. under nitrogen was added dropwise 1M DIBAL in toluene (25 ml). The reaction was allowed to warm to room temperature and stirred for 3 hrs, before methanol (several drops) was added followed by 1M HCl (10 ml). The mixture was stirred for 20 mins then extracted with EtOAc (3×), and the combined extracts washed with saturated sodium bicarbonate, dried and evaporated. Trituration with ether gave the desired product as a white powder (2.1 g). $^1$H NMR (360 MHz, CDCl$_3$) $\delta_H$ 0.98 (3H, t, J=6.6), 1.26 (2H, m), 1.67 (4H, m), 2.41 (2H, brs), 2.68 (2H, dd, J=6.9, 14.5), 3.01 (2H, t, J=6.2), 3.15 (2H, dd, J=7.9, 14.4), 3.21 (2H, s), 4.65 (3H, m), 7.10 (3H, m).

Example 81

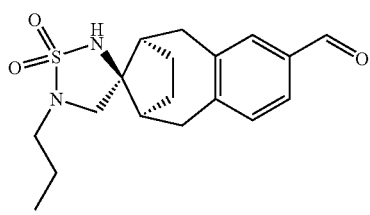

To a solution of benzyl alcohol (2.08 g) from Example 80 in DCM (50 ml) was added in one portion PDC (3.3 g) and the reaction stirred o/n at room temperature. Filtration through a pad of silica, eluting with DCM then EtOAc, followed by evaporation gave the desired product as a white foam (1.84 g). $^1$H NMR (360 MHz, CDCl$_3$) $\delta_H$ 0.98 (3H, t, J=6.6), 1.24 (2H, m), 1.65 (2H, m), 1.73 (2H, m), 2.48 (2H, brs), 2.80 (2H, m), 3.03 (2H, t, J=6.2), 3.24 (4H, m), 4.89 (1H, s), 7.27 (1H, m), 7.62 (2H, m), 9.96 (1H, s).

Example 82

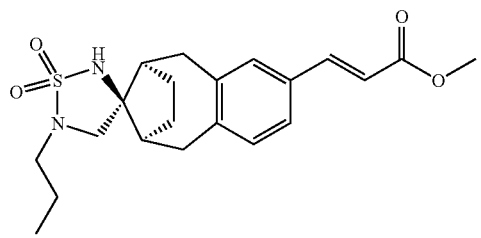

To a solution of aldehyde (3.4 g) from Example 81 and methyl diethylphosphonoacetate (5.4 ml) in THF (40 ml) at room temperature was added LiOH (0.7 g) in one portion and the mixture stirred o/n. Added 1M HCl and extracted with EtOAc (3×), then washed the combined organic extracts with water and brine, dried and concentrated. The crude product was purified by chromatography on silica eluting with 1–2% EtOAc/DCM to give the desired product as a white foam (3.25 g). $^1$H NMR (360 MHz, CDCl$_3$) $\delta_H$ 0.98 (3H, t, J=6.6), 1.27 (2H, m), 1.66 (4H, m), 2.44 (2H, brm), 2.70 (2H, m), 3.02 (2H, t, J=6.4), 3.20 (2H, d, J=15.6), 3.21 (2H, s), 3.80 (3H, s), 4.70 (1H, s), 6.40 (1H, d, J=16), 7.11 (1H, d, J=7.7), 7.26 (2H, m), 7.63 (1H, d, J=16).

Example 83

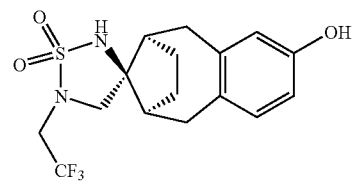

The benzyl ether from Example 65 was deprotected by the procedure of Example 44 to give the desired product. $^1$H NMR (360 MHz, d$_6$-DMSO) $\delta_H$ 1.06 (2H, m), 1.65 (2H, m), 2.29 (2H, m), 2.42 (2H, m), 3.04 (1H, d, J=15.6), 3.11 (1H, d, J=15.6), 3.43 (2H, s), 3.99 (2H, brq, J=9.6), 6.47 (2H, m), 6.85 (1H, d, J=8), 7.93 (1H, s), 9.02 (1H, s).

Example 84

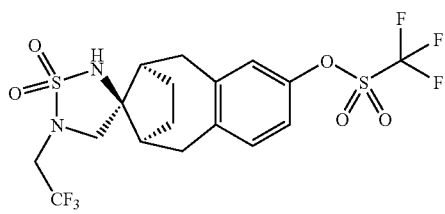

Prepared from the phenol from Example 83 by the procedure of Example 51, Step 1. $^1$H NMR (360 MHz, d$_6$-DMSO) $\delta_H$ 0.99 (2H, m), 1.71 (2H, m), 2.38 (2H, brm), 2.69 (2H, m), 3.16 (1H, d, J=15.7), 3.18 (1H, d, J=15.7), 3.46 (2H, s), 4.02 (2H, brq, J=9.6), 7.18–7.31 (3H, m), 8.04 (1H, s).

Example 85

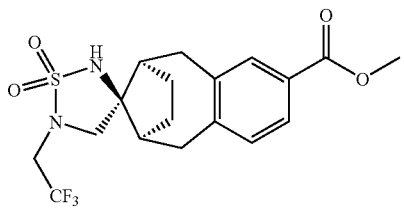

Prepared from the triflate from Example 84 by the procedure of Example 51, Step 2. $^1$H NMR (360 MHz, CDCl$_3$) $\delta_H$ 1.28 (2H, m), 1.72 (2H, m), 2.48 (2H, brm), 2.78 (2H, m), 3.23

(1H, d, J=15.4), 3.27 (1H, d, J=15.4), 3.43 (2H, ABq, J=9.5, 11.1), 3.68 (2H, q, J=8.7), 3.90 (3H, s), 4.79 (1H, s), 7.17 (1H, d, J=8.3), 7.78 (2H, m).

Example 86

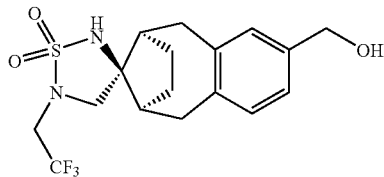

Prepared from the ester from Example 85 by the procedure of Example 80. $^1$H NMR (360 MHz, CDCl$_3$) $\delta_H$ 1.35 (2H, m), 1.71 (2H, m), 2.43 (2H, brm), 2.68 (1H, d, J=16.1), 2.70 (1H, d, J=16.1), 3.17 (1H, d, J=15.9), 3.20 (1H, d, J=15.9), 3.43 (2H, s), 3.69 (2H, q, J=8.7), 4.65 (2H, brs), 4.73 (1H, s), 7.10 (3H, m).

Example 87

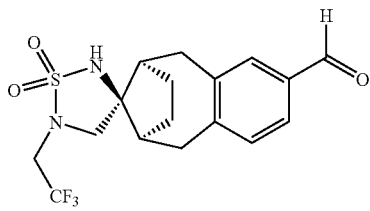

Prepared from the benzyl alcohol from Example 86 by the procedure of Example 81. $^1$H NMR (360 MHz, CDCl$_3$) $\delta_H$ 1.27 (2H, m), 1.74 (2H, m), 2.50 (2H, brm), 2.82 (2H, m), 3.26 (1H, d, J=13.9), 3.30 (1H, d, J=13.9), 3.45 (2H, Abq, J=9.4, 11.5), 3.69 (2H, q, J=8.7), 4.79 (2H, s), 7.28 (1H, d, J=7.6), 7.64 (2H, m), 9.96 (1H, s).

Example 88

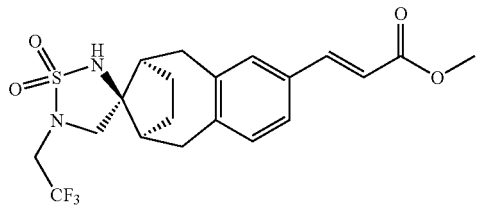

Prepared from the aldehyde from Example 87 by the procedure of Example 82. $^1$H NMR (360 MHz, CDCl$_3$) $\delta_H$ 1.30 (2H, m), 1.73 (2H, m), 2.46 (2H, brm), 2.72 (2H, m), 3.23 (2H, d, J=15.9), 3.44 (2H, s), 3.68 (2H, q, J=8.7), 3.80 (3H, s), 4.65 (2H, brs), 4.80 (1H, s), 6.40 (1H, d, J=16), 7.11 (1H, d, J=7.7), 7.27 (2H, m), 7.66 (1H, d, J=16).

Example 89

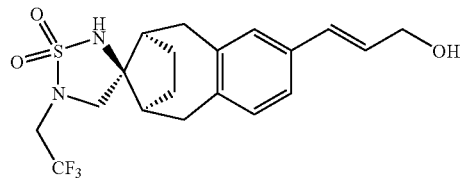

Prepared from the ester from Example 88 by the procedure of Example 54, Step 1. $^1$H NMR (360 MHz, CDCl$_3$) $\delta_H$ 1.31 (2H, m), 1.70 (2H, m), 2.44 (2H, brm), 2.65 (1H, dd, J=2.9, 7.7), 2.70 (1H, dd, J=2.8, 7.7), 3.17 (1H, d, J=7.1), 3.20 (1H, d, J=7.1), 3.43 (2H, s), 3.68 (2H, q, J=8.7), 4.31 (2H, d, J=5.1), 4.78 (1H, s), 6.34 (1H, dt, J=5.7, 15.9), 6.56 (1H, d, J=15.8), 7.04 (1H, d, J=7.7), 7.11 (1H, s), 7.16 (1H, m).

Example 90

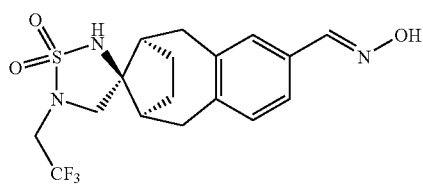

To a solution of aldehyde (60 mg) from Example 87 in EtOH (2 ml) was added hydroxylamine hydrochloride (32 mg) and sodium acetate (38 mg) and the mixture heated to reflux for 2 hrs. The mixture was evaporated to dryness, water added and then extracted with DCM (3×). Dried and concentrated, then trituration with ether/hexane gave the desired product as a white powder (32 mg). $^1$H NMR (360 MHz, d$_6$-DMSO) $\delta_H$ 1.08 (2H, brm), 1.69 (2H, brm), 2.38 (2H, brm), 2.59 (2H, brm), 3.20 (2H, brm), 3.44 (2H, brm), 3.94 (2H, brm), 7.11 (1H, d, J=6.3), 7.30 (2H, m), 7.80 (1H, s), 8.03 (1H, s), 10.85 (1H, s).

Example 91

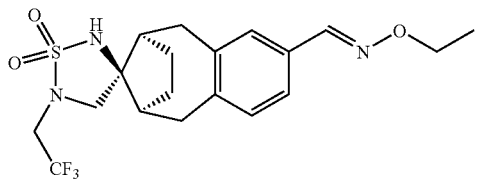

Prepared as in Example 90, using O-ethylhydroxylamine hydrochloride instead of hydroxylamine hydrochloride. $^1$H NMR (360 MHz, CDCl$_3$) $\delta_H$ 1.33 (5H, m), 1.71 (2H, m), 2.45 (2H, brm), 2.72 (2H, m), 3.21 (1H, d, J=16), 3.22 (1H, d, J=16), 3.43 (2H, s), 3.68 (2H, q, J=8.7), 4.21 (2H, q, J=7.1), 4.90 (1H, brs), 7.09 (1H, d, J=6.3), 7.30 (2H, m), 8.02 (1H, s).

Examples 92–95

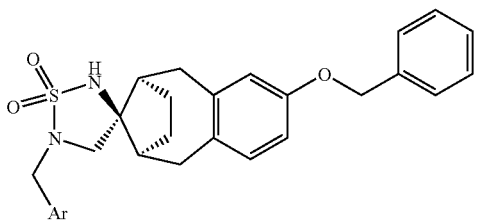

The compounds of table 3 below were prepared by the following procedure. Sodium hydride (60% dispersion in oil, 12 mg, 0.3 mmol) was added in one portion to a stirred solution of the unsubstituted cyclic sulfamide from Example 26 (100 mg, 0.26 mmol) in dry THF (2 mL) at room temperature. After 90 minutes at room temperature, the relevant benzyl bromide (0.3 mmol) was added, and stirring at room temperature continued overnight. The reaction was quenched with water, partitioned between ethyl acetate and water, and the aqueous layer extracted with ethyl acetate (x2). The combined extracts were dried ($Na_2SO_4$), filtered and evaporated. The residue was purified by chromatography on silica, eluting with 10→20→30% ethyl acetate/hexanes, to give the N-benzylated cyclic sulfamides indicated in the table.

TABLE 3

| Example | Ar | MS (ES+) [MH]+ |
|---|---|---|
| 92 | phenyl | 475 |
| 93 | 3,4-difluorophenyl | 511 |
| 94 | 4-chlorophenyl | * |
| 95 | 2,5-difluorophenyl | 511 |

*NMR data for Ex. 94 - δ ($^1$H, 400 MHz, $CDCl_3$) 1.16–1.28 (2 H, m), 1.52–1.57 (2 H, m), 2.31–2.37 (2 H, m), 2.56–2.64 (2 H, m), 3.04–3.20 (4 H, m), 4.18 (2 H, br s), 4.81 (1 H, br s), 5.01 (2 H, br s), 6.70–6.73 (2 H, m), 6.97 (1 H, d J = 7.8), 7.30–7.42 (9 H, m).

Example 96

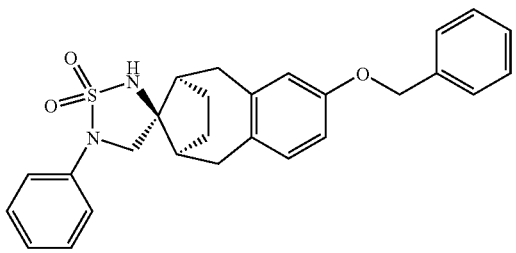

A solution/suspension the unsubstituted cyclic sulfamide from Example 26 (500 mg, 1.3 mmol), benzene boronic acid (320 mg, 2.6 mmol), copper (II) acetate (355 mg, 2.0 mmol) and phosphazene base $P_4$-t-Bu (1.0M in hexane, 2.6 mL, 2.6 mmol) and 4A sieves (1 g) in dry DCM was stirred at room temperature under air for three days. The reaction was quenched with methanolic ammonia (2M, 5 mL), then filtered through Hyflo™, washing with dichloromethane. The filtrate was evaporated and the residue was purified by chromatography on silica, eluting with 24% ethyl acetate/dichloromethane to give the N-phenyl cyclic sulfamide (86 mg, 14%) as a solid, δ ($^1$H, 360 MHz, $d_6$-DMSO) 1.10–1.2 (2H, m), 1.77–1.80 (2H, m), 2.45–2.60 (4H, m), 3.14–3.24 (2H, m), 3.74 (2H, br s), 5.05 (2H, br s), 6.72–6.81 (2H, m), 7.01–7.09 (2H, m), 7.19–7.21 (2H, m), 7.32–7.45 (7H, m), 8.29 (1H, br s); MS (ES+) 461 ([MH]$^+$).

Example 103

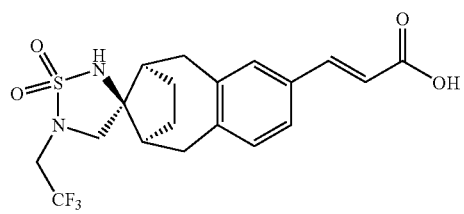

To a solution of ester (80 mg) from Example 88 in THF (2 ml) and water (1 ml) was added NaOH (22 mg) then the reaction was heated to reflux for 2 hrs. Added 1M HCl, extracted with DCM (3×), dried and concentrated. Trituration with ether afforded the desired product as a white powder (41 mg). $^1$H NMR (360 MHz, $d_6$-DMSO) δ$_H$ 1.01 (2H, m), 1.70 (2H, m), 2.36 (2H, brm), 2.62 (2H, m), 3.17 (2H, d, J=15.7), 3.46 (2H, s), 4.02 (2H, q, J=9.5), 6.46 (1H, d, J=15.9), 7.15 (1H, d, J=7.7), 7.39 (1H, d, J=7.8), 7.43 (1H, s), 7.51 (1H, d, J=15.9), 8.02 (1H, s), 12.26 (1H, s).

Example 104

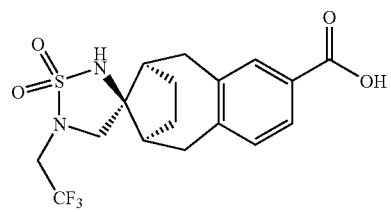

To the ester (50 mg) from Example 85 in THF (2 ml) and water (1 ml) was added NaOH (14 mg) and the reaction heated to reflux for 2 hrs. Added 1M HCl and extracted with DCM (3×). Dried and concentrated then triturated with hexane to give the desired product as a white powder (24 mg). $^1$H NMR (360 MHz, $d_6$-DMSO) δ$_H$ 1.01 (2H, m), 1.70 (2H, m), 2.36 (2H, brm), 2.68 (2H, brm), 3.20 (2H, d, J=15.7), 3.47 (2H, s), 4.02 (2H, q, J=9.6), 7.23 (1H, d, J=7.2), 7.69 (2H, m), 8.04 (1H, s), 12.74 (1H, s).

Example 105

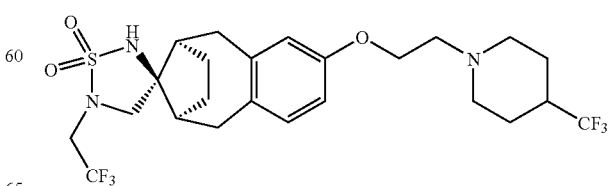

Step 1:

TFA (1 ml) was added to a solution of the MOM-protected 2-bromoethoxy derivative from Example 43 Step 3 (1.324 g) in DCM (40 ml). The reaction was stirred for 3 hr at room temperature, concentrated, and the residue partitioned between DCM and saturated sodium bicarbonate solution. The aqueous layer was extracted with DCM (x2) and the combined organic extracts washed with brine, dried (MgSO$_4$), filtered and evaporated. The residue was purified by chromatography on silica gel eluting with 10–20% EtOAc/hexane to give the deprotected sulfamide (0.957 g, 79%). $^1$H NMR (360 MHz, CDCl$_3$) $\delta_H$ 1.33 (2H, m), 1.70 (2H, m), 2.43 (2H, m), 2.63 (2H, dt, J=15.8, 7.9), 3.16 (2H, dd, J=15.9, 32.9), 3.43 (2H, m), 3.63 (2H, t, J=6.3), 3.67 (2H, dq, J=2.4, 8.7), 4.26 (2H, t, J=6.3), 4.67 (1H, s), 6.66 (2H, m), 6.99 (1H, d, J=7.8).

Step 2:

A solution of the bromide from step 1 (50 mg), Hunig's base (40 mg) and 4-trifluoromethylpiperidine (32 mg) in acetonitrile (1 ml) was heated in a microwave reactor at 180° C. for 10 min. The mixture was concentrated, and the product purified by chromatography on silica gel eluting with 30–40% EtOAc/hexane, then converted to the hydrochloride salt. (32 mg, 52%). $^1$H NMR (360 MHz, MeOH) $^\delta$H 1.20 (2H, m), 1.73 (2H, m), 1.92 (2H, m), 2.20 (2H, m), 2.42 (2H, m), 2.61 (3H, m), 3.14–3.51 (6H, m), 3.59 (2H, m), 3.78 (2H, m), 3.85 (2H, q, J=9.2), 4.34 (2H, t, J=4.8), 6.76 (2H, m), 7.04 (1H, d, J=8.1). MS(ES+) 556, MH$^+$.

Example 106

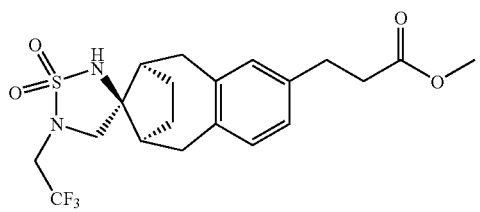

A mixture of the alkene (300 mg) from Example 88 and 10% palladium on carbon (50 mg) in EtOH (20 ml) was hydrogenolysed for 2.5 hrs. Filtered, concentrated and passed through a short plug of silica eluting with 20% EtOAc:hexane to give the desired product as a gummy solid (270 mg). $^1$H NMR (360 MHz, CDCl$_3$) $\delta_H$ 1.29 (2H, m), 1.70 (2H, m), 2.43 (2H, brm), 2.58–2.69 (4H, m), 2.88 (2H, t, J=7.6), 3.15 (1H, d, J=15.4), 3.19 (1H, d, J=15.4), 3.43 (1H, s), 3.68 (5H, m), 4.83 (1H, s), 6.91–7.01 (3H, m).

Example 107

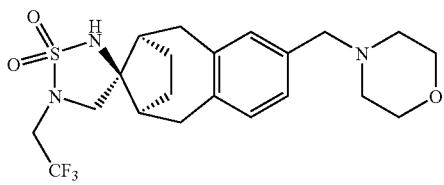

To a solution of the benzyl alcohol (70 mg) from Example 86 in DCM (2 ml) cooled to −20° C. was added dropwise 1M PBr$_3$ in DCM (90 μl). Allowed to warm to 0° C. and stirred for 1 hr, added morpholine (0.5 ml) and then allowed to warm to room temperature with stirring for 2 hrs. Added saturated aqueous NaHCO$_3$ and extracted with DCM (3×), dried and concentrated. Column chromatography on silica eluting with 80% EtOAc:hexane, then HCl salt formation as in Example 54 gave the desired product as a white powder (32 mg). $^1$H NMR (360 MHz, d$_6$-DMSO) $\delta_H$ 1.03 (2H, m), 1.70 (2H, m), 2.38 (2H, brm), 2.58 (2H, m), 3.04 (2H, m), 3.20 (4H, m), 3.47 (2H, s), 3.75 (2H, brm), 3.92 (2H, d, J=12.2), 4.02 (2H, q, J=9.2), 4.24 (2H, d, J=4.9), 7.19 (1H, d, J=8), 7.30 (2H, m), 8.02 (1H, s), 10.80 (1H, s).

Example 108

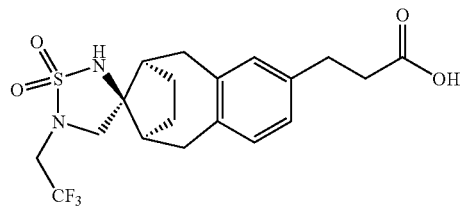

A mixture of the cinnamic acid (300 mg) from Example 103 and 10% palladium on carbon (30 mg) in EtOH (20 ml) was hydrogenolysed for 2 hrs. Filtered and concentrated to give the desired product as a white foam (185 mg). $^1$H NMR (360 MHz, d$_6$-DMSO) $\delta_H$ 1.04 (2H, m), 1.66 (2H, m), 2.33 (2H, brm), 2.51 (4H, brm), 2.74 (2H, m), 3.11 (1H, d, J=14.4), 3.15 (1H, d, J=14.4), 3.44 (2H, s), 4.00 (2H, q, J=9.0), 6.96 (3H, m), 7.76 (1H, s), 11.77 (1H, brs).

Examples 110–116

The compounds in table 2 were prepared by the procedure of Example 105, using the appropriate amines instead of 4-trifluoromethylpiperidine, and were purified by mass directed preparative HPLC.

TABLE 2

| Example | R$^2$ | m/z (M + H$^+$) |
|---|---|---|
| 110 | —N(piperazine)N—C(O)CH$_3$ | 531 |
| 111 | —NH-CH$_2$CH$_2$-O— | 478 |
| 112 | —NH-CH$_2$-(2-thienyl) | 516 |
| 113 | —N-(imidazolyl) | 471 |

TABLE 2-continued

| Example | R² | m/z (M + H⁺) |
|---|---|---|
| 114 | —NH—CH₂-(3-pyridyl) | 511 |
| 115 | —NH—CH₂—C(O)—O—CH₃ | 492 |
| 116 | —N(methyl)-piperazinone-N'-phenyl | 579 |

Example 117

N-cyclobutyl-N'-((1R/S,10S/R,13R/S)-5-{3-[4-(trifluoromethyl)-1-piperidinyl]propyl}tricyclo[8.2.1.0³,⁸]trideca-3,5,7-trien-13-yl)sulfamide

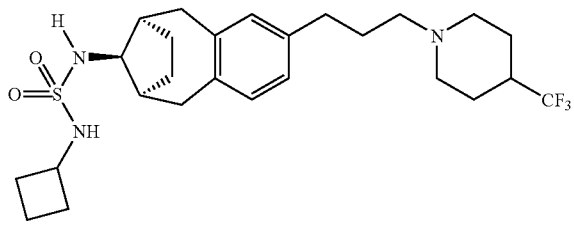

Step 1 3-(13-tert-Butoxycarbonylamino-tricyclo-[8.2.1.0³,⁸]trideca-3(8),4,6-trien-5-yl)-propionic acid methyl ester 3-(13-tert-Butoxycarbonylamino-tricyclo[8.2.1.0³,⁸]trideca-3(8),4,6-trien-5-yl)-acrylic acid methyl ester (300 mg, 0.809 mmol, prepared in Example 32 Step 3) and 20% palladium hydroxide on carbon (30 mg) in ethanol (30 ml) were stirred under 1 atm. of hydrogen at room temperature for 18 hours. The mixture was filtered through Celite and the filtrate concentrated to give a colourless oil 285 mg (94%). ¹H NMR (CDCl₃, 400 MHz) δ 7.00 (1H, d, J=8.2 Hz), 6.90 (2H, m), 4.97 (1H, m), 4.03 (1H, m), 3.67 (3H, s), 2.99 (2H, m), 2.89 (2H, m), 2.55–2.62 (4H, m), 2.48 (2H, m), 1.71 (2H, m), 1.47 (9H, s), 1.19 (2H, m).

Step 2 [5-(3-Oxo-propyl)-tricyclo[8.2.1.0³,⁸]trideca-3(8),4,6-trien-13-yl]-carbamic acid tert-butyl ester DIBAL-H (1M in toluene, 855 μl, 0.855 mmol) was added dropwise to a stirred solution of the product of Step 1 (290 mg, 0.777 mmol) in toluene (8 ml) maintaining the reaction temperature below −70° C. After stirring at −78° C. for 2 hours, more DIBAL-H (77 μl) was added and stirring was continued for 2 additional hours at −78° C. The mixture was quenched with methanol at −78° C., allowed to warm to room temperature and dispersed between ethyl acetate and 1N HCl. The organic phase was washed with sodium bicarbonate solution (sat), brine, dried and concentrated to give a colourless oil. Analysis by NMR showed ~15% starting ester present, so the product was subjected to a further treatment with DIBAL-H (122 μl) for 2 hours at −78° C. as described above. The crude product was purified by column chromatography on silica gel eluting with 5:1 isohexane-ethyl acetate to give a colourless oil 149 mg (56%).¹ NMR (CDCl₃, 360 MHz) δ 9.81 (1H, s), 7.00 (1H, m), 6.90 (2H, m), 4.97 (1H, m), 4.04 (1H, m), 2.86–3.03 (4H, m), 2.75 (2H, m), 2.45–2.63 (4H, m), 1.71 (2H, m), 1.47 (9H, s), 1.19 (2H, m).

Step 3 {5-[3-(4-Trifluoromethyl-piperidin-1-yl)-propyl]-tricyclo [8.2.1.0³,⁸]trideca-3(8),4,6-trien-13-yl}-carbamic acid tert-butyl ester The product from Step 2 (140 mg, 0.408 mmol), 4-trifluoromethylpiperidine hydrochloride (78 mg, 0.408 mmol) and sodium cyanoborohydride (77 mg, 1.22 mmol) in methanol (15 ml) were stirred at room temperature for 18 hours. The mixture was quenched with water and then with sodium bicarbonate solution (sat). The product was extracted with DCM and the organic phase was dried and concentrated. The crude product was purified by column chromatography on silica gel eluting with 40:1 DCM-2M NH₃ in MeOH to give a colourless oil. The product was re-purified by column chromatography on silica gel eluting with 7:1 isohexane-ethyl acetate to give a colourless oil 87 mg (44%). ¹H NMR (CDCl₃, 400 MHz) δ 6.99 (1H, d, J=8.0 Hz), 6.89 (2H, m), 4.98 (1H, m), 4.02 (1H, m), 2.95–3.02 (4H, m), 2.45–2.62 (6H, m), 2.35 (2H, m), 1.58–2.04 (11H, m), 1.47 (9H, m), 1.19 (2H, m). m/z 481 (M+H⁺).

Step 4 5-[3-(4-Trifluoromethyl-piperidin-1-yl)-propyl]-tricyclo[8.2.1.0³,⁸]trideca-3(8),4,6-trien-13-ylamine The Boc protecting group was removed by dissolving the product of Step 3 (87 mg, 0.181 mmol) in 3:1 DCM-TFA (4 ml) and stirring at 0° C. for 1 hour. The mixture was concentrated to dryness, and a solution of the residue in DCM washed with sodium carbonate solution (sat). The organic phase was dried and evaporated to give a colourless oil 66 mg (96%). ¹H NMR (CDCl₃, 360 MHz) δ 6.99 (1H, d, J=8.4 Hz), 6.90 (2H, m), 3.36 (1H, t, J=6.1 Hz), 3.21 (2H, m), 2.99 (2H, m), 2.45–2.59 (4H, m), 2.35 (2H, m), 2.23 (2H, m), 1.57–2.04 (11H, m), 1.17 (2H, m).

Step 5 N-cyclobutyl-N'-((1R/S,10S/R,13R/S)-5-{3-[4-(trifluoromethyl)-1-piperidinyl]propyl}tricyclo[8.2.1.0³,⁸] trideca-3,5,7-trien-13-yl)sulfamide (a) Cyclobutyl-sulfamic acid 2-hydroxy-phenyl ester was prepared by adding a solution of catechol sulphate (1.32 g, 7.7 mmol) in DCM (2 ml) to a stirred solution of cyclobutylamine (600 μl, 7.0 mmol) and TEA (1.07 ml, 7.7 mmol) in DMF at 0° C., and stirring for 3 hours at this temperature. The mixture was quenched with 1M HCl (50 ml) and extracted with diethyl ether. The organic extract was washed with water, brine, dried and concentrated to dryness. Quantitative yield.

(b) The product of Step 4 (55 mg, 0.145 mmol), cyclobutyl-sulfamic acid 2-hydroxy-phenyl ester (42 mg, 0.174 mmol) and DMAP (cat) in MeCN (5 ml) were stirred and heated at 75° C. for 18 hours. The mixture was allowed to cool to room temperature then concentrated to dryness. The crude material was purified through a SCX cartridge, eluting the product with 2M NH₃ in MeOH, then further purified by column chromatography over silica gel in 4:1 isohexane-ethyl acetate to give a colourless oil 40 mg which was subsequently converted into an HCl salt to afford a white solid 41 mg (52%). ¹H NMR (CD₃OD, 400 MHz) δ 7.02 (1H, d, J=7.5 Hz), 6.95 (2H, m), 3.82 (1H, m), 3.59–3.70

(3H, m), 3.27–3.32 (2H, m), 3.13 (2H, m), 3.00 (2H, m), 2.44–2.69 (7H, m), 2.30 (2H, m), 2.18 (2H, m), 1.97–2.09 (4H, m), 1.61–1.88 (6H, m), 1.12 (2H, m). m/z 514 (M+H$^+$).

Example 118

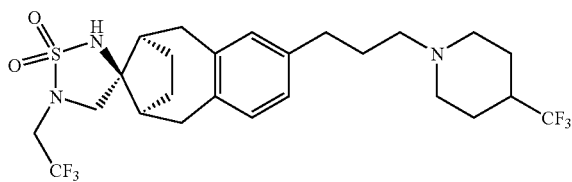

The HCl salt (98 mg) from Example 75 was dissolved in EtOH (10 ml), Pearlman's catalyst (20 mg) added and the mixture hydrogenolysed for 4 hrs at 50 psi. The mixture was filtered, concentrated and triturated with ether to give the desired product as a white powder (92 mg). $^1$H NMR (360 MHz, d$_6$-DMSO) δ$_H$ 1.03 (2H, m), 1.67 (2H, m), 1.83–2.01 (5H, brm), 2.35 (2H, m), 2.55 (4H, m), 2.63 (2H, brm), 2.94 (4H, m), 3.15 (2H, m), 3.45 (2H, s), 3.55 (2H, d, J=11.3), 4.01 (2H, q, J=9.4), 6.93–7.04 (3H, m), 7.98 (1H, s), 10.53 (1H, s).

Examples 127, 128 and 129

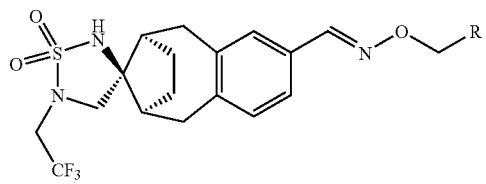

Prepared by the procedure of Example 90, using the appropriate substituted O-benzyl hydroxylamine hydrochloride instead of hydroxylamine hydrochloride.

Example 127; R=phenyl, MS(ES+) 494, MH$^+$

Example 128, R=4-fluorophenyl, MS(ES+) 512, MH$^+$

Example 129, R=4-(trifluoromethyl)phenyl, MS(ES+) 562, MH$^+$.

Example 140

[6S/R,9R/S,11R/S] 2',3',4',5,5',6,7,8,9,10-decahydro-2-(3-(2-pyrazinyl)-[1,2,4]oxadiazol-5-yl)-5'-(2,2,2-trifluoroethyl)-spiro[6,9-methanobenzocyclooctene-11,3'-[1,2,5]thiadiazole]1',1'-dioxide

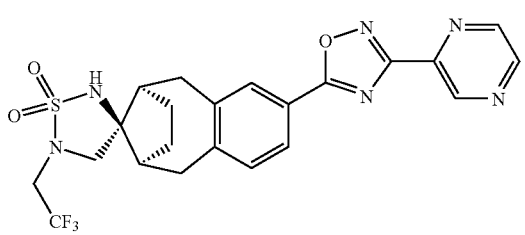

To a stirred solution of the carboxylic acid from Example 104 (223 mg, 0.55 mmol) in DMF (5 ml) under nitrogen was added 1,1'-carbonyl diimidazole (98 mg, 0.60 mmol). After 1 h, pyrazine-2-carboxamide oxime (84 mg, 0.61 mmol) was added and the resulting solution stirred for 16 h. Analysis by mass spectrometry indicated incomplete reaction. Additional amide oxime (31 mg, 0.22 mmol) was added to the reaction mixture which was the heated at 50° C. for 3.5 h. A further portion of amide oxime (38 mg, 0.28 mmol) was added and the mixture heated at 60° C. for 3 h. The mixture was allowed to cool and was then partitioned between water and ethyl acetate. The layers were separated and the aqueous phase extracted a second time with ethyl acetate. The combined organic extracts were washed with brine, dried (MgSO$_4$) and concentrated in vacuo to give the acylated amide oxime (265 mg). MS (ES+) 525 ([M+H]$^+$).

To this product (261 mg, 0.50 mmol) in THF (7 ml) under nitrogen was added potassium tert-butoxide solution (1.5 ml of a 1.0 M solution in THF, 1.5 mmol). The resulting suspension was stirred for 15 h at ambient temperature. The mixture was partitioned between dilute aqueous ammonium chloride solution and ethyl acetate. The layers were separated and the aqueous phase extracted a second time with ethyl acetate. The combined organic extracts were washed with brine, dried (MgSO$_4$) and concentrated in vacuo. Trituration with EtOAc/Et$_2$O afforded the title compound (117 mg). $^1$H NMR (400 MHz, CDCl$_3$) δ$_H$ 1.32–1.36 (2H, m), 1.76–1.80 (2H, m), 2.52–2.55 (2H, m), 2.85 (2H, app. dt, J=16.6, 7.8 Hz), 3.29–3.36 (2H, m), 3.44–3.47 (2H, m), 3.68 (1H, d, J=8.7 Hz), 3.73 (1H, d, J=8.7 Hz), 4.83 (1H, s), 7.32 (1H, d, J=7.8 Hz), 8.03 (1H, dd, J=7.8, 1.5 Hz), 8.07 (1H, s), 8.76 (1H, br s), 8.80–8.81 (1H, m), 9.46 (1H, br s); MS (ES+) 507M+H]$^+$).

Example 141

[6S/R,9R/S,11R/S] 2',3',4',5,5',6,7,8,9,10-decahydro-2-(3-(4-fluorophenyl)-[1,2,4]oxadiazol-5-yl)-5'-(2,2,2-trifluoroethyl)-spiro[6,9-methanobenzocyclooctene-11,3'-[1,2,5]thiadiazole]1',1'-dioxide

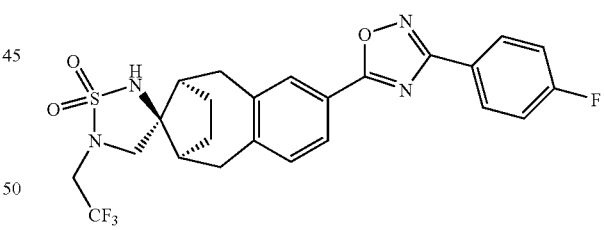

N,N'-carbonyldiimidazole (53 mg, 0.33 mmol) was added to a solution of carboxylic acid from Example 104 (120 mg, 0.30 mmol) in DMF (3 mL) and stirred at room temperature for one hour. A solution of 4-fluorobenzamidoxime (50 mg, 0.33 mmol) in DMF (3 mL) was added and the reaction stirred at 50° C. for 5 hours. N,N'-carbonyldiimidazole (53 mg, 0.33 mmol) and 4-fluorobenzamidoxime (50 mg, 0.33 mmol) were added and the reaction heated at 70° C. overnight. The cooled reaction mixture was diluted with ethyl acetate (25 mL), washed with water (4×25 mL) and brine (25 mL) and dried (Na$_2$SO$_4$). The solvent was removed in vacuo, the residue (154 mg) dissolved in tetrahydrofuran (10 mL), and potassium tert-butoxide (1.0 M in tetrahydrofuran; 0.9 mL, 0.9 mmol) added. The reaction was stirred at room temperature for 65 hours, poured into water (25 mL) and extracted with ethyl acetate (2×25 mL). The combined organic layers were washed with brine (25 mL), dried (Na₂SO₄) and evaporated under reduced pressure. The residue was purified by two sets of flash column chromatography on silica (first column eluting with 25% ethyl acetate/isohexane, second column 20% ethyl acetate/isohexane) followed by preparative HPLC to give the title cyclic sulfamide (23 mg, 15% over two steps).

δ ($^1$H, 400 MHz, CDCl₃) 8.19–8.16 (2H, m), 7.97–7.96 (2H, m), 7.30 (1H, d, J=8), 7.20 (2H, t, J=8.6), 4.72 (1H, s), 3.70 (2H, q, J=8.6), 3.46 (2H, s), 3.35–3.28 (2H, m), 2.91–2.84 (2H, m), 2.55–2.50 (2H, m), 1.83–1.73 (2H, m), 1.37–1.32 (2H, m).

Example 142

[6S/R,9R/S,11R/S] 2',3',4',5,5',6,7,8,9,10-decahydro-2-(3-(2-pyridyl)-[1,2,4]oxadiazol-5-yl)-5'-(2,2,2-trifluoroethyl)-spiro[6,9-methanobenzocyclooctene-11,3'-[1,2,5]thiadiazole]1',1'-dioxide

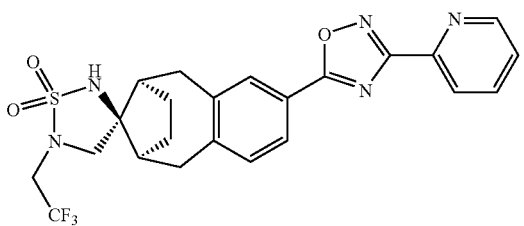

Prepared by the procedure of Example 140, using a single treatment with pyridyl 2-amidoxime in the first step. The title compound was isolated as a white solid (41 mg) by chromatography on silica eluting with 30–50% EtOAc in hexanes, followed by recrystallisation from EtOAc/Et₂O $^1$H NMR (360 MHz, CDCl₃) δ$_H$ 1.32–1.36 (2H, m), 1.75–1.79 (2H, m), 2.50–2.54 (2H, m), 2.79–2.90 (2H, m), 3.27–3.35 (2H, m), 3.43–3.49 (2H, m), 3.66–3.74 (2H, m), 4.74 (1H, s), 7.30 (1H, d, J=7.7 Hz), 7.43–7.48 (1H, m), 8.03 (1H, br d, J=8.1 Hz), 8.07 (1H, br s), 8.22 (1H, br d, J=7.7 Hz), 8.85 (1H, br d, J=4.9 Hz); MS (ES+) 506[M+H]⁺).

Example 143

[6S/R,9R/S,11R/S] 2',3',4',5,5',6,7,8,9,10-Decahydro-2-(5-(4-fluorophenyl)-1H-pyrazol-3-yl)-5'-propylspiro[6,9-methanobenzocyclooctene-11,3'-[1,2,5]thiadiazole]1',1'-dioxide

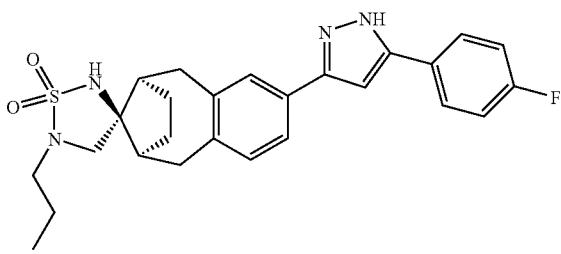

Step 1: Methyl 11-Oxo-5,6,7,8,9,10-hexahydro-6,9-methanobenzocyclooctene-2-carboxylate Prepared using the procedure described for 11-oxo-5,6,7,8,9,10-hexahydro-6,9-methanobenzocyclooctene (Justus Liebigs Ann. Chem. 1961, 650, 115) using methyl 3,4-bis(bromomethyl)benzoate in place of 1,2-bis(bromomethyl)benzene.

Step 2: Methyl 11-(2'-Methyl-propane-2'-sulfonylimino)-5,6,7,8,9,10-hexahydro-6,9-methanobenzocyclooctene-2-carboxylate

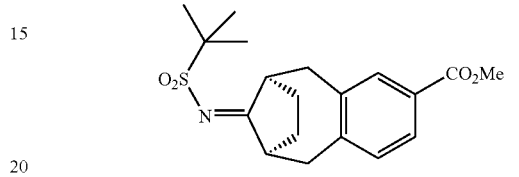

A solution of titanium (IV) chloride (10 mL, 1M in DCM) was added at 0° C. to a stirred suspension of the ketone from Step 1 (5.0 g) and tert-butyl sulfonamide (2.9 g) in chloroform (100 mL). The yellow solution was refluxed under nitrogen for 5 hours, followed by addition of triethylamine (2.8 mL). After refluxing for 18 hours, further titanium (IV) chloride solution (10 mL) and triethylamine (2.8 mL) were added. After 7 hours, the mixture was cooled and poured into saturated aqueous sodium hydrogencarbonate (400 mL). The white emulsion was filtered through Celite, washing with DCM (100 mL). The organic layer was dried over Na₂SO₄, filtered and concentrated. Trituration and rinsing with 2:1 isohexane—diethyl ether gave the sulfonimine (6.33 g, 85%) as a beige solid, δ ($^1$H, 360 MHz, CDCl₃) 1.20–1.40 (2H, m), 1.50 (9H, s), 1.75–2.00 (2H, m), 2.90–2.95 (2H, m), 3.05–3.20 (3H, m), 3.92 (3H, s), 3.95–4.05 (1H, m), 7.24–7.28 (1H, m), 7.84–7.87 (2H, m).

Step 3

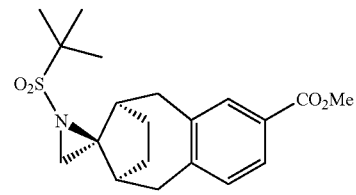

A slurry of trimethylsulfoxonium iodide (11 g) in tetrahydrofuran—DMSO (5:1, 120 mL) was added at room temperature to a stirred suspension of sodium hydride (55%, 2.2 g) in THF (30 mL) under nitrogen. After stirring for 1 hour, a solution of the sulfonimine from Step 2 (6.33 g) in DMSO (60 mL) was added at 0° C. The mixture was stirred at room temperature for 18 hours then diluted with water (500 mL) and extracted with ethyl acetate (300 mL). The organic extract was washed with water (100 ml) and brine (100 ml), dried over Na₂SO₄, filtered and concentrated. Trituration and rinsing with diethyl ether gave the aziridine (4.31 g, 66%), δ ($^1$H, 360 MHz, CDCl₃) 1.19–1.23 (2H, m), 1.70–1.80 (2H, m), 2.20–2.30 (2H, m), 2.49 (2H, d, J=5), 2.80–2.88 (2H, m), 3.60–3.75 (2H, m), 3.90 (3H, s), 7.15 (1H, d, J=8), 7.75–7.77 (2H, m); MS (ES+) 400 ([MNa]⁺).

Step 4: Methyl[6S/R,9R/S,11R/S]-11-(2'-Methyl-propane-2'-sulfonylamino)-11-propylaminomethyl-5,6,7,8,9,10-hexahydro-6,9-methanobenzocyclooctene-2-carboxylate

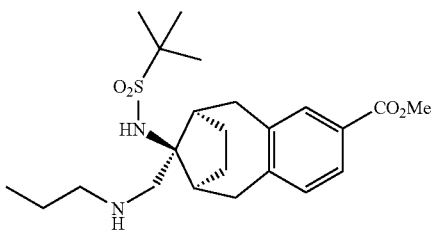

A solution of the aziridine from Step 3 (0.50 g) and n-propylamine (2.5 mL) in DMF (1.25 mL) was stirred at 100° C. in a sealed tube for 20 hours. The cooled solution was diluted with water (20 mL) and saturated aqueous ammonium chloride (20 mL), and extracted with ethyl acetate (3×20 mL). The extracts were washed with water (10 mL), brine (10 mL), dried over $Na_2SO_4$, filtered and concentrated. The resulting yellow solid was rinsed with diethyl ether (2 mL) to give the amine (0.479 g, 83%) as a white powder, δ ($^1$H, 400 MHz, $CDCl_3$) 0.93 (3H, t, J=7), 1.14–1.21 (2H, m), 1.46 (9H, s), 1.49–1.53 (2H, m), 1.65–1.70 (2H, m), 2.62–2.72 (6H, m), 2.80–2.90 (2H, m), 3.39–3.45 (2H, m), 3.89 (3H, s), 7.15 (1H, d, J=8), 7.74–7.77 (2H, m); MS (ES+) 437 ([MH]$^+$).

Step 5: Methyl[6S/R,9R/S,11R/S] 11-Amino-11-propylaminomethyl-5,6,7,8,9,10-hexahydro-6,9-methanobenzocyclooctene-2-carboxylate

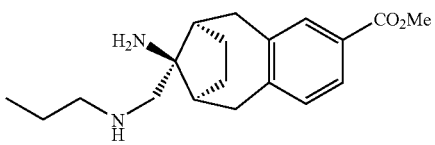

Trifluoromethanesulfonic acid (0.58 mL) was added dropwise at 0° C. to a stirred solution of the sulfonamide from Step 4 (0.476 g) in DCM (10 mL) under nitrogen. The mixture was stirred at 0° C. for 1 hour, then at room temperature for 18 hours. Further trifluoromethanesulfonic acid (0.20 mL) was added. After 2 hours, the mixture was poured into saturated aqueous sodium hydrogencarbonate (100 mL) and extracted with DCM (3×50 mL). The extracts were washed with brine (50 mL), dried over $Na_2SO_4$, filtered and concentrated. Azeotroping with diethyl ether gave the diamine (0.321 g, 93%) as a white solid, δ ($^1$H, 400 MHz, $CDCl_3$) 0.93 (3H, t, J=8), 1.12–1.16 (2H, m), 1.47–1.56 (2H, m), 1.73–1.78 (2H, m), 2.08–2.11 (2H, m), 2.58 (2H, s), 2.63 (2H, t, J=8), 2.68–2.76 (2H, m), 3.30 (2H, dd, J=18, 5), 3.89 (3H, s), 7.16 (1H, d, J=9), 7.73 (1H, d, J=9), 7.79 (1H, s); MS (ES+) 317 ([MH]$^+$).

Step 6: [6S/R,9R/S,11R/S] 2',3',4',5,5',6,7,8,9,10-Decahydro-2-carbomethoxy-5'-propylspiro[6,9-methanobenzocyclooctene-11,3'-[1,2,5]thiadiazole]1',1'-dioxide.

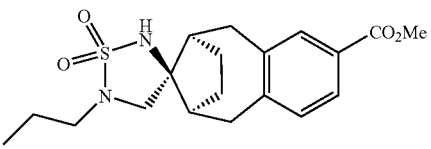

A solution of the diamine from Step 5 (0.32 g) and sulfamide (0.28 g) was refluxed in pyridine (8 mL) for 1 hour. Further sulfamide (0.2 g) was added and reflux was continued for 1 hour. Solvent was removed by evaporation, azeotroping with toluene. The residue was partitioned between 1M HCl (25 mL) and DCM (2×25 mL). The organic extracts were washed with 1M HCl (25 mL), brine (25 mL), dried over $Na_2SO_4$, filtered and concentrated to give the cyclic sulfamide (0.313 g, 83%) as a yellow foam, δ ($^1$H, 360 MHz, $CDCl_3$) 0.98 (3H, t, J=7), 1.18–1.26 (2H, m), 1.61–1.73 (4H, m), 2.40–2.50 (2H, m), 2.70–2.80 (2H, m), 3.03 (2H, dd, J=7, 7), 3.18–3.26 (4H, m), 3.90 (3H, s), 4.67 (1H, s), 7.16 (1H, d, J=8), 7.77–7.79 (2H, m); MS (ES+) 379 ([MH]$^+$).

Step 7: [6S/R,9R/S,11R/S] 2',3',4',5,5',6,7,8,9,10-Decahydro-2-carboxy-5'-propylspiro[6,9-methanobenzocyclooctene-11,3'-[1,2,5]thiadiazole]1',1'-dioxide.

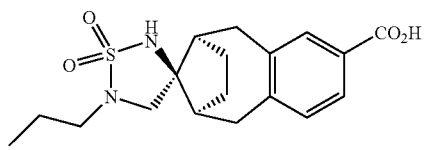

A mixture of 1M sodium hydroxide (3 mL) and the ester from Step 6 (0.39 g) in tetrahydrofuran (5 mL) was stirred at room temperature for 2 hours, then 50° C. for 1 hour. The mixture was diluted with water (25 mL) and washed with diethyl ether (25 mL). The aqueous solution was acidified with 1M aqueous citric acid (50 mL) and extracted with DCM (3×20 mL). The extracts were washed with brine (20 mL), dried over $Na_2SO_4$, filtered and concentrated to give the acid (0.30 g) as an off-white solid, δ ($^1$H, 360 MHz, $d_6$-DMSO) 0.90 (3H, t, J=7), 0.96–1.00 (2H, m), 1.55 (2H, tq, J=7, 7), 1.65–1.70 (2H, m), 2.30–2.37 (2H, m), 2.66 (2H, dd, J=15, 8), 2.89 (2H, t, J=7), 3.17 (2H, s), 3.19 (2H, d, J=15), 7.22 (1H, d, J=8), 7.65 (1H, d, J=8), 7.68 (1H, s), 7.71 (1H, s), 12.70 (1H, s).

Step 8: [6S/R,9R/S,11R/S] 2',3',4',5,5',6,7,8,9,10-Decahydro-2-(3-(4-fluorophenyl)-3-hydroxy-prop-2-en-1-one-1-yl)-5'-propylspiro[6,9-methanobenzocyclooctene-11,3'-[1,2,5]thiadiazole]1',1'-dioxide.

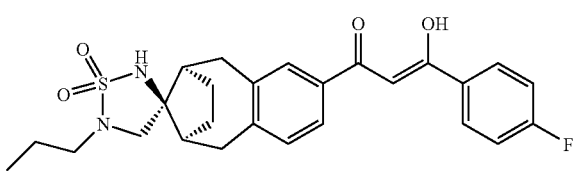

A solution of lithium bis(trimethylsilyl)amide (1.1 mL, 1M in THF) was added at −78° C. to a stirred solution of 4'-fluoroacetophenone (0.135 mL) in THF (2 mL) under nitrogen. The yellow solution was warmed to room temperature for 30 minutes then recooled to −78° C. A mixture of the acid from Step 7 (0.10 g) and 1,1,-carbonyldiimidazole (0.045 g) in THF (1 mL) was stirred at room temperature under nitrogen for 1 hour, then added by syringe to the enolate solution prepared above at −78° C. The mixture was stirred at room temperature for 3 hours then poured into saturated aqueous ammonium chloride (50 mL) and extracted with ethyl acetate (25 mL). The extract was filtered through a teflon membrane and concentrated. Flash column chromatography on silica, eluting with ethyl acetate, gave the diketone (0.029 g, 22%) as a yellow solid, δ ($^1$H, 400 MHz, CDCl$_3$) 1.00 (3H, t, J=7), 1.20–1.32 (2H, m), 1.65–1.75 (4H, m), 2.46–2.48 (2H, m), 2.75–2.84 (2H, m), 3.03 (2H, t, J=7), 3.19–3.29 (4H, m), 4.80 (1H, s), 6.77 (1H, s), 7.17 (2H, dd, J=9, 9), 7.21 (1H, d, J=8), 7.71–7.73 (2H, m), 8.01 (2H, dd, J=9, 5), 15.00 (1H, s).

Step 9:

A solution of the diketone from Step 8 (0.029 g) and hydrazine hydrate (0.5 mL) in ethanol (2 mL) was refluxed under nitrogen for 4 hours. The solution was cooled, diluted with water (20 mL), acidified with 1M aqueous citric acid and extracted with ethyl acetate (2×10 mL). The extracts were filtered through a teflon membrane and concentrated. Preparative thin-layer chromatography, eluting with 50% ethyl acetate-isohexane gave the title pyrazole (0.014 g, 49%) as a white powder, δ ($^1$H, 400 MHz, CDCl$_3$) 0.99 (3H, t, J=7), 1.21–1.28 (2H, m), 1.62–1.74 (4H, m), 2.43–2.46 (2H, m), 2.68–2.76 (2H, m), 3.04 (2H, t, J=7), 3.19–3.25 (4H, m), 4.90 (1H, s), 6.77 (1H, s), 7.11–7.16 (3H, m), 7.41–7.43 (2H, m), 7.72 (2H, dd, J=9, 5); MS (ES+) 481 ([MH]$^+$).

Example 144

[11-endo] 2',3',4',5,5',6,7,8,9,10-Decahydro-5'-cyclopentylspiro[6,9-methanobenzocyclooctene-11,3'-[1,2,5]thiadiazole] 1',1'-dioxide

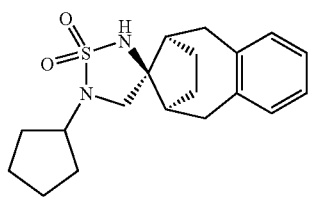

Step 1: [6S/R,9R/S,11R/S] 11-(2'-Methyl-propane-2'-sulfonylamino)-11-cyclopentylaminomethyl-5,6,7,8,9,10-hexahydro-6,9-methanobenzocyclooctene

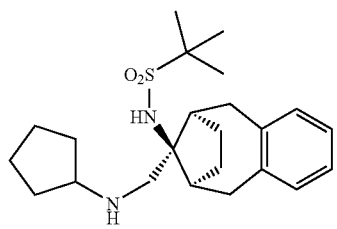

Prepared from 11-oxo-5,6,7,8,9,10-hexahydro-6,9-methanobenzocyclooctene (J. Org. Chem. 1982, 47, 4329) using the procedure described in Example 143, Steps 2–4, substituting cyclopentylamine for propylamine. Yield 87%, δ ($^1$H, 400 MHz, CDCl$_3$) 1.16–1.21 (2H, m), 1.25–1.38 (2H, m), 1.46 (9H, s), 1.52–1.70 (6H, m), 1.80–1.88 (2H, m), 2.58 (2H, dd, J=15, 8), 2.65–2.73 (2H, m), 2.81 (2H, s), 3.09 (1H, tt, J=7, 7), 3.39 (2H, d, J=15), 7.08 (4H, s).

Step 2: [6S/R,9R/S,11RS] 11-Amino-11-cyclopentylaminomethyl-5,6,7,8,9,10-hexahydro-6,9-methanobenzocyclooctene

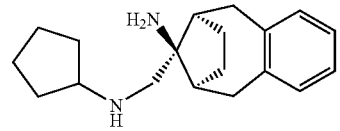

Trifluoromethanesulfonic acid (0.20 mL) was added to a stirred solution of the sulfonamide from Step 1 (0.10 g) and anisole (0.15 mL) in DCM at 0° C. under nitrogen. The solution was stirred at room temperature for 2 hours then diluted with DCM (5 mL) and extracted with water (20 mL) and 1M HCl (10 mL). The aqueous extracts were combined and washed with diethyl ether (5 mL), then neutralised with aqueous sodium hydrogencarbonate. The resulting white solid was collected, redissolved in 10% methanol—DCM, dried over Na$_2$SO$_4$, filtered and concentrated to give the diamine (0.042 g, 60%) as a yellow oil, MS (ES+) 285 ([MH]$^+$).

Step 3:

The diamine from Step 2 was converted to the cyclic sulfamide using the procedure described in Example 143, Step 6. Yield 60%, δ ($^1$H, 36 0MHz, CDCl$_3$) 1.24–1.29 (2H, m), 1.60–1.80 (8H, m), 1.95–2.05 (2H, m), 2.38–2.43 (2H, m), 2.67 (2H, dd, J=16, 8), 3.16 (2H, d, J=16), 3.21 (2H, s), 3.50 (1H, tt, J=7, 7), 4.62 (1H, s), 7.05–7.12 (4H, m); MS (ES+) 347 ([MH]$^+$).

Example 145

[6S/R,9R/S,11R/S] 2',3',4',5,5',6,7,8,9,10-Decahydro-2-cyano-5'-propylspiro[6,9-methanobenzocyclooctene-11,3'-[1,2,5]thiadiazole]1',1'-dioxide

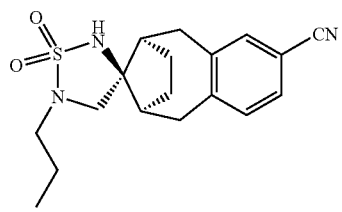

A mixture of the acid from Example 143, Step 7 (0.20 g), HBTU (0.25 g), diisopropylethylamine (0.25 mL) and 4'-fluoro-2-aminoacetophenone hydrochloride salt (0.10 g) in acetonitrile was stirred at 50° C. for 5 hours. The mixture was diluted with water (20 mL) and the yellow solid was collected, redissolved in 10% methanol—DCM, dried over Na$_2$SO$_4$, filtered and concentrated. The resulting yellow foam was dissolved in THF (2 mL) and Burgess reagent (0.24 g) was added. The mixture was subject to microwave irradiation (120° C., 600 seconds, Smith Personal Synthesiser microwave reactor). The cooled mixture was diluted with ethyl acetate (10 mL) and washed with water (20 mL), filtered through a teflon membrane and concentrated. Preparative thin-layer chromatography (x 2) eluting with 50% ethyl acetate-isohexanes, then with 2% methanol—DCM, isolated the title nitrile (white powder, 0.023 g, 12%) as the less polar of two products. δ ($^1$H, 360 MHz, CDCl$_3$) 0.97 (3H, t, J=7), 1.20–1.26 (2H, m), 1.60–1.76 (4H, m), 2.45–2.49 (2H, m), 2.68–2.78 (2H, m), 3.03 (2H, t, J=7), 3.20–3.33 (4H, m), 4.90 (1H, s), 7.20 (1H, d, J=8), 7.39–7.42 (2H, m); MS (ES+) 346 ([MH]$^+$).

Example 146

[6S/R,9R/S,11R/S] 2',3',4',5,5',6,7,8,9,10-decahydro-2-(5-(4-fluorophenyl)-oxazol-2-yl)-5'-propylspiro[6,9-methanobenzocyclooctene-11,3'-[1,2,5]thiadiazole]1',1'-dioxide

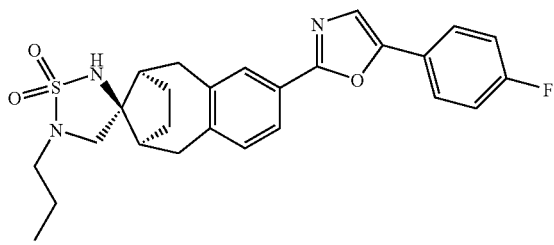

Obtained from Example 145 as the more polar product (white powder, 0.033 g, 11%). δ ($^1$H, 360 MHz, CDCl$_3$) 0.99 (3H, t, J=7), 1.29–1.33 (2H, m), 1.64–1.75 (4H, m), 2.42–2.50 (2H, m), 2.73–2.86 (2H, m), 3.04 (2H, t, J=7), 3.23–3.27 (4H, m), 4.63 (1H, s), 7.12–7.17 (2H, m), 7.21 (1H, d, J=8), 7.37 (1H, s), 7.68–7.72 (2H, m), 7.83–7.85 (2H, m); MS (ES+) 482 ([MH]$^+$).

Example 147 [11-endo] 2',3',4',5,5',6,7,8,9,10-Decahydro-5'-cyclobutylspiro[6,9-methanobenzocyclooctene-11,3'-[1,2,5]thiadiazole] 1',1'-dioxide

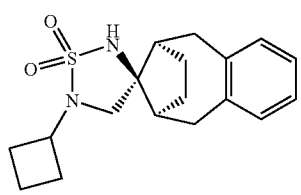

Prepared by the procedures described in Example 144, substituting cyclobutylamine for cyclopentylamine (67%), δ ($^1$H, 360 MHz, CDCl$_3$) 1.25–1.30 (2H, m), 1.67–1.86 (4H, m), 2.20–2.26 (4H, m), 2.39–2.43 (2H, m), 2.67 (2H, dd, J=16, 8), 3.15–3.19 (4H, m), 3.80 (1H, tt, J=8, 8), 4.65 (1H, s), 7.07–7.13 (4H, m); MS (ES+) 365 ([M+H+MeOH]$^+$).

Example 148

[6S/R,9R/S,11R/S] 2',3',4',5,5',6,7,8,9,10-Decahydro-2-(1,1-dimethylethyl)-5'-cyclopentylspiro[6,9-methanobenzocyclooctene-11,3'-[1,2,5]thiadiazole] 1',1'-dioxide

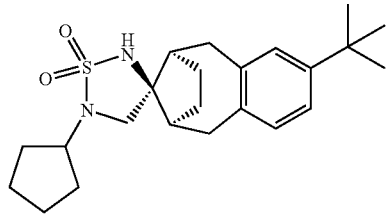

Trifluoromethanesulfonic acid (0.3 mL) was added at room temperature to a stirred solution of the sulfonamide from Example 144, Step 1 (0.18 g) in DCM (2 mL) under nitrogen. After 1.5 hours the mixture was poured into saturated aqueous sodium hydrogencarbonate (30 mL) and extracted with DCM (20 mL). The extract was filtered through a teflon membrane and concentrated. The residual oil was dissolved in pyridine (4 mL) with sulfamide (0.12 g) and refluxed under nitrogen for 18 hours. Solvent was removed by evaporation and the residue was partitioned between 1M HCl (15 mL) and DCM (10 mL). The organic layer was filtered through a teflon membrane and concentrated. Flash column chromatography, eluting with 15% ethyl acetate—isohexanes, gave the title sulfamide (0.026 g, 16%) as a white powder, δ ($^1$H, 360 MHz, CDCl$_3$) 1.25–1.31 (11H, m), 1.68–1.75 (8H, m), 1.95–2.05 (2H, m), 2.35–2.45 (2H, m), 3.08–3.20 (4H, m), 3.42–3.50 (1H, m), 4.62 (1H, s), 7.00 (1H, d, J=8), 7.07 (1H, s), 7.20 (1H, d, J=8); MS (ES+) 403 ([MH]$^+$).

Example 149

[6S/R,9R/S,11R/S] 2',3',4',5,5',6,7,8,9,10-Decahydro-2-(3-(2-pyrazinyl)-1,2,4-oxadiazol-5-yl)-5'-propylspiro[6,9-methanobenzocyclooctene-11,3'-[1,2,5]thiadiazole] 1',1'-dioxide

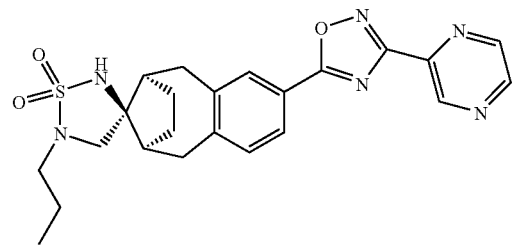

Prepared from the acid from Example 143, Step 7 (0.15 g) by the procedure of Example 140, using one treatment with 2-pyrazinamide oxime (0.07 g) in the first step. The title oxadiazole (0.023 g, 12%) was isolated as a white solid by preparative thin-layer chromatography, eluting with 10% methanol—DCM., δ ($^1$H, 400 MHz, d$_6$-DMSO) 0.91 (3H, t, J=7), 1.00–1.10 (2H, m), 1.52–1.60 (2H, m), 1.70–1.78 (2H, m), 2.35–2.40 (2H, m), 2.75–2.85 (2H, m), 2.90 (2H, t, J=7), 3.20 (2H, s), 3.24–3.30 (2H, m), 7.42 (1H, d, J=8), 7.77 (1H, s), 7.95 (1H, d, J=8), 8.00 (1H, s), 8.89–8.90 (2H, m), 9.35 (1H, s); MS (ES+) 467 ([MH]+).

Example 150

[6S/R,9R/S,11R/S] 2',3',4',5,5',6,7,8,9,10-Decahydro-2-(3-(2-pyridyl)-1,2,4-oxadiazol-5-yl)-5'-propyl-spiro[6,9-methanobenzocyclooctene-11,3'-[1,2,5] thiadiazole] 1',1'-dioxide

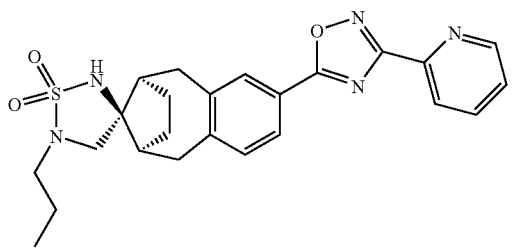

Prepared using the procedure described in Example 149, substituting 2-pyridinamide oxime for 2-pyrazinamide oxime (50%), δ (¹H, 400 MHz, CDCl₃) 0.99 (3H, t, J=7), 1.25–1.33 (2H, m), 1.67 (2H, tq, J=7, 7), 1.72–1.80 (2H, m), 2.46–2.51 (2H, m), 2.75–2.90 (2H, m), 3.04 (2H, t, J=7), 3.20–3.32 (4H, m), 4.64 (1H, s), 7.29 (1H, d, J=8), 7.45–7.47 (1H, m), 7.88 (1H, ddd, J=5, 5, 1), 8.01 (1H, d, J=8), 8.08 (1H, s), 8.21–8.23 (1H, m), 8.85–8.86 (1H, m); MS (ES+) 466 ([MH]+).

Example 151

[6S/R,9R/S,11R/S] 2',3',4',5,5',6,7,8,9,10-decahydro-2-(3-(1-acetylpiperidin-4-yl)-[1,2,4]oxadiazol-5-yl)-5'-(2,2,2-trifluoroethyl)-spiro[6,9-methanobenzocyclooctene-11,3'-[1,2,5]thiadiazole] 1',1'-dioxide

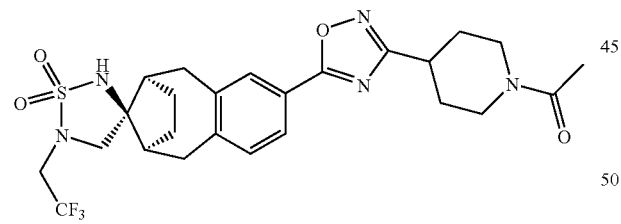

Step 1: 1-acetylpiperidine-4-carboxamidoxime.

1-Acetylpiperidine-4-carbonitrile (300 mg, 1.96 mmol), hydroxylamine hydrochloride (204 mg, 2.94 mmol) and triethylamine (492 µl, 3.53 mmol) were combined in ethanol (10 ml) and heated under reflux overnight. The solvent was removed in vacuo, and the residue triturated with ethanol to give the amidoxime as its hydrochloride salt (100 mg, 23%). m/z 186, 187.

Step 2:

N,N'-carbonyldiimidazole (53 mg, 0.33 mmol) was added to a solution of carboxylic acid from Example 104 (120 mg, 0.30 mmol) in DMF (3 mL) and stirred at room temperature for one hour. A sonicated mixture of amidoxime hydrochloride from step 1 (73 mg, 0.33 mmol) and Hünig's base (114 µl, 0.66 mmol) in DMF (3 mL) was added and the reaction stirred at 70° C. overnight. The cooled reaction mixture was diluted with ethyl acetate (25 mL), washed with water (4×25 mL) and brine (25 mL) and dried (Na₂SO₄). The solvent was removed in vacuo. The residue (95 mg) was dissolved in THF (10 mL) and potassium tert-butoxide (1.0 M in THF; 0.5 mL, 0.5 mmol) was added. After stirring at room temperature for 65 hours, the mixture was poured into water (25 mL) and extracted with ethyl acetate (2×25 mL). The combined organic layers were washed with brine (25 mL), dried (Na₂SO₄) and evaporated under reduced pressure. The residue was purified by FractionLynx, after flash column chromatography and preparative TLC failed to remove impurities, to give the title cyclic sulfamide (6 mg, 4% over 2 steps).

δ (¹H, 360 MHz, CDCl₃) 7.87–7.86 (2H, m), 7.27 (1H, d, J=8.6), 4.82 (1H, s), 4.57 (1H, d, J=13.7), 3.91 (1H, d, J=13.3), 3.70 (2H, q, J=8.6), 3.45 (2H, s), 3.34–3.22 (3H, m), 3.16–3.07 (1H, m), 2.93–2.77 (3H, m), 2.54–2.48 (2H, m), 2.13 (3H, s), 2.13–2.06 (2H, m), 1.96–1.81 (2H, m), 1.78–1.73 (2H, m), 1.36–1.27 (2H, m). m/z 554, 555, 556.

| GLOSSARY | |
| --- | --- |
| o/n | overnight |
| DCM | dichloromethane |
| PDC | pyridinium dichromate |
| DMF | N,N-dimethylformamide |
| DMSO | dimethylsulfoxide |
| THF | tetrahydrofuran |
| DIBAL | diisobutylaluminium hydride |
| LAH | lithium aluminium hydride |
| MOM | methoxymethyl |
| TFA | trifluoroacetic acid |
| TEA | triethylamine |
| DMAP | 4-(dimethylamino)pyridine |
| Boc | t-butoxycarbonyl |
| DIPEA | diisopropylethylamine |
| HBTU | O-benzotriazol-1-yl-N,N,N',N'-tetramethyluronium hexafluorophosphate |
| DME | dimethoxyethane |

What is claimed is:

1. A compound of formula I(D):

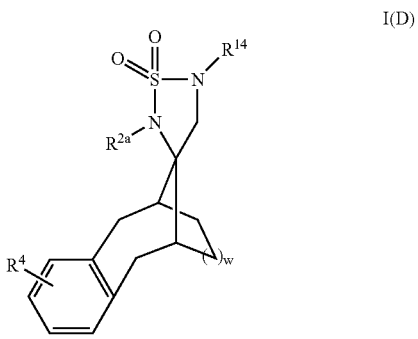

wherein:

$R^{2a}$ represents H or $C_{2-6}$acyl which is optionally substituted with a carboxylic acid group or with an amino group;

$R^4$ represents $R^9$, halogen, CN, NO₂, —OR⁹, —SR⁹, —S(O)ₜR¹⁰ where t is 1 or 2, —N(R⁹)₂, —COR⁹, —CO₂R⁹, —OCOR¹⁰, —CH=N—OR¹¹, —CON(R⁹)₂, —SO₂N(R⁹)₂, —NR⁹COR¹⁰, —NR⁹CO₂R¹⁰, —NR⁹SO₂R¹⁰, —CH=CHCH₂N(R¹⁶)₂, —CH₂N(R¹⁶)₂, —NHCOCH₂OR¹⁰ or —NHCOCH₂N(R¹⁶)₂;

R⁷ represents H or R⁸; or two R⁷ groups together with a nitrogen atom to which they are mutually attached may complete a pyrrolidine, piperidine, piperazine or morpholine ring;

R⁸ represents C₁₋₁₀alkyl, perfluoroC₁₋₆alkyl, C₃₋₁₀cycloalkyl, C₃₋₆cycloalkylC₁₋₆alkyl, C₂₋₁₀alkenyl, C₂₋₁₀alkynyl, Ar or —C₁₋₆alkylAr;

R⁹ H or R¹⁰; or two R⁹ groups together with a nitrogen atom to which they are mutually attached may complete a pyrrolidine, piperidine, piperazine or morpholine ring which is optionally substituted by R¹², —COR¹² or —SO₂R¹²;

R¹⁰ represents C₁₋₁₀alkyl, perfluoroC₁₋₆alkyl, C₃₋₁₀cycloalkyl, C₃₋₆cycloalkylC₁₋₆alkyl, C₂₋₁₀alkenyl, C₂₋₁₀alkynyl, C₆₋₁₀aryl, heteroaryl, heterocyclyl, C₆₋₁₀arylC₁₋₆alkyl, heteroarylC₁₋₆ alkyl, heterocyclylC₁₋₆alkyl, C₁₋₆arylC₂₋₆alkenyl, or heteroarylC₂₋₆alkenyl, wherein the alkyl, cycloalkyl, alkenyl and alkynyl groups optionally bear one substituent selected from halogen, CF₃, NO₂, CN, —OR¹¹, —SR¹¹, —SO₂R¹², —COR¹¹, —CO₂R¹¹, —CON(R¹¹)₂, —OCOR¹², —N(R¹¹)₂ and —NR¹¹COR¹²; and the aryl, heteroaryl and heterocyclic groups optionally bear up to 3 substituents independently selected from halogen, NO₂, CN, R¹², —OR¹¹, —SR¹¹, —SO₂R¹², —COR¹¹, —CO₂R¹¹, —CON(R¹¹)₂, —OCOR¹², —N(R₁₁)₂ and —NR¹¹COR¹²;

R¹¹ represents H or R¹²; or two R¹¹ groups together with a nitrogen atom to which they are mutually attached may complete a heterocyclic ring system of 3–10 atoms, 0–2 of which (in addition to said nitrogen atom) are selected from O, N and S, said ring system bearing 0–2 substituents selected from halogen, CN, NO₂, oxo, R¹², OH, OR¹², NH₂, NHR¹², CHO, CO₂H, COR¹² and CO₂R¹²;

R¹² represents C₁₋₆alkyl which is optionally substituted with halogen, CN, OH, C₁₋₄alkoxy or C₁₋₄alkoxycarbonyl; perfluoroC₁₋₆alkyl, C₃₋₇cycloalkyl, C₂₋₆alkenyl, C₂₋₆alkynyl, Ar, —C₁₋₆alkylAr, ArOC₁₋₆alkyl or C-heterocyclyl which is optionally substituted with halogen, CN, C₁₋₆alkyl, OH, perfluoroC₁₋₆alkyl, C₂₋₆acyl, C₁₋₄alkoxy or C₁₋₄alkoxycarbonyl;

R¹⁴ represents H, C₁₋₁₀alkyl, perfluoroC₁₋₆alkyl, C₃₋₁₀cycloalkyl, C₃₋₆cycloalkylC₁₋₆alkyl, C₂₋₁₀ alkenyl, C₂₋₁₀alkynyl, C₁₋₆aryl, heteroaryl, C₆₋₁₀arylC₁₋₆alkyl, or heteroarylC₁₋₆alkyl, wherein the alkyl, cycloalkyl, alkenyl and alkynyl groups optionally bear one substituent selected from halogen, CN, NO₂, —OR⁷, —SR⁷, —S(O)ₜR⁸ where t is 1 or 2, —N(R⁷)₂, —COR⁷, —CO₂R⁷, —OCOR⁸, —CON(R⁷)₂, —NR⁷COR⁸, —C₁₋₆alkylNR⁷COR⁸, —NR⁷CO₂R⁸ and —NR⁷SO₂R⁸, and the aryl and heteroaryl groups optionally bear up to 3 substituents selected from R⁸, halogen, CN, NO₂, —OR⁷, —SR⁷, —S(O)ₜR⁸ where t is 1 or 2, —(R⁷)₂, —COR⁷, —CO₂R⁷, —OCOR⁸, —CON(R⁷)₂, —NR⁷COR⁸, —C₁₋₆alkylNR⁷COR⁸, —NR⁷CO₂R⁸ and —NR⁷SO₂R⁸;

each R¹⁶ independently represents H or R¹⁰, or two R¹⁶ groups together with the nitrogen to which they are mutually attached complete a mono- or bicyclic heterocyclic ring system of 5–10 ring atoms selected from C, N, O and S, said ring system optionally having an additional aryl or heteroaryl ring fused thereto, said heterocyclic system and optional fused ring bearing 0–3 substituents independently selected from halogen, oxo, NO₂, CN, R¹², —OR¹¹, —SR¹¹, —SO₂R¹², —COR¹¹, —CO₂R¹¹, —CON(R¹¹)₂, —OCOR¹², —N(R₁₁)₂ and —NR¹¹COR¹²;

Ar represents phenyl or heteroaryl either of which optionally bears up to 3 substituents independently selected from halogen, CF₃, NO₂, CN, OCF₃, C₁₋₆alkyl and C₁₋₆alkoxy;

"heterocycly" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom is other than C;

w is 1 or 2;

or a pharmaceutically acceptable salt thereof.

2. A compound according to claim 1 wherein R²ᵃ is H.

3. A compound according to claim 1 which is

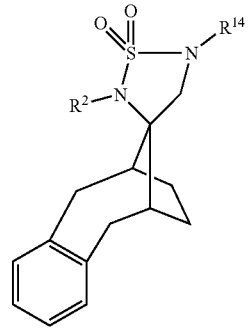

and pharmaceutically acceptable salts thereof.

4. A pharmaceutical composition comprising one or more compounds according to claim 1 and a pharmaceutically acceptable carrier.

5. A method of treatment of a subject suffering from or prone to Alzheimer's disease which comprises administering to that subject an effective amount of a compound according to claim 1.

6. A compound according to claim 3 wherein:

R²ᵃ is H, R¹⁴ is n-propyl, and R⁴ is selected from 3-pyridyl, (pyridin-3-yl)methoxy, —CO₂Me, 2-(pyridin-2-yl)ethoxy, 3-(morpholin-4-yl)propyl, —CH₂OH, —CHO, —CH=CHCO₂Me, 3-[(4-methyl-1,2,4-triazol-3-yl) thio]prop-1-enyl, —CN, 5-(4-fluorophenyl) oxazol-2-yl, 5-(4-fluorophenyl)-1,3,4-oxadiazol-2-yl, 3-(pyridin-2-yl) -1,2,4-oxadiazol-5-yl, 3-pyrazinyl-1,2, 4-oxadiazol-5-yl, —CH=CHCH₂OH and 5-(4-fluorophenyl)pyrazol-3-yl; or R²ᵃ is H, R¹⁴ is n-propyl, and R⁴ is —CH=CHCH₂N(R¹⁶)₂ where —N(R¹⁶)₂ is selected from morpholin-4-yl, 4-trifluoromethylpiperidin-1-yl, 4,4-difluoropiperidin-1-yl, 4-carbamoylpiperidin-1-yl, 4-ethoxycarbonylpiperidin-1-yl, 4-carboxypiperidin-1-yl, 4-hydroxypiperidin-1-yl, 1,2,3,6-tetrahydropyridinyl, 5-aza-2-oxabicyclo[2.2.1]hept-1-yl, N-[(furan-2-yl)methyl]amino, N,N-bis(2-methoxyethyl)amino, N-(indan-1-yl)amino and N-[(pyridin-2-yl)methyl] amino; or $R^{2a}$ is H, $R^{14}$ is n-propyl, and $R^4$ is —OCH$_2$CH$_2$N(R$^{11}$)$_2$ where -N(R$^{11}$)$_2$ is selected from morpholin-4-yl and 2-oxo-imidazolin-1-yl; or $R^{2a}$ is H, $R^{14}$ is 2,2,2-trifluoroethyl and $R^4$ is selected from —OH, —CO$_2$Me, —CH$_2$OH, —CHO, —CO$_2$H, —CH=CHCO$_2$Me, —CH=CHCO$_2$H, —CH=CHCH$_2$OH, —CH=N-OH, —CH=N—OEt, —CH$_2$CH$_2$CO$_2$Me, —CH$_2$CH$_2$CO$_2$H, (morpholin-4-yl)methyl, 2-(imidazol-1-yl)ethoxy, 3-(4-trifluoromethylpiperidin-1-yl)propyl, —CH=N—OCH$_2$Ph, —CH=N—OCH$_2$(4-F-C$_6$H$_4$), —CH=N—OCH$_2$(4-CF$_3$—C$_6$H$_4$), 3-pyrazinyl-1,2,4-oxadiazol-5-yl, 3-(4-fluorophenyl)-1,2,4-oxadiazol-5-yl, 3-(pyridin-2-yl)-1,2,4-oxadiazol-5-yl, —CH=N—OCH$_2$(2-F-C$_6$H$_4$), —CH=N—OCH$_2$CH=CH$_2$, —CH=N—OCH$_2$(3-F-C$_6$H$_4$) and —CH=N—OCH$_2$(2,4-di-Cl-C$_6$H$_3$); or $R^{2a}$ is H, $R^{14}$ is 2,2,2-trifluoroethyl and $R^4$ is —CH=CHCH$_2$N(R$^{16}$)$_2$ where —N(R$^{16}$)$_2$ is selected from morpholin-4-yl, 4-trifluoromethylpiperidin-1-yl, 5-aza-2-oxabicyclo[2.2.1]hept-1-yl, 4,4-difluoropiperidin-1-yl, 4-hydroxy-4-trifluoromethylpiperidin-1-yl, 4-methylpiperidin-1-yl, 3-oxo-4-phenylpiperazin-1-yl, 3-oxo-4-cyclohexylpiperazin-1-yl, 3-oxo-piperazin-1-yl, N-(tetrahydrofuran-3-yl)amino, N-methyl-N-(tetrahydrofuran-3-yl) amino, N-(tetrahydropyran-4-yl) amino, N-methyl-N-(tetrahydropyran-4-yl)amino, N-(dioxanylmethyl)amino, N-[(tetrahydropyran-2-yl)methyl]amino, 3-hydroxypiperidin-1-yl, 5-aza-2-oxabicyclo[5.4.0]undeca-7,9,11-trien-5-yl, 2-(phenoxymethyl)morpholin-4-yl, N-[(4-phenylmorpholin-2-yl)methyl]amino, 3,3-difluoropyrrolidin-1-yl, N-(2,2,2-trifluoroethyl)amino and 3-(pyridin-3-yl)pyrrolidin-1-yl; or $R^{2a}$ is H, $R^{14}$ is 2,2,2-trifluoroethyl and $R^4$ is —OCH$_2$CH$_2$N(R$^{11}$)$_2$ where N(R$^{11}$)$_2$ is selected from morpholin-1-yl, 4-acetylpiperazin-1-yl, N-(2-methoxyethyl)amino, N-[(thiophen-2-yl)methyl]amino, N-[(pyridin-3-yl)methyl]amino, N-(methoxycarbonylmethyl) amino, 3-oxo-4-phenylpiperazin-1-yl and 4-trifluoromethypiperidin-1-yl.

\* \* \* \* \*

UNITED STATES PATENT AND TRADEMARK OFFICE
CERTIFICATE OF CORRECTION

PATENT NO.        : 7,138,400 B2
APPLICATION NO.   : 10/415751
DATED             : November 21, 2006
INVENTOR(S)       : Ian James Collins et al.

It is certified that error appears in the above-identified patent and that said Letters Patent is hereby corrected as shown below:

At column 101, line 3, after "$(R^{16})_2$,", insert -- -$CH_2OR^{10}$- --.

At column 101, line 12, after "$R^9$" insert -- represents --.

At column 101, line 21, delete "$C_{1-6}arylC_{2-6}alkenyl$" and replace with -- $C_{6-10}arylC_{2-6}alkenyl$ --.

At column 101, line 59, delete "-$(R^7)_2$," and replace with -- -$N(R^7)_2$, --.

At column 102, line 10, delete "heterocycly" and replace with -- heterocyclyl --.

UNITED STATES PATENT AND TRADEMARK OFFICE
CERTIFICATE OF CORRECTION

PATENT NO. : 7,138,400 B2
APPLICATION NO. : 10/415751
DATED : November 21, 2006
INVENTOR(S) : Ian James Collins et al.

It is certified that error appears in the above-identified patent and that said Letters Patent is hereby corrected as shown below:

At column 102, line 25-35, delete

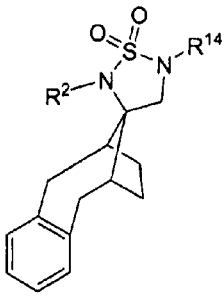

and replace with

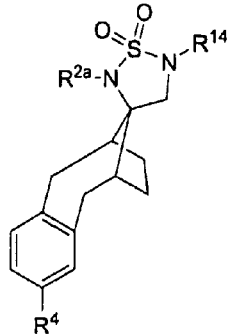

Signed and Sealed this

Fourth Day of March, 2008

JON W. DUDAS
*Director of the United States Patent and Trademark Office*